(12) United States Patent
Brigham et al.

(10) Patent No.: US 7,074,399 B2
(45) Date of Patent: Jul. 11, 2006

(54) TREATMENT OF INFLAMMATION WITH P20

(75) Inventors: Kenneth L. Brigham, Nashville, TN (US); Arlene A. Stecenko, Nashville, TN (US); Linda Sealy, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 455 days.

(21) Appl. No.: 09/789,836

(22) Filed: Feb. 20, 2001

(65) Prior Publication Data

US 2002/0082204 A1    Jun. 27, 2002

Related U.S. Application Data

(60) Provisional application No. 60/183,584, filed on Feb. 18, 2000.

(51) Int. Cl.
*A01N 63/00* (2006.01)
*A61K 48/00* (2006.01)

(52) U.S. Cl. .................... 424/93.2; 435/320.1
(58) Field of Classification Search ............... 514/44; 435/69.1, 455, 456, 320.1; 424/93.2, 93.21
See application file for complete search history.

(56) References Cited

U.S. PATENT DOCUMENTS

| | | | |
|---|---|---|---|
| 4,937,190 A | 6/1990 | Palmenberg et al. | |
| 5,215,892 A | 6/1993 | Kishimoto et al. | |
| 5,360,894 A | 11/1994 | Kishimoto et al. | |
| 5,545,563 A | 8/1996 | Darlington et al. | 435/320.1 |
| 5,804,445 A | 9/1998 | Brasier | |
| 5,830,725 A | 11/1998 | Nolan et al. | |
| 5,874,209 A | 2/1999 | Karin et al. | |
| 6,165,720 A | 12/2000 | Felgner et al. | |

OTHER PUBLICATIONS

J Kuby, Immunology, WH Freeman and Company, 2nd Ed., pp. 7-9, 313-316, 318 and 559-560.*
GM Rubanyi, Molecular Aspects of Medicine, "The future of human gene therapy," 2001, 22, pp. 113-142.*
WF Anderson, Nature, "Human gene therapy," Apr. 1998, vol. 392, pp. 25-30.*
IM Verma et al., Nature, "Gene therapy-promises, problems and prospects," Sep. 1997, vol. 389, pp. 239-242.*
Akira et al. EMBO J. 1990, 9:1897-1906.*
Chang et al. Mol Cell Biol. 1990, 10:6642-53).*
Poli et al. Cell, 63, 643-653, 1990.*
Croniger, et al.; *C/EBP and the Control of Phosphoenolpyruvate*; Journal of Biological Chemistry; Nov. 28, 1998; pp. 31629-31632; vol. 273:48; USA.
Darlington, et al.; *The Role of C/EBP Genes in Adipocyte Differentiation*; Journal of Biological Chemistry; Nov. 13, 1998; pp. 30057-30060; vol. 273:46; USA.
Diehl; *Roles of CCAAT/Enhancer-binding Proteins in Regulation of Liver Regenerative Growth*; Journal of Biological Chemistry; Nov. 20, 1998; pp. 30843-30846; vol. 273:46; USA.
Hanson; *Biological Role of the Isoforms of C/EBP Minireview Series*; Journal of Biological Chemistry; Oct. 30, 1998; p. 28543; vol. 273:44; USA.
Harris, et al.; *C/EBP Cooperates with p21 to inhibit cdk2 kinase activity and induces growth arrest independent of DNA binding*; JBC Papers in Press; May 21, 2001; pp. 1-41.
Henderson, et al.; *C/EBP Proteins Activate Transcription from the Human Immunodeficiency Virus Type I Long Terminal Repeat in Macrophages/Monocytes*; Journal of Virology; Sep. 1995; pp. 5337-5344; vol. 69:9.
Honda, et al.; *Type I Interferon Induces Inhibitory 16-kD CCAAT/Enhancer Binding Protein (C/EBP)β, Repressing the HIV-I Long Terminal Repeat in Macrophages: Pulmonary Tuberculosis Alters C/EBP Expression, Enhancing HIV-I Replication*; J. Exp. Med.; Oct. 5, 1998; pp. 1255-1265; vol. 188:7.
Kowenz-Leutz, et al.; *A C/EBPβ Isoform Recruits the SWI/SNF Complex to Activate Myeloid Genes*; Molecular Cell; Nov. 1999; pp. 735-743; vol. 4.
Lekstrom-Himes, et. al.; *Biological Role of the CCAAT/Enhancer-binding Protein Family of Transcription Factors*; Journal of Biological Chemistry; Oct. 30, 1998; pp. 28545-28548; vol. 273:44; USA.
Poli, Valeria; *The Role of C/EBP Isoforms in the Control of Inflammatory and Native Immunity Functions*; Journal of Biological Chemistry; Nov. 6, 1998; pp. 29279-29282; vol. 273:45; USA.

* cited by examiner

*Primary Examiner*—Brian Whiteman
(74) *Attorney, Agent, or Firm*—Needle & Rosenberg PC

(57) ABSTRACT

The present invention provides compositions, methods, and kits for treating inflammation and regulating inflammatory responses including cytokine, prostanoid, prostaglandin, and growth factor expression.

16 Claims, 30 Drawing Sheets

Information on CEBPB in LocusLink Database (NCBI)

| Locus ID | Organism | Symbol | Description | Position |
|---|---|---|---|---|
| 1051 | HS | CEBPB | CCAAT/enhancer binding protein (C/EBP), beta | 20q13.1 |
| 12608 | Mm | Cebpb | CCAAT/enhancer binding protein (C/EBP), beta | 2 95.5 cM |
| 24253 | Rn | Cebpb | Liver activating protein (LAP, also NF-IL6, nuclear factor-IL6, previously designated TCF5) | 3 |

*Homo sapiens* Official Gene Symbol and Name (HGNC)
CEBPB: CCAAT/enhancer binding protein (C/EBP), beta Locus Information

| | |
|---|---|
| LocusID: | 1051 |
| Type: | Gene with protein product, function known or inferred |
| Alternate Symbols: | TCF5, CRP2, IL6DBP, LAP, NFIL6 |
| Product: | CCAAT/enhancer binding protein (C/EBP), beta |
| Alias: | CCAAT/enhancer binding protein (C/EBP), beta (transcription factor-5) |
| UniGene: | Hs.99029 |
| OMIM: | 189965 |

Map Information

| | | |
|---|---|---|
| Chromosome: | 20 | |
| Cytogenetic: | 20q131.1 | RefSeq |
| Mouse Homology Map: | 2 95.5 cM | Cebpb |

NCBI Reference Sequences (RefSeq)

| Category: | PROVISIONAL | |
|---|---|---|
| Nucleotide: | NM 005194 | |
| Protein: | NP 005185 | CCAAT/enhancer binding protein (C/EBP), beta |
| Domains: | Basic region leucin zipper bZIP transcription factor | 120 92 |
| GenBank Source: | X52560 | |

| Category: | NT 011399 |
|---|---|
| Genomic Contig: | Supported by alignment with mRNA |
| Evidence: | XM 009510 |
| Model Nucleotide: | XP 009510 |
| Model Protein: | |
| GenBank Sequences Nucleotide X52560 | Protein CAA36794 |

*FIG. 2B*

CEBPB: CCAAT/enhancer binding protein (C/EBP), beta

Locus Information

| LocusID: | 12608 |
|---|---|
| Type: | Gene with protein product, function known or inferred |
| Product: | CCAAT/enhancer binding protein (C/EBP), beta |
| UniGene: | Mm.4863 |

Map Information

| Chromosome: | 2 | |
|---|---|---|
| Genetic: | 2 95.5 | MGD |
| Human Homology Map: | 20q13.1 | CEBPB |

NCBI Reference Sequences (RefSeq)

| Category: | PROVISIONAL | |
|---|---|---|
| Nucleotide: | NM 009883 | |
| Protein: | NP 034013 | CCAAT/enhancer binding protein (C/EBP), beta |
| Domains: | Basic region leucin zipper bZIP transcription factor | 122 92 |
| GenBank Source: | X62600 | |

GenBank Sequences

| Nucleotide | Type | Protein | Strain |
|---|---|---|---|
| S78572 | g | | |
| M61007 | m | AAA37192 | BALB/c |
| X626200 | m | CAA44484 | |

FIG. 2C

*Rattus norvegicus* Official Gene Symbol and Name (RATMAP)
Cebpb: Liver activating protein (LAP, also NF-IL6, nuclear factor-IL6, previously designated TCF5)

Locus Information

| LocusID: | 24253 |
|---|---|
| Type: | Gene with protein product, function known or inferred |
| Alternate Symbols: | TCF5, I16dbp, LAP, NF-IL6 |

Map Information

| Chromosome: | 3 |
|---|---|
| Cytogenetic: | 3 |

FIG. 2D (SEQ ID NO:1)

PubMed Nucleotide Query
LOCUS HSNFIL6                1910 bp DNA              PRI 02-JUL-19
DEFINITION Human gene for nuclear factor NF-IL6.
ACCESSION X52560 VERSION X52560.1
SOURCE human.         ORGANISM Homo sapiens     Tissue Type Placen
Promoter 67..73 "TATA box" underlined, Primary Transcript 95..>1336
Coding Sequence (CDS) C/EBPβ-1 299..1336 in bold (C/EBPβ-1)
C/EBPβ-2 approximately 368 to 1336
C/EBPβ-3 approximately 893 to 1336
Polyadenylation Signal 1895..1900 underlined

```
  1   gtccttcgcg tcccggcggc gcggcggagg ggccggcgtg acgcagcggt tgctacgggc
 61   cgcccttata aataaccggg ctcaggagaa actttagcga gtcagagccg cgcacgggac
121   tgggaagggg acccacccga gggtccagcc accagccccc tcactaatag cggccacccc
181   ggcagcggcg gcagcagcag cagcgacgca gcggcgacag ctcagagcag ggaggccgcg
```

C/EBPB-1
```
241   cacctgcggg ccggccggag cgggcagccc caggcccccct ccccgggcac ccgcgttcatg
301    caacgcctg gtggcctggg acccagcatg tctcccctg ccgccgccgc cgcctgcctt
```

C/EBPB-2
```
361   taaatccatg gaagtggcca acttctacta cgaggcggac tgcttggctg ctgcgtacgg
421   cggcaaggcg gccccgcgg cgcccccgc ggccagaccc gggccgcgcc ccccgccgg
481   cgagctgggc agcatccggcg accacgagcg cgccatcgac ttcagcccgt acctggagcc
541   gctgggcgcg ccgcaggccc cggcgccgc cacggccacg gacaccttcg aggcggctcc
601   gcccgcgccc gccccgcgc ccgcctcctc cgggcagcac cacgacttcc tctccgacct
661   cttctccgac gactacgggg gcaagaactg caagaagccg gccgagtacg gctacgtgag
721   cctggggcgc ctgggggctg ccaagggcgc gctgcacccc ggctgcttcg cgcccctgca
781   cccaccgccc ccgccgccgc cgccgcccgc cgagctcaag gcggagccgg gcttcgagcc
```

C/EBPB-3
```
841   cgcggactgc aagcggaagg aggaggccgg ggcgccgggc ggcggcgcag gcatggcggc
901   gggcttcccg tacgcgctgc gcgcttacct cggctaccag gcggtgccga gcggcagcag
961   cgggagcctc tccacgtcct cctcgtccag cccgccggc acgccgagcc ccgctgacgc
1021  caaggcccc ccgaccgcct gctacgcggg ggccgggccg gcgccctcgc aggtcaagag
1081  caaggccaag aagaccgtgg acaagcacag cgacgagtac aagatccggc gcgagcgcaa
1141  caacatcgcc gtgcgcaaga gccgcgacaa ggccaagatg cgcaacctgg agacgcagca
1201  caaggtcctg gagctcacgg ccgagaacga gcggctgcag aagaaggtgg agcagctgtc
1261  gcgcgagctc agcaccctgc ggaacttgtt caagcagctg cccgagcccc tgctcgcctc
1321  ctccggccac tgctagcgcg gccccgcgg cgtccccctg gggccggccg gggctgagac
1381  tccggggagc gcccgcgccc gcgccctcgc cccnccccc nnnnccgcaa aactttggca
1441  ctggggcact tggcagcngg ggagcccgtc ggtaatttta atattttatt atatatatat
1501  atctatattt tgccaaccaa ccgtacatgc agatggctcc cgcccgtggt gtataaagaa
1561  gaaatgtcta tgtgtacaga tgaatgataa actctctgct ctccctctgc ccctctccag
1621  gcccggcggg cggggccggt ttcgaagttg atgcaatcgg tttaaacatg gctgaacgcg
1681  tgtgtacacg ggactgacgc aacccacgtg taactgtcag ccgggccctg agtaatcgct
1741  taaagatgtt ctagggcttg ttgctgttga tgttttgttt tgttttgttt tttggtcttt
1801  ttttgtatta taaaaaataa tctatttcta tgagaaaaga ggcgtctgta tattttggga
1861  atcttttccg tttcaagcaa ttaagaacac ttttaataaa cttttttttg
```

*FIG. 3A*

(SEQ ID NO:5)

```
LOCUS       pCEBPB     345 aa    PRI    26-JUL-1999
DEFINITION  CCAAT/enhancer binding protein (C/EBP), beta.
ACCESSION   NP_005185 Same as RefSeq (Protein)
VERSION     NP_005185.1  GI:4885129   PID:g4885129
DBSOURCE    REFSEQ: locus CEBPB accession NM_005194.1 (transcript)
KEYWORDS    .
SOURCE      human.
ORGANISM    Homo sapiens
```

|     | HUMAN C/EBPβ-1 | | HUMAN C/EBPβ-2 | | | |
|---|---|---|---|---|---|---|
| 1   | MQRLVAWDPA | CLPLPPPPPA | FKSMEVANFY | YEADCLAAAY | GGKAAPAAPP | AARPGPRPPA |
|     | 1 | | 24 | | | |

| 61 | GELGSIGDHE | RAIDFSPYLE | PLGAPQAPAP | ATATDTFEAA | PPAPAPAPAS | SGQHHDFLSD |

| 121 | LFSDDYGGKN | CKKPAEYGYV | SLGRLGAAKG | ALHPGCFAPL | HPPPPPPPPP | AELKAEPGFE |

|     | | | HUMAN C/EBPβ-3 | | | |
|---|---|---|---|---|---|---|
| 181 | PADCKRKEEA | GAPGGGAGMA | AGFPYALRAY | LGYQAVPSGS | SGSLSTSSSS | SPPGTPSPAD |
|     | | | 199 | | | |

| 241 | AKAPPTACYA | GAGPAPSQVK | SKAKKTVDKH | SDEYKIRRER | NNIAVRKSRD | KAKMRNLETQ |

| 301 | HKVLELTAEN | ERLQKKVEQL | SRELSTLRNL | FKQLPEPLLA | SSGHC |

FIG. 3B (SEQ ID NO:8)

LOCUS MMCEBP 1500 bp mRNA ROD 23-NOV-1992

DEFINITION M.musculus mRNA for C/EBP beta.    ACCESSION X62600

The coding sequence (CDS) is in bold (including the TAG stop codon).

The ATG start codons for C/EBPβ-1, C/EBPβ-2, and C/EBPβ-3 are boxed.

Approximate: C/EBPβ-1 (108 to 998), C/EBPβ-2 (170 to 998), C/EBPβ-3 (560-998).

```
   1    gcccgttgcc aggcgccgcc ttataaacct cccgctcggc cgccgccgcg ccgagtccga
                              TATA Signal                           MOUSE C/EBPβ-1
  61    gccgcgcacg ggaccgggac gcagcggagc ccgcgggccc cgcgttc[atg] caccgcctgc
                                                                  MOUSE C/EBPβ-2
 121    tggcctggga cgcagcatgc ctcccgccgc cgcccgccgc ctttagaccc [atg]gaagtgg
 181    ccaacttcta ctacgagccc gactgcctgg cctacgggc caaggcggcc cgcgccgcgc
 241    cgcgcgcccc cgccgccgag ccggccattg gcgagcacga gcgcgccatc gacttcagcc
 301    cctacctgga ccgctcgcg cccgccgcgg acttcgccgc cccgcgccc cgcaccacg
 361    acttcctctc cgacctcttc gccgacgact acggcgccaa gccgagcaag aagccggccg
 421    actacggtta cgtgagcctc ggccgcgcgg gcgccaaggc cgcgccgccc gcctgcttcc
 481    cgccgccgcc tcccgcggcg ctcaaggcgg agccgggctt cgaacccgcg gactgcaagc
                           MOUSE C/EBPβ-3
 541    gcgcggacga cgcgcccgcc [atg]gcggccg gtttcccgtt cgccctgcgc gcctacctgg
 601    gctaccaggc gacgccgagc ggcagcagcg gcagcctgtc cacgtcgtcg tcgtccagcc
 661    cgcccggcac gccgagcccc gccgacgcca aggccgcgcc cgccgcctgc ttcgcgggc
 721    cgccggccgc gcccgccaag gccaaggcca agaagacggt ggacaagctg agcgacgagt
 781    acaagatgcg gcgcgagcgc aacaacatcg cggtgcgcaa gagccgcgac aaggccaaga
 841    tgcgcaacct ggagacgcag cacaaggtgc tggagctgac ggcggagaac gagcggctgc
 901    agaagaaggt ggagcagctg tcgcgagagc tcagcaccct gcggaacttg ttcaagcagc
 961    tgcccgagcc gctgctggcc tcggcgggcc actgctagcg cggcgcggtg gcgtgggggg
1021    cgccgcggcc accgtgcgcc ctgccccgcg cgctccggcc ccgcgcgcgc gcccggacca
1081    ccgtgcgtgc cctgcgcgca cctgcacctg caccgagggg caccgcgggg cacaccgcgg
1141    gcacgcgcgg cgcacgcacc tgcacagcgc accgggttc gggacttgat gcaatccgga
1201    tcaaacgtgg ctgagcgcgt gtggacacgg gactacgcaa cacacgtgta actgtctagc
1261    cgggccctga gtaatcacct taaagatgtt cctgcgggt tgttgatgtt tttggttttg
1321    tttttgtttt ttgttttgtt ttgtttttt ttttggtctt attattttt ttgtattata
1381    taaaaagtt ctatttctat gagaaaagag gcgtatgtat atttgagaac cttttccgtt
1441    tcgagcatta aagtgaagac attttaataa acttttttgg gagaatgttt aaaagccaaa
                              PolyA Signal
```

*FIG. 3C*

(SEQ ID NO:9)

| | | | |
|---|---|---|---|
| LOCUS | CAA44484 | 296 aa | ROD 23-NOV-1992 |
| DEFINITION | C/EBP BETA | | |
| ACCESSION | CAA44484.1 | | |
| SOURCE | house mouse | ORGANISM | Mus musculus |

```
     Mouse C/EBPβ-1      Mouse C/EBPβ-2
001 MHRLLAWDAA  CLPPPPAAFR  PMEVANFYYE  PDCLAYGAKA  ARAAPRAPAA  EPAIGEHERA
      1                     22

061 IDFSPYLEPL  APAADFAAPA  PAHHDFLSDL  FADDYGAKPS  KKPADYGYVS  LGRAGAKAAP

Mouse C/EBPβ-3
121 PACFPPPPPA  ALKAEPGFEP  ADCKRADDAP  AMAAGFPFAL  RAYLGYQATP  SGSSGSLSTS
                                          152

181 SSSSPPGTPS  PADAKAAPAA  CFAGPPAAPA  KAKAKKTVDK  LSDEYKMRRE  RNNIAVRKSR

241 DKAKMRNLET  QHKVLELTAE  NERLQKKVEQ  LSRELSTLRN  LFKQLPEPLL  ASAGHC
```

*FIG. 3D*

(SEQ ID NO:10)

DEFINITION Rattus norvegicus mRNA for C/EBPβ.

Withdrawn from GenBank

Coding sequence (CDS) is in bold (including the TAG stop codon).

ATG start codons for C/EBPβ-1, C/EBPβ-2, and C/EBPβ-3 are boxed.

1739 nucleotides

```
0001 aggggccccg gcgtgacgca gcccgttgcc aggcgccgcc ttataaacct
0051 ccgctcggcc gccgccgagc cgagtccgag ccgcgcacgg gaccgggacg
```

C/EBPβ-1

```
0101 cagcggagcc cgcgggcccc gcgttcatgc accgcctgct ggcctgggac
```

C/EBPβ-2

```
0151 gcagcatgcc tcccgccgcc gcccgccgcc tttagaccca tggaagtggc
0201 caacttctac tacgagcccg actgcctggc ctacggggcc aaggcggccc
0251 gcgccgcgcc gcgcgccccc gccgccgagc cggccatcgg cgagcacgag
0301 cgcgccatcg acttcagccc ctacctggag ccgctcgcgc cgccgccgc
0351 ggacttcgcc gcgcccgcgc ccgcgcacca cgacttcctt tccgacctct
0401 tcgccgacga ctacggcgcc aagccgagca gaagccgtc cgactacggt
0451 tacgtgagcc tcggccgcgc gggcgccaag gccgcaccgc ccgcctgctt
0501 cccgccgccg cctcccgccg cactcaaggc cgagccgggc ttcgaacccg
```

C/EBPβ-3

```
0551 cggactgcaa gcgcgcggac gacgcgcccg ccatggcggc cggcttcccg
0601 ttcgccctgc gcgcctacct gggctaccag gcgacgccga gcggcagcag
0651 cggcagcctg tccacgtcgt cgtcgtccag cccgcccggg acgccgagcc
0701 ccgccgacgc caaggcgcg cccgccgcct gcttcgcggg gccgccggcc
0751 gcgcccgcca aggccaaggc caagaaggcg gtggacaagc tgagcgacga
0801 gtacaagatg cggcgcgagc gcaacaacat cgcggtgcgc aagagccgcg
0851 acaaggccaa gatgcgcaac ctggagacgc agcacaaggt gctggagctg
0901 acggcggaga cgagcggct gcagaagaag gtggagcagc tgtcgcgaga
0951 gctcagcacg ctgcggaact tgttcaagca gctgcccgag ccgctgctgg
1001 cctcggcggg tcactgctag cccggcgggg gtggcgtggg ggcgccgcgg
1051 ccaccctggg caccgtgcgc cctgccccgc gcgctccgtc cccgcgcgcg
1101 cccgggcacc gtgcgtgcac cgcgcgcacc tgcacctgca ccgaggggac
1151 accgtgggca ccgcgcgcac gcacctgcac cgcgcaccgg gtttcgggac
1201 ttgatgcaat ccggatcaaa cgtggctgag cgcgtgtgga cacgggactg
1251 acgcaacaca cgtgtaactg tcagccgggc cctgagtaat cacttaaaga
1301 tgttcctgcg gggttgttgc tgttgatgtt tttcttttg ttttttgttt
1351 tttgttttt tttggtcctt attattttt tgtattatat aaaaaagttc
```

*FIG. 3E-1*

```
1451 tcgagcatta aagtgaagac attttaataa acttttttgg agaatgttta
1501 aaaacctttt gggggcagta gttggctttt gaaaaaaaat ttttttctt
1551 ccctcctgac tttggattta tgcgagattt tgttttttgt gtttctggtg
1601 tgtagggggc tgcgggttat ttttggttg  tgtgtggtgg tgggtggggg
1651 tgtcgcatct gggtttttct cctccctgg  cagatgggat gccagcccct
181  cccccagga  gaggggcag  agtgccgggt caggaattc
```

5' UTR is approximately the first 126 nucleotides
rat C/EBPβ-1 is from approximately 127 to 921 (including TAG sequence)
rat C/EBPβ-2 is from approximately 109 to 921
rat C/EBPβ-3 is from approximately to 498 to 921

*FIG. 3E-2*

(SEQ ID:11)

```
      Rat C/EBPβ-1           Rat C/EBPβ-2
01    MHRLLAWDAA CLPPPPAAFR  PMEVANFYYE PDCLAYGAKA GRAAPRAPAA
      1                     22

51    EPAIGEHERA IDFSPYLEPL APAAADFAAP APAHHDFLSD LFADDYGAKP

101   SKKPSDYGYV SLGRAGAKAA PPACFPPPPP AALKAEPGFE PADCKRADDA

Rat C/EBPβ-3
151   PAMAAGFPFA LRAYLGYQAT PSGSSGSLST SSSSSPPGTP SPADAKAAPA
          153

201   ACFAGPPAAP AKAKAKKAVD KLSDEYKMRR ERNNIAVRKS RDKAKMRNLE

251   TQHKVLELTA ENERLQKKVE QLSRELSTLR NLFKQLPEPL LASAGHC -
```

C-terminal

FIG. 3F

Human & Mouse CEBPB Sequence Comparison

SIM - Alignment Tool For Protein Sequences URL "http://www.expasy.ch/tools/sim-prot.html"
Results with: Gap open penalty: 12; Gap extension penalty: 4; Comparison matrix: BLOSUM62
72.8% identity in 345 residues overlap; Score: 990.0; Gap frequency: 14.2%
Sequence 1: Human C/EBPβ (345 residues)(SEQ ID NO:5)   ❶ Start site of C/EBPβ-1 Isoform
Sequence 2: Mouse C/EBPβ (296 residues)(SEQ ID NO:9)   ❷ Start site of C/EBPβ-2 Isoform
                                                       ❸ Start site of C/EBPβ-3 Isoform

```
                            ❶
Human   1   MQRLVAWDPACLPLPPPPAAFKSMEVANFYYEADCLAAAYGGKAAPAAPPAARPGPRPPA
Mouse   1   MHRLLAWDAACLP--PPPAAFRPMEVANFYYEPDCLA--YGAKAARAAP------RAPA
            * ** *****    ****** ********* ****  **    *        * **

❷
Human   61  GELGSIGDHERAIDFSPYLEPLGAPQAPAPATATDTFEAAPPAPAPAPASSGQHHDFLSD
Mouse   50  AE-PAIGEHERAIDFSPYLEPL----APADFA------APAPA------HHDFLSD
              *  ** *************    ***  *      *****      *******

❸
Human   121 LFSDDYGGKNCKKPAEYGYVSLGRLGAAKGALHPGCFAPLHPPPPPPPAELKAEPGFE
Mouse   90  LFADDYGAKPSKKPADYGYVSLGRAGAK--AAPPACF-------PPPPAALKAEPGFE
            ** **** * ****** ******* ***   **  *        ** *********

Human   181 PADCKRKEEAGAPGGGAGMAAGFPYALRAYLGYQAVPSGSGSLSTSSSSSPPGTPSPAD
Mouse   140 PADCKRADDAPA-----MAAGFPFALRAYLGYQATPSGSGSLSTSSSSSPPGTPSPAD
            ******   **      ****** **********  **********************

Human   241 AKAPPTACYAGAGPAPSQVKSKAKKTVDKHSDEYKIRRERNNIAVRKSRDKAKMRNLETQ
Mouse   194 AKAAPAACFAGPPAAPA--KAKAKKTVDKLSDEYKMRRERNNIAVRKSRDKAKMRNLETQ
            *** * ** **  * *   ********* ***** *************************

Human   301 HKVLELTAENERLQKKVEQLSRELSTLRNLFKQLPEPLLASSGHC
Mouse   252 HKVLELTAENERLQKKVEQLSRELSTLRNLFKQLPEPLLASAGHC
            ***************************************** ***
```

FIG. 4A

Human & Rat CEBPB Sequence Comparison

SIM - Alignment Tool For Protein Sequences URL "http://www.expasy.ch/tools/sim-prot.html"
Results with: Gap open penalty: 12; Gap extension penalty: 4; Comparison matrix: BLOSUM62
71.9% identity in 345 residues overlap; Score: 986.0; Gap frequency: 13.9%
Sequence 1: Human C/EBPβ (345 residues)(SEQ ID NO:05)   ❶ Start site of C/EBPβ-1 Isoform
Sequence 2: Rat C/EBPβ (297 residues)(SEQ ID NO:12)   ❷ Start site of C/EBPβ-2 Isoform
                                                       ❸ Start site of C/EBPβ-3 Isoform

```
                    ❶
Human  001  MQRLVAWDPACLPLPPPPA-FKSMEVANFYYEADCLAAAYGGKAAPAAPPAARPGPRPPA
Rat    001  MHRLLAWDAACLP---PPPAAFRPMEVANFYYEPDCLA--YGAKAGRAAP------RAPA
            * ** ****  *** *** ***  ******** *** **   * ***             * **
                                            ❷
Human  061  GELGSIGDHERAIDFSPYLEPLGAPQAPAPATATDTFEAAPPAPAPAPASSGQHHDFLSD
Rat    050  AE-PAIGEHERAIDFSPYLEPL-----APAAA----DFAAPAPA------HHDFLSD
            *  * ************** *   ***    *  ****      *******

Human  121  LFSDDYGGKNCKKPAEYGYVSLGRLGAAKGALHPGCFAPLHPPPPPPPAELKAEPGFE
Rat    091  LFADDYGAKPSKKPSDYGYVSLGRAGA-K-AAPPACF-------PPPPAALKAEPGFE
            ** ****  * *** ****** **  *  ** **        ******** *****
                            ❸
Human  181  PADCKRKEEAGAPGGGAGMAAGFPYALRAYLGYQAVPSGSSGSLSTSSSSPPGTPSPAD
Rat    141  PADCKRADDAPA------MAAGFPFALRAYLGYQATPSGSSGSLSTSSSSPPGTPSPAD
            *******   **        ****** *********  ********************

Human  241  AKAPPTACYAGAGPAPSQVKSKAKKTVDKHSDEYKIRRERNNIAVRKSRDKAKMRNLETQ
Rat    195  AKAAPAACFAGPPAAPA--KAKAKKAVDKLSDEYKMRRERNNIAVRKSRDKAKMRNLETQ
            *** * ** ***  *    ****  *** ***** *************************

Human  301  HKVLELTAENERLQKKVEQLSRELSTLRNLFKQLPEPLLASSGHC
Rat    253  HKVLELTAENERLQKKVEQLSRELSTLRNLFKQLPEPLLASAGHC
            *****************************************  ***
```

FIG. 4B

Mouse & Rat CEBPB Sequence Comparison

SIM - Alignment Tool For Protein Sequences URL "http://www.expasy.ch/tools/sim-prot.html"
Results with: Gap open penalty: 12; Gap extension penalty: 4; Comparison matrix: BLOSUM62
98.7% identity in 297 residues overlap; Score: 1529.0; Gap frequency: 0.3%
Sequence 1: Mouse C/EBPβ (296 residues) (SEQ ID NO:09)   ❶ Start site of C/EBPβ-1 Isoform
Sequence 2: Rat    C/EBPβ (297 residues) (SEQ ID NO:12)   ❷ Start site of C/EBPβ-2 Isoform
                                                          ❸ Start site of C/EBPβ-3 Isoform

```
                       ❶                    ❷
Mouse    1 MHRLLAWDAACLPPPPAAFRPMEVANFYYEPDCLAYGAKAARAAPRAPAAEPAIGEHERA
Rat      1 MHRLLAWDAACLPPPPAAFRPMEVANFYYEPDCLAYGAKAGRAAPRAPAAEPAIGEHERA
           ****************************************** ****************

Mouse   61 IDFSPYLEPLAPAA-DFAAPAPAHHDFLSDLFADDYGAKPSKKPADYGYVSLGRAGAKAA
Rat     61 IDFSPYLEPLAPAAADFAAPAPAHHDFLSDLFADDYGAKPSKKPSDYGYVSLGRAGAKAA
           ************** ***************************** ***************
                              ❸
Mouse  120 PPACFPPPPPAALKAEPGFEPADCKRADDAPAMAAGFPFALRAYLGYQATPSGSSGSLST
Rat    121 PPACFPPPPPAALKAEPGFEPADCKRADDAPAMAAGFPFALRAYLGYQATPSGSSGSLST
           ************************************************************

Mouse  180 SSSSSPPGTPSPADAKAAPAACFAGPPAAPAKAKAKKTVDKLSDEYKMRRERNNIAVRKS
Rat    181 SSSSSPPGTPSPADAKAAPAACFAGPPAAPAKAKAKAVDKLSDEYKMRRERNNIAVRKS
           ************************************ ***********************

Mouse  240 RDKAKMRNLETQHKVLELTAENERLQKKVEQLSRELSTLRNLFKQLPEPLLASAGHC
Rat    241 RDKAKMRNLETQHKVLELTAENERLQKKVEQLSRELSTLRNLFKQLPEPLLASAGHC
           ********************************************************
```

FIG. 4C

Human Polypeptide for C/EBPβ-3
(SEQ ID NO:7)

```
01   MAAGFPYALR AYLGYQAVPS GSSGSLSTSS SSSPPGTPSP ADAKAPPTAC

*                       NLS B
51   YAGAGPAPSQ VKSKAKKTVD KHSDEYKIRR ERNNIAVRKS RDKAKMRNLE
                     NLS A

101  TQHKVLELTA ENERLQKKVE QLSRELSTLR NLFKQLPEPL LASSGHC
```

FIG. 5

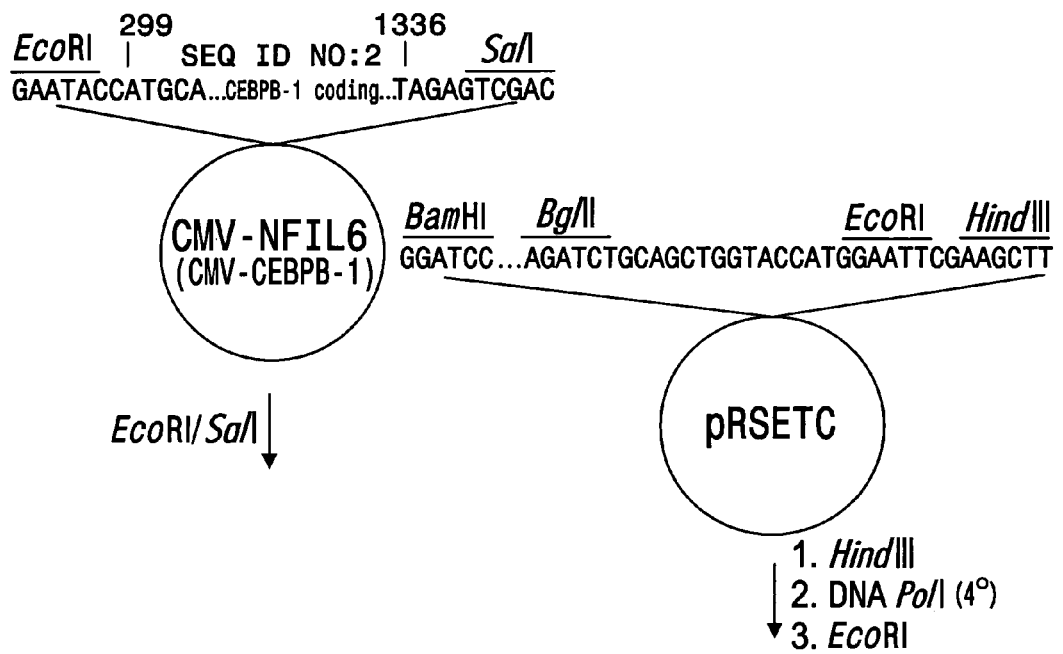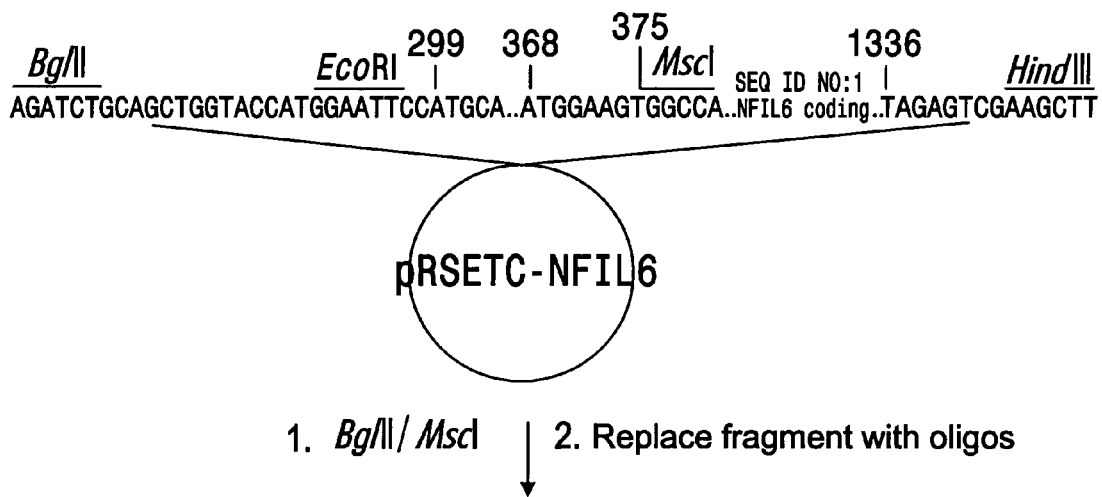
FIG. 11D

Top strand of mutant oligo:

```
                       BamHI       299
                         |          |
5' GATCTGCAGCTGGTACCATGGGCTACCATGGAACGCCTGGTGGCCTGGGACCCAGC
   ATGTCTCCCCCTGCCGCCGCCGCCGCCTGCCTTTAAATCCGGAGAAGTGG  3'
                                                    |
                                                   368
```

Wild type NFIL6 (CEBPB) sequence:
```
                                    299
                                     |
5' GATCTGCAGCTGGTACCATGGAATTCCATGCAACGCCTGGTGGCCTGGGACCCAGC
   ATGTCTCCCCCTGCCGCCGCCGCCGCCTGCCTTTAAATCCATGGAAGTGG  3'
                                                    |
                                                   368
```

Note: Residues that differ from wild-type are underlined.

Generation of pCDNA3.1 HisA-C/EBPβ-1

1. Digest pRSETC-C/EBPβ-1 (described above) with *Hind*III
2. Incubate at 4°C with DNA *Pol*I to generate blunt ends
3. Digest with *Bam*HI to release a 1,082 bp fragment
4. Insert fragment into *Bam*HI and *Eco*RV digest pCDNA3.1HisA

*FIG. 11E*

PREFERRED HUMAN DNA CODONS

| AMINO ACIDS | | | PREFERRED CODONS | | | | | |
|---|---|---|---|---|---|---|---|---|
| ALANINE | Ala | A | GCC | GCT | GCA | GCG | | |
| CYSTEINE | Cys | C | TGC | TGT | | | | |
| ASPARTIC ACID | Asp | D | GAC | GAT | | | | |
| GLUTAMIC ACID | Glu | E | GAG | GAA | | | | |
| PHENYLALANINE | Phe | F | TTC | TTT | | | | |
| GLYCINE | Gly | G | GGC | GGG | GGA | GGT | | |
| HISTIDINE | His | H | CAC | CAT | | | | |
| ISOLEUCINE | Ile | I | ATC | ATT | ATA | | | |
| LYSINE | Lys | K | AAG | AAA | | | | |
| LEUCINE | Lue | L | CTG | CTC | TTG | CTT | CTA | TTA |
| METHIONINE | Met | M | ATG | | | | | |
| ASPARAGINE | Asn | N | AAC | AAT | | | | |
| PROLINE | Pro | P | CCC | CCT | CCA | CCG | | |
| GLUTAMINE | Gln | Q | CAG | CAA | | | | |
| ARGININE | Arg | R | CGC | AGG | CGG | AGA | CGA | CGT |
| SERINE | Ser | S | AGC | TCC | TCT | AGT | TCA | TCG |
| THREONINE | Thr | T | ACC | ACA | ACT | ACG | | |
| VALINE | Val | V | GTG | GTC | GTT | GTA | | |
| TRYPTOPHAN | Trp | W | TGG | | | | | |
| TYROSINE | Tyr | Y | TAC | TAT | | | | |

*FIG. 12*

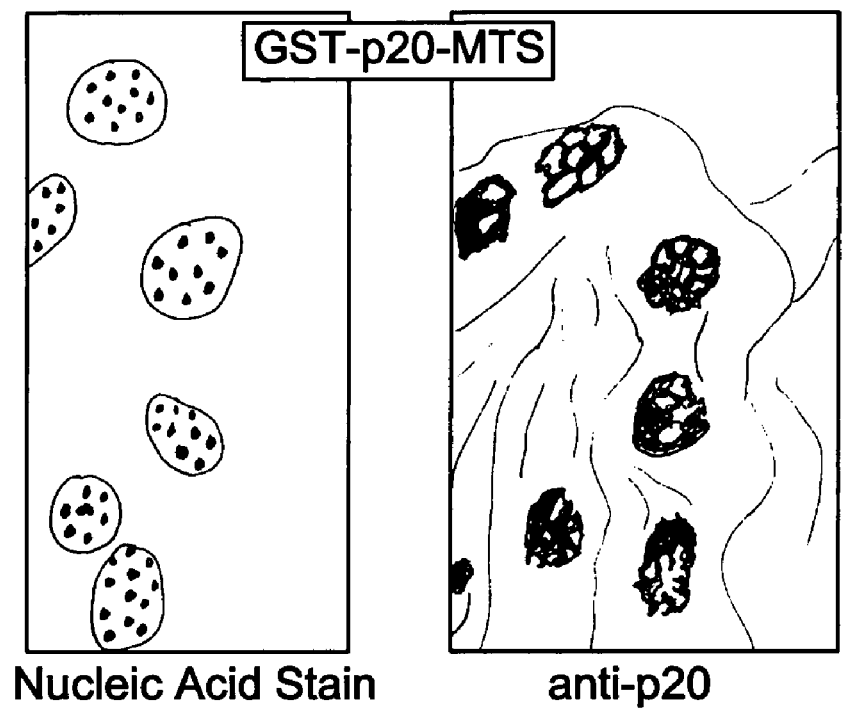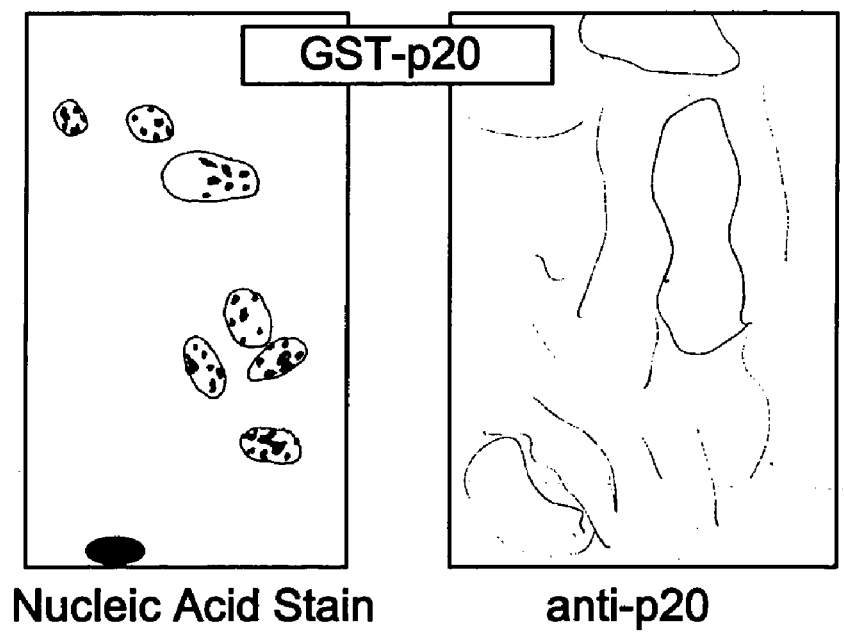
FIG. 14

TREATMENT OF INFLAMMATION WITH P20

RIGHT OF PRIORITY UNDER 37 U.S.C. § 119(e)

The present application claims right of priority under 37 U.S.C. § 119(e) to the benefit of the earlier filing date for U.S. Provisional Application "Treatment of Inflammation with p20", Ser. No. 60/183,584, filed Feb. 18, 2000.

BACKGROUND OF THE INVENTION

1. Field of the Invention

The present invention relates generally to inflammation and, more particularly, to treating inflammation, regulating cytokines, and kits therefor.

2. Description of the Prior Art

Inflammation is a normal part of the response to injuries, invasion by pathogens, and may occur without known cause. The inflammatory process can protect an organism by eliminating pathogens or by removing injured tissue and promoting the restoration of new tissue. However, overabundant or persistent inflammation results in the malfunction or the destruction of vital cells and tissues. Dysregulated inflammation is a hallmark of many painful and life threatening diseases and can affect every tissue and organ of the body.

Persistent or chronic inflammation is often characterized by increased production of pro-inflammatory mediators including cytokines, such as, interleukin 6 (IL-6) and interleukin 8 (IL-8). The stimulated expression of IL-6 and IL-8 is thought to be regulated primarily through increased transcription. Therefore, the promoter regions of IL-6 and IL-8 have been examined to determine which transcription factors activate expression. Two transcription factors are identified as being critical for maximal IL-6 and IL-8 expression: nuclear factor-κB (NF-κB) and CCAAT/Enhancer Binding Protein (C/EBP). C/EBP is actually a group or family of transcription factors related by sequence, structure, and/or biological activity. It has been demonstrated that one member of the C/EBP family, C/EBPβ, can form a complex with NF-κB and DNA motifs on the promoter(s) of a target gene leading to a synergistic activation of transcription (including the IL-1β, IL-6, and IL-8 genes among others, see, e.g., Stein et al., Molecular Cell Biol. (1993) 13:3964–3974; Lee et al., Molecular Cell Biol. (1996) 16:4257–4263; Kunsch et al., (1994) J. Immunol. 153:153–164; and Poli (1998) J Biol. Chem. 273(45):29279–29282).

C/EBPβ and Isoforms thereof

In human, murine, and rat cells, three isoforms of C/EBPβ are observed and are referred to as C/EBPβ-1, C/EBPβ-2, and C/EBPβ-3 (in order from longest to shortest). The three isoforms correlate to three in frame open reading frames (ORFs) in the C/EBPβ gene. The shortest C/EBPβ isoform, C/EBPβ-3, is referred to herein as p20 (a protein of approximately 20 kDa molecular weight).

The transcription of a recombinant C/EBPβ responsive reporter gene was found to be activated by transfection of a C/EBPβ-2 expressing gene and inhibited by co-transfection of a p20 gene in cultured cells (Descombes et al. (1991) Cell 67:569–579).

U.S. Pat. No. 5,804,445 describes an isolated 8.8 kDa tryptic fragment of C/EBPβ with mutations in the N-terminus of the fragment which make the N-terminus of the fragment less negative. The mutated tryptic fragment has a higher binding affinity for purified DNA containing a C/EBPβ binding site compared to similar fragments with the wild-type sequence.

U.S. Pat. No. 5,874,209 describes a peptide consisting of amino acids 75 to 125 of C/EBPβ, wherein residue 105 is mutated from serine to alanine to prevent phosphorylation of the 105 residue. The 105 mutated peptide competes with native C/EBPβ in cultured cells to inhibit transactivation of a reporter gene.

The Effects of Dysregulated Inflammation

Virtually all diseases of the lungs have an inflammatory component. Disorders such as idiopathic pulmonary fibrosis (IPF), adult respiratory distress syndrome (ARDS), cystic fibrosis (CF) and asthma, in particular, are characterized by over exuberant or persistent lung inflammation. In addition, overabundant or chronic inflammation is a component of many other diseases and often leads to the destruction of vital cells, tissues, and organs (e.g., the digestive tract organs and the heart and blood vessels). Currently, nonspecific suppression of inflammation with high doses of corticosteroids is used to treat these disorders. However, high dose corticosteroid therapy is itself dangerous with numerous deleterious side effects. There remains a need for the development of specific inhibitors of inflammation, treatments for inflammation and conditions associated with inflammation, regulators of inflammation stimulating cytokines, and kits associated therewith.

SUMMARY OF THE INVENTION

The inventors have discovered that an increase in the expression of p20 is a normal mechanism for the resolution of an inflammatory response. Also, the inventors have discovered that a deficient induction of p20 expression correlates with conditions of chronic inflammation including expression of inflammatory mediators following a stimulus. Furthermore, the inventors demonstrate that administration of p20 treats inflammation and related disorders in humans and other mammals or in cells derived therefrom.

In certain embodiments of the present invention, the production of p20 expression is suboptimal in patients with inflammation associated disorders and the resolution of inflammation is enhanced by administering p20. Certain embodiments provide a method of treating a disease caused or exacerbated by increased activity of indicators associated with inflammation (e.g., cytokines or prostanoids) by administering p20 to a cell or tissue of a mammal in need of treatment. Certain embodiments provide a method of treating a disease characterized by a deficient resolution phase of the inflammatory response by administering p20. The resolution phase of the inflammatory response relates to any resolution of inflammation including, for example, after a stimulus or from chronic inflammation.

Inflammation is associated with numerous disorders including, but not limited to: adult respiratory distress syndrome (ARDS), allergic rhinitis, arthritis, asthma, bronchitis, bronchopulminary dysplasia, cystic fibrosis (CF), extensive allergic alveolitis, idiopathic pulmonary fibrosis (IPF), inflammatory bowel disease, interstitial lung disease, heart disease, diseases of the nerves, and respiratory viral infection.

In one example, CF is associated with chronic or unresolved inflammation (see, e.g., FIG. 6A). The present inventors discovered that the expression of p20 was suboptimal in cells from CF patients (see, e.g., FIG. 6B). The reduced induction of p20 expression was also discovered to correlate with a prolonged inflammatory response in these cell types compared to normal controls.

It is a general object of the present invention to provide a novel class of anti-inflammatory therapeutics including p20 and methods of use thereof.

Accordingly, methods and compositions are provided for increasing an activity of p20 for treating inflammation in a subject in need thereof. The preferred subject is a mammal and the exemplary mammal is a human. The preferred method of increasing the activity of p20 in the mammal is by administering a therapeutically effective amount of p20 to the mammal.

In certain embodiments of the present invention, a therapeutically effective amount of p20 can be provided to the mammal by administering, for example, an isolated or purified p20 polypeptide or an isolated p20 expression vector to a cell of the mammal. It is preferred that treating the inflammatory response comprises inhibiting, attenuating, or terminating the response or symptom of the response.

Thus, as used herein, administering a p20 to a mammal, in one example, can refer to administering an isolated or purified p20 polypeptide to a cell of the mammal or, in another example, it can refer to administering an isolated nucleic acid capable of expressing a p20 polypeptide (e.g., a p20 expression vector) in a cell of the mammal. Alternatively the p20 (polypeptide or nucleic acid encoding and capable of expression the polypeptide) is administered to a mammal compatible cell or carrier which is administered to the mammal.

Certain embodiments of the present invention provide, a method of treating a disease caused or exacerbated by increased inflammation, or a deficiency in the resolution of inflammation, in a patient in need thereof, comprising administering an effective amount of p20 to the patient.

Certain embodiments of the present invention provide, a method of treating a disease caused or exacerbated by increased cytokine activity in a patient in need thereof, comprising administering an effective amount of p20 to the patient. In certain embodiments thereof, the cytokine is IL-1, IL-1β, IL-6, TNFα, or IL-8. Increased activity of other pro-inflammatory mediators is treated in certain embodiments wherein the inflammatory mediators include (not limiting): prostanoids and growth factors (e.g., thromboxane, TGFβ, and fibroblast growth factor, FGF).

In certain embodiments, the p20 is mixed with a pharmaceutically acceptable carrier including any carrier known or discovered that is compatible with p20 or expression of p20 by the nucleic acid as administered to the mammal. A highly preferred pharmaceutical carrier is a liposome. The liposome is useful for the administration of both p20 polypeptide and p20 encoding nucleic acid to the cell.

The inflammatory response can be in any body component of the mammal, including any cell, tissue, or organ. Preferred body components include, but are not limited to: adipose, bladder, bone, brain, breast, central nervous system, cartilage, eye, fallopian tube, heart, intestine, joint, kidney, liver, lung, lymphoid, muscle, pancreas, paratenium, peripheral nervous system, skin, spleen, stomach, synovial space, tendon, upper respiratory tract, uterus, and vasculature. Any known or discovered route of administration that is compatible with the p20 and the mammal can be used for the administration of p20 to the mammal. Preferred routes of administration include, but are not limited to: buccal, by catheter, dermal, by inhalation, by injection, intradermal, intramuscular, intraocular, intraotic, intraperitoneal, intratumoral, intravenous, nasal, rectal, topical, or vaginal. Furthermore, the inflammatory response of any disease with a known or discovered inflammatory component can be treated with p20 in light of the present disclosure. Preferred diseases for treatment (and with a known inflammatory component) include, but are not limited to: adult respiratory distress syndrome, allergic rhinitis, arthritis, asthma, bronchitis, bronchopulminary dysplasia, cystic fibrosis, extensive allergic alveolitis, heart disease, idiopathic pulmonary fibrosis, inflammatory bowel disease, interstitial lung disease, and respiratory viral infection.

Inflammation of the lung is treated in certain embodiments of the present invention. A preferred route of administration to the lung is by aerosolization of the p20 (e.g., isolated or purified p20 polypeptide and/or isolated p20 expression vector) and introduction to the lung by inhalation of the p20 aerosol. In this case, aerosolization of a p20 liposome pharmaceutical composition is highly preferred. However, aerosolization and liposome carriers may be used in other embodiments. For example, p20 liposomes may be administered by injection or by catheter and aerosols may be administered to the eye or the nasal cavities. Highly preferred diseases for treating the inflammatory component thereof are adult respiratory distress syndrome (ARDS), asthma, cystic fibrosis (CF), and idiopathic pulmonary fibrosis (IPF); each of which is known to involve inflammation of the lung.

The preferred p20 polypeptide is set forth in SEQ ID NO:7. Alternative p20 polypeptides include conservatively modified variants of SEQ ID NO:7 and biologically functional equivalents of p20 polypeptide. A useful biologically functional equivalent of the human p20 polypeptide is a mouse p20 polypeptide (approximately positions 152 to 296 in SEQ ID NO:9). The preferred p20 polynucleotide sequence is set forth in SEQ ID NO:4. Alternative p20 polynucleotides include conservatively modified variants of SEQ ID NO:4 and biologically functional equivalents of p20 polynucleotide. In certain preferred embodiments p20 polypeptide includes the peptide sequence KKTVDKHSDEYKIRRER (SEQ ID NO:15) or the encoding polynucleotide (from about nucleotide 196 to about 246 in SEQ ID NO:4). Without being bound to mechanism, the KKTVDKHSDEYKIRRER polypeptide (SEQ ID NO:15) is believed to be a bipartite nuclear localization signal which facilitates nuclear import of the p20 polypeptide (or p20 polypeptide expressed from an introduced nucleic acid) from the cytoplasmic compartment into the nuclear compartment of the cell. It is in the nuclear compartment that p20 is believed to be active; thus, certain preferred p20 polypeptides (and encoding nucleic acids) contain the KKTVDKHSDEYKIRRER peptide sequence (SEQ ID NO:15). A second predicted nuclear localization sequence in p20 has a polypeptide sequence of RRERNNIAVRKARDKAK (SEQ ID NO:16) and may facilitate nuclear transport also. Thus, in certain preferred embodiments, the p20 polypeptide (or encoding nucleic acid) includes (or encodes) the RRERNNIAVRKARDKAK sequence (SEQ ID NO:16).

In certain preferred embodiments the p20 is included in a fusion protein or encoded in a fusion gene. A preferred fusion protein (or encoding nucleic acid) includes a membrane transport sequence (MTS). Examples of a membrane transport sequence are provided in SEQ ID NO:12 and SEQ ID NO:13. Conservatively modified variants of SEQ ID NO:12 and SEQ ID:13 may be used in the alternative. Also, biologically functional equivalents of an MTS are useful. The identification and construction of an MTS are described in U.S. Pat. No. 5,807,746 to Lin et al., incorporated herein by reference.

The administration of a nucleic acid for the expression of p20 in the mammal, can be carried out ex vivo. Typically, in an ex vivo procedure, a cell is removed from the mammal, cultured, transfected with the p20 expressible nucleic acid, and returned to the mammal for the expression of the p20 in the mammal. Alternatively, the nucleic acid can be transferred to a mammal compatible acceptor (such as a mammal compatible cell from another organism, a polymer, fine porous ceramic vessels, or a bioreactor) outside of the mammal and then introduced into the mammal for the expression of p20 in the mammal. In the expression of p20 from a nucleic acid, it is preferred that the nucleic acid is administered to the mammal in vivo. A p20 polypeptide can also be administered ex vivo. An MTS-p20 fusion polypeptide is a preferred polypeptide for use therewith.

A preferred nucleic acid for expressing p20 includes a segment encoding p20. The preferred sequence for the segment is set forth in SEQ ID NO:4 which is the human polynucleotide sequence for p20. Alternative segments include conservatively modified variants of SEQ ID NO:4 and biologically functional equivalents of the human p20 polynucleotide. A biologically functional equivalent of human p20 polynucleotide is a mouse p20 polynucleotide (approximately positions 560 to 998 in SEQ ID NO:8). In general, the nucleic acid will include a non-coding region in addition to the p20 encoding segment. It is preferred that the non-coding region, and in certain embodiments, the coding region include expression control elements. It is preferred that the expression control elements are linked operably to the p20 encoding segment. The expression control elements are designed to provide appropriate gene expression of the p20 inside the mammalian cell and the use of such elements is known in the art.

In certain embodiments, the p20 polynucleotide sequence includes a segment that hybridizes to SEQ ID NO:4, or the complement of SEQ ID NO:4, under high stringency conditions. In certain embodiments, SEQ ID NO:4 or the complement of SEQ ID NO:4 is used as a hybridization probe. Hybridization probes are known in the art to include a detectable label, such as, a radiolabel, fluorescent label, calorimetric label, etc.

In certain preferred embodiments, the nucleic acid includes an expression vector and an insert, wherein at least a portion of the insert includes the polynucleotide for human p20 (SEQ ID:4). Alternatively, the insert can include conservatively modified variants or biologically functional equivalents of p20. It is preferred that the insert is linked operatively to the expression vector and that the nucleic acid contain at least one genetic control element. The genetic control element can include, but is not limited to: a promoter, a terminator, enhancer, and a polyadenylation signal. If desired, genetic control elements can be included for the temporal or tissue specific regulation of p20 gene expression. Also if desired, genetic expression systems are known in the art for the regulation of gene expression by the administration of an exogenous activating agent.

The preferred method for administering the nucleic acid is by mixing it with a pharmaceutically acceptable liposome. It is further preferred that the p20 liposome mixture is aerosolized and that the administration include inhalation of the aerosol. This method is preferred for certain embodiments for treating inflammation by inhibiting the inflammation in a human lung, wherein the lung inflammation is a symptom of a lung disease, and wherein the nucleic acid is capable of and expresses the p20 in the human lung cells. The preferred lung diseases for such treatment include, but are not limited to: adult respiratory distress syndrome (ARDS), asthma, cystic fibrosis (CF), and idiopathic pulmonary fibrosis (IPF).

BRIEF DESCRIPTION OF THE DRAWINGS

FIG. 1 is a diagram of C/EBPβ showing the relative sizes and positions of the polypeptide and polynucleotide forms of C/EBPβ-1, C/EBPβ-2, and C/EBPβ-3 isoforms of C/EBPβ and the recognition sites of the N-terminal peptide antibody and the C-terminal antibody (for a peptide sequence).

FIG. 2A is a diagram showing the National Center for Biotechnology Information (NCBI) LocusLink information for the C/EBPβ gene from human, mouse, and rat sources along with their respective gene products.

FIG. 2B is a diagram showing the LocusLink information for human C/EBPβ. As shown, the official gene symbol is "CEBPB" and the official gene name is "CCAAT/enhancer binding protein (C/EBP), beta".

FIG. 2C is a diagram showing the LocusLink information for mouse C/EBPβ.

FIG. 2D is a diagram showing the LocusLink information for rat C/EBPβ.

FIG. 3A is a diagram of an annotated human C/EBPβ nucleotide sequence (SEQ ID NO:1).

FIG. 3B is a diagram of an annotated human C/EBPβ polypeptide sequence (SEQ ID NO:5).

FIG. 3C is a diagram of an annotated mouse C/EBPβ nucleotide sequence (SEQ ID NO:8).

FIG. 3D is a diagram of an annotated mouse C/EBPβ polypeptide sequence (SEQ ID NO:9).

FIG. 3E (pages 1–2) is a diagram of an annotated rat C/EBPβ nucleotide sequence (SEQ ID NO:10).

FIG. 3F is a diagram of an annotated rat C/EBPβ polypeptide sequence provided by the present inventors (SEQ ID NO:11). The underlined "G" in FIG. 3F represents the glycine found in the inventor's C/EBPβ clone which differs from the rat C/EBPβ polypeptide previously entered into the Entrez protein database, but now withdrawn, which shows an alanine (A) at this position. In the mouse and human alignments to the rat sequence (FIGS. 5B, 5C), an alanine is found at this position. Glycine and alanine are a conservative residue substitution. It is possible that the difference is simply a polymorphism between clones.

FIG. 4A is a diagram of one possible alignment of the human and mouse C/EBPβ polypeptides (see FIGS. 3B and 3D). This particular alignment shows a 72.8% identity between the human and mouse C/EBPβ polypeptides.

FIG. 4B is a diagram of one possible alignment of the human and rat C/EBPβ polypeptides (see FIGS. 3B and 3F).

FIG. 4C is a diagram of one possible alignment of the mouse and rat C/EBPβ polypeptides (see FIGS. 3D and 3F). These polypeptides are about 99% homologous.

FIG. 5 is a diagram of an annotated human C/EBPβ-3 polypeptide showing predicted nuclear localization sequences KKTVDKHSDEYKIRR (underlined, SEQ ID NO:15) and RRERNNIAVRKARDKAK (double line overhead, SEQ ID NO:16). Nuclear localization sequences facilitate nuclear import of proteins or moieties bound to NLS containing proteins. Thus, preferred p20 sequences contain one or both NLS or encode one or both NLS.

FIG. 6A is a graph of the accumulated expression of IL-8 in the media of cultured cells BEAS, IB3, and C38 cells stimulated with TNFα (hours of incubation with TNFα). IB3 cells have the CF defect and BEAS cells are normal human bronchial epithelial cells. C38 cells carry defective genomic copies of the CF gene, but express a recombinant CFTR gene. (C38 cells are referred to as CF corrected.)

FIG. 6B is a diagram showing the accumulation of human p42 and p20 isoforms of C/EBPβ over time in BEAS, IB3, and C38 cells.

FIG. 7 is a graph showing the accumulation of IL-6 and IL-8 in the media of cultured fibroblasts derived from the lungs of patients with IPF and from normal lungs. The control data represent determinations from two different lungs and the IPF data represent determinations from three different lungs. IL-6 and IL-8 were measured by ELISA (see the Examples section) following 24 hours of stimulation with IL-1β (1 pg/ml).

Figure 10A:
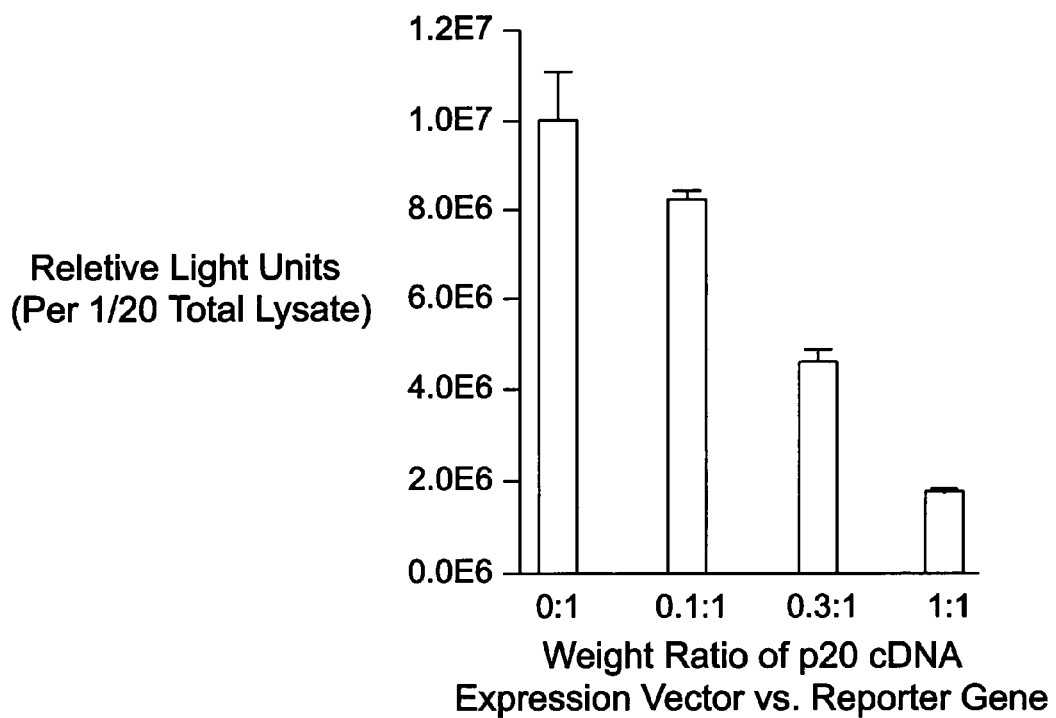

FIG. 10A is a graph showing the relative light units generated (a measure of luciferase expression) by co-transfection of various doses of a p20 expressing nucleic acid with a C/EBPβ responsive luciferase reporter expressing nucleic acid (weight ratio of p20 cDNA expression vector to luciferase reporter gene). A dose dependent regulation of the C/EBPβ responsive luciferase reporter gene by p20 is observed.

Figure 10B:
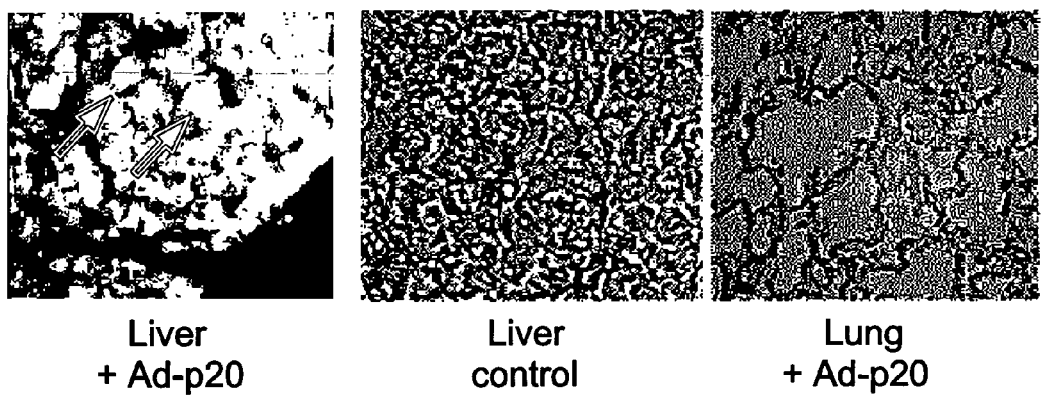

FIG. 10B shows drawing of fluorescent photomicrographs from in vivo transfection experiments with a vector including adenoviral control elements operatively linked to a p20 polynucleotide sequence. In this case, the vector further included a CMV promoter operatively linked to the p20 polynucleotide sequence, an IRES genetic control element, and a green fluorescent protein coding sequence. Transfection of the liver and lung tissue was performed by perfusion of the vector. Expression of both p20 and green fluorescent protein is observed (see left photomicrograph labeled Liver+ Ad-p20). The arrows in the figure point to individual hepatocytes with green fluorescence mainly throughout the cytoplasm.

Figure 10C:
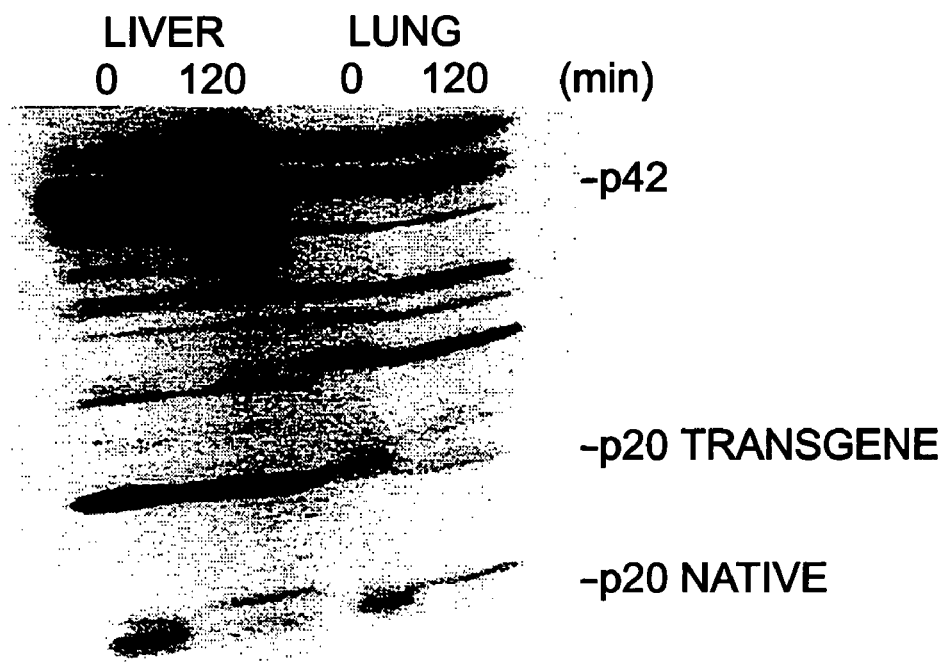

FIG. 10C is an illustration that the p20 transgene (expressed from the adenoviral p20 construct) is expressed in the liver and lung tissue in vivo. The transgenic p20 is slightly larger in apparent molecular weight (or gel migration) in these Western blots of extracted tissue samples because of the histidine tag included in the p20 nucleotide sequence for easy purification of the expression product.

Figure 10D:
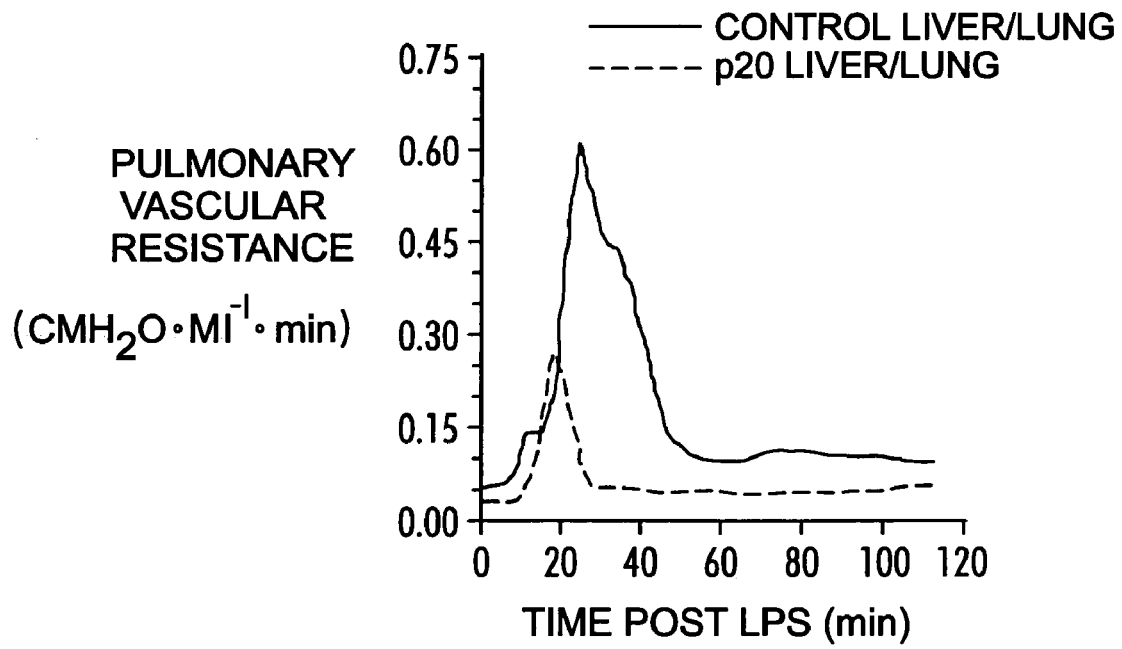

FIG. 10D is a graph showing that the pulmonary vascular resistance (PVR) response to endotoxin (an inflammatory agent) in the piglet liver and lung is dramatically reduced in tissues treated by administering a p20 expression vector compared to control tissues.

Figure 11A:
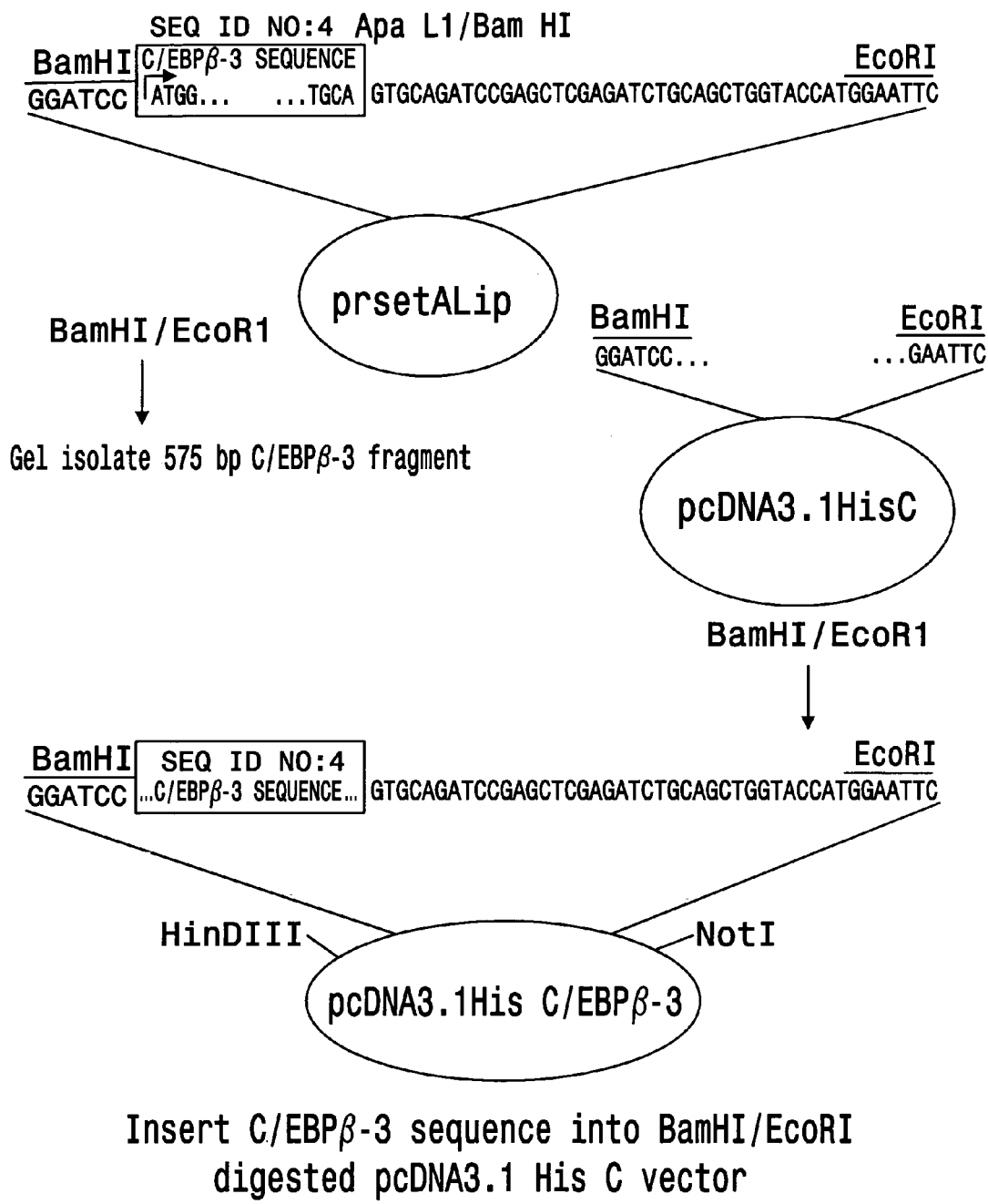

FIG. 11A is a diagram showing the construction of the pcDNA3.1HisC/EBPβ-3 vector from prsetALip which includes SEQ ID NO: 34 (GGATCC), SEQ ID NO: 4 and SEQ ID NO: 35 (GTGCAGATCCGAGCTCGAGATCTG-CAGCTGGTACCATGGAATTC) and pcDNA3.1HisC which includes SEQ ID NO: 34 (GGATCC) and SEQ ID NO: 36 (GAATTC). The resultant vector adds a polyhistidine tag to the p20 (C/EBPβ-3) polynucleotide coding sequence and includes a CMV promoter for driving p20 expression. The pcDNA3.1HisC/EBPβ-3 vector which includes SEQ ID NO: 34 (GGATCC), SEQ ID NO: 4 and SEQ ID NO: 35 (GTGCAGATCCGAGCTCGAGATCTG-CAGCTGGTACCATGGAATTC) is referred to herein as pCMV-p20-His. The vector designation pCMV-p20 is similar to pCMV-p20-His except that no histidine tag is present.

Figure 11B:
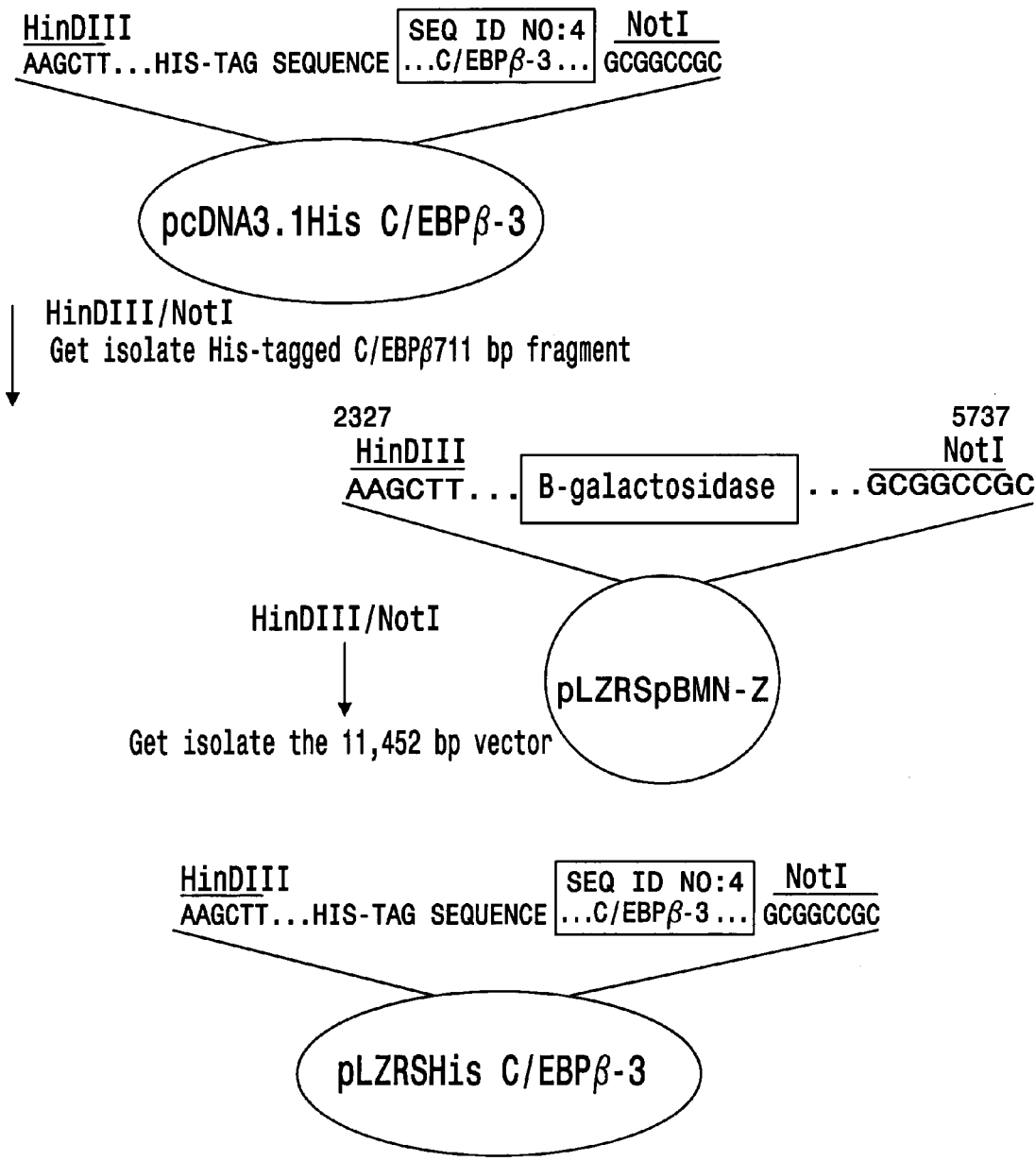

FIG. 11B is a diagram showing the construction of the pLZRShisC/EBPβ-3 vector from the pcDNA3.1HisC/EBPβ-3 vector of FIG. 10A and the pLZRSpBMN-Z hybrid retroviral/Epstein Barr viral expression vector.

Figure 11C:
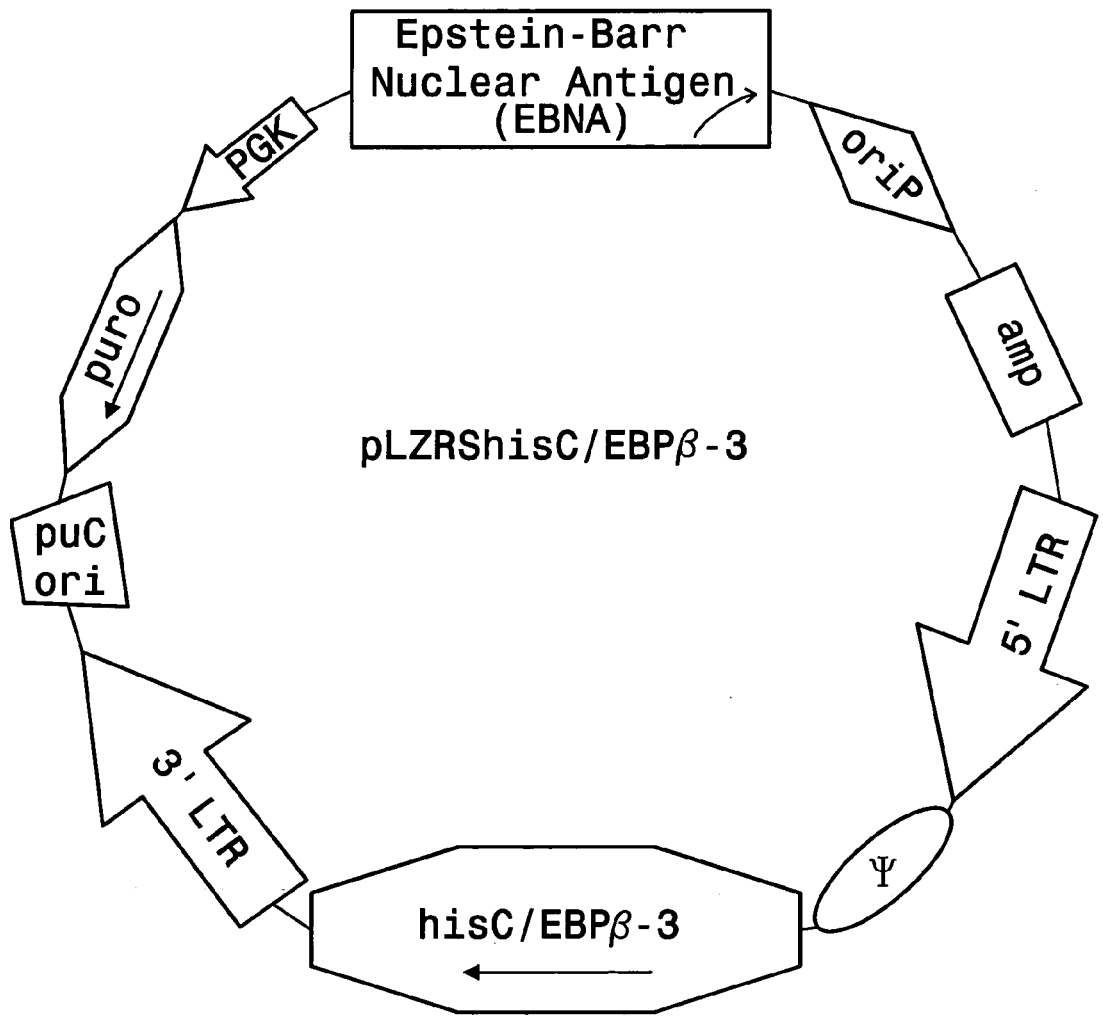

FIG. 11C is a diagram of the pLZRShisC/EBPβ-3 vector.

FIG. 11D is a diagram showing the construction of the pRSETC-NFIL6 vector (also known as the pRSETC-C/EBPβ-1 vector which includes SEQ ID NO: 40 (AGATCT-GCAGCTGGTACCATGGAATTCCATGCA), SEQ ID NO: 41 (ATGGAAGTGGCCA), SEQ ID NO: 1 and SEQ ID NO: 42 (TAGAGTCGAAGCTT)) by linking the C/EBPβ-1 coding segment of the CMV-C/EBPβ-1 vector which includes SEQ ID NO: 37 (GAATACCATGCA), SEQ ID NO: 2 and SEQ ID NO: 38 (TAGAGTCGAC) with the pRSETC vector which includes SEQ ID NO: 34 (GGATCC) and SEQ ID NO: 39 (AGATCTGCAGCTGGTACCATGGAATTC-GAAGCTT). This adds a histidine tag to the C/EBPβ-1 sequence.

FIG. 11E is a diagram showing the mutagenesis of pRSETC-C/EBPβ-1 by replacement of a portion of the vector with mutated oligonucleotides (SEQ ID NO:21 (top strand) and SEQ ID NO:22 (bottom strand)) forming the pCDNA3.1HisA-C/EBPβ-1 vector. The region of the wild type NFIL6 (CEBPB) sequence is SEQ ID NO: 33. The C/EBPβ-2 translation start site (2nd in-frame ATG, see infra) is eliminated and a perfect Kozak sequence is created around the C/EBPβ-1 translation start site (1st in-frame ATG, see infra). This step prevents production of the C/EBPβ-2 isoform and enhances production of the C/EBPβ-1 isoform from the resulting insert when placed in an appropriate expression vector.

Figure 11F:
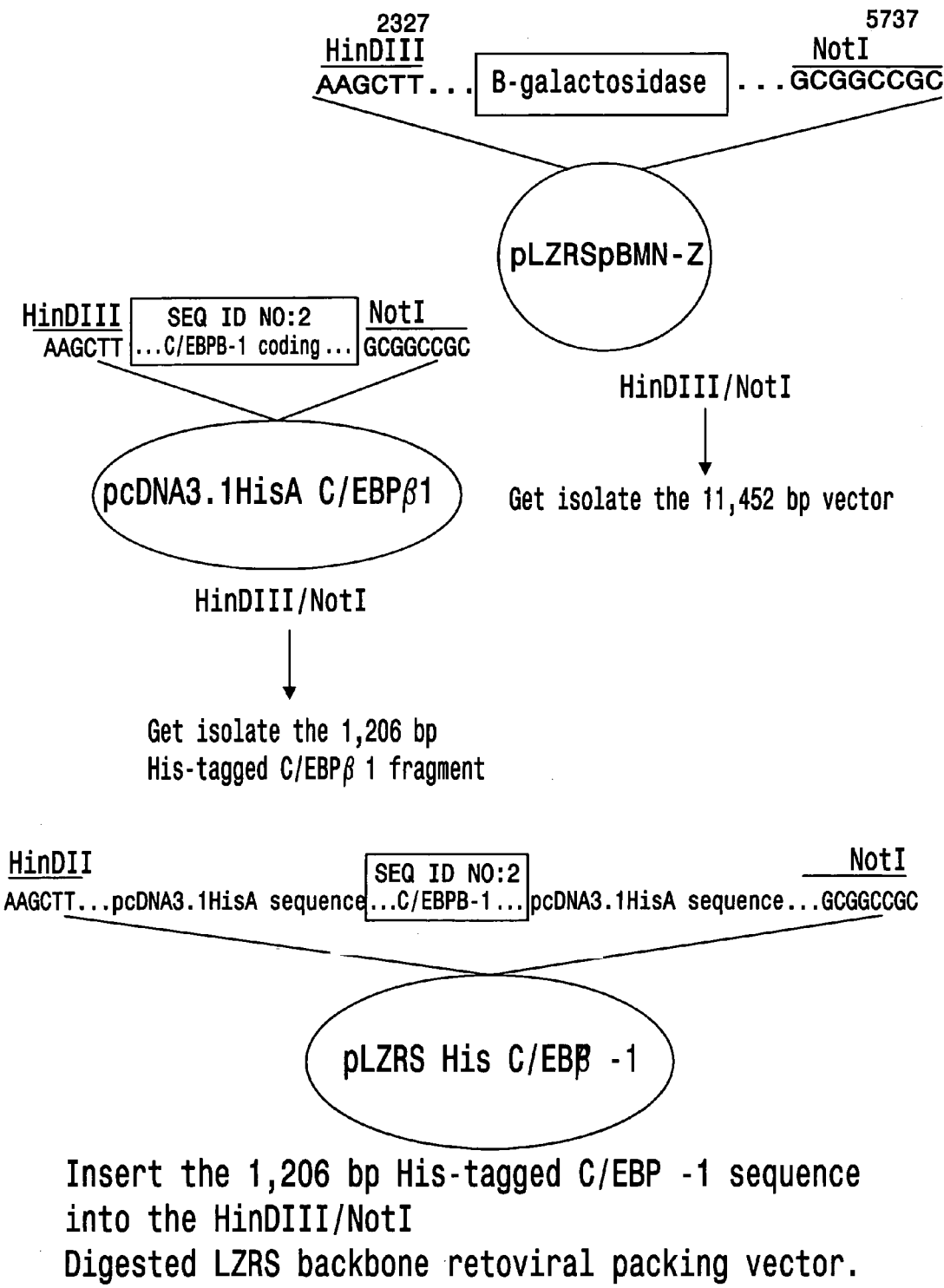

FIG. 11F is a diagram showing the transfer of the mutated polyhistidine tagged C/EBPβ-1 insert from the pCDNA3.1HisA-C/EBPβ-1 vector into the pLZRSpBMN-Z vector forming the pLZRShisC/EBPβ-1 vector. The pLZR-SpBMN-Z vector is a hybrid retroviral/Epstein Barr expression vector (described in U.S. Pat. No. 5,830,725 to Nolan et al., incorporated herein by reference). The pLZRShisC/EBPβ-1 vector expresses C/EBPβ-1 in infected mammalian cells. The pLZRShisC/EBPβ-1 vector is not capable of expressing C/EBPβ-2.

Figure 11G:
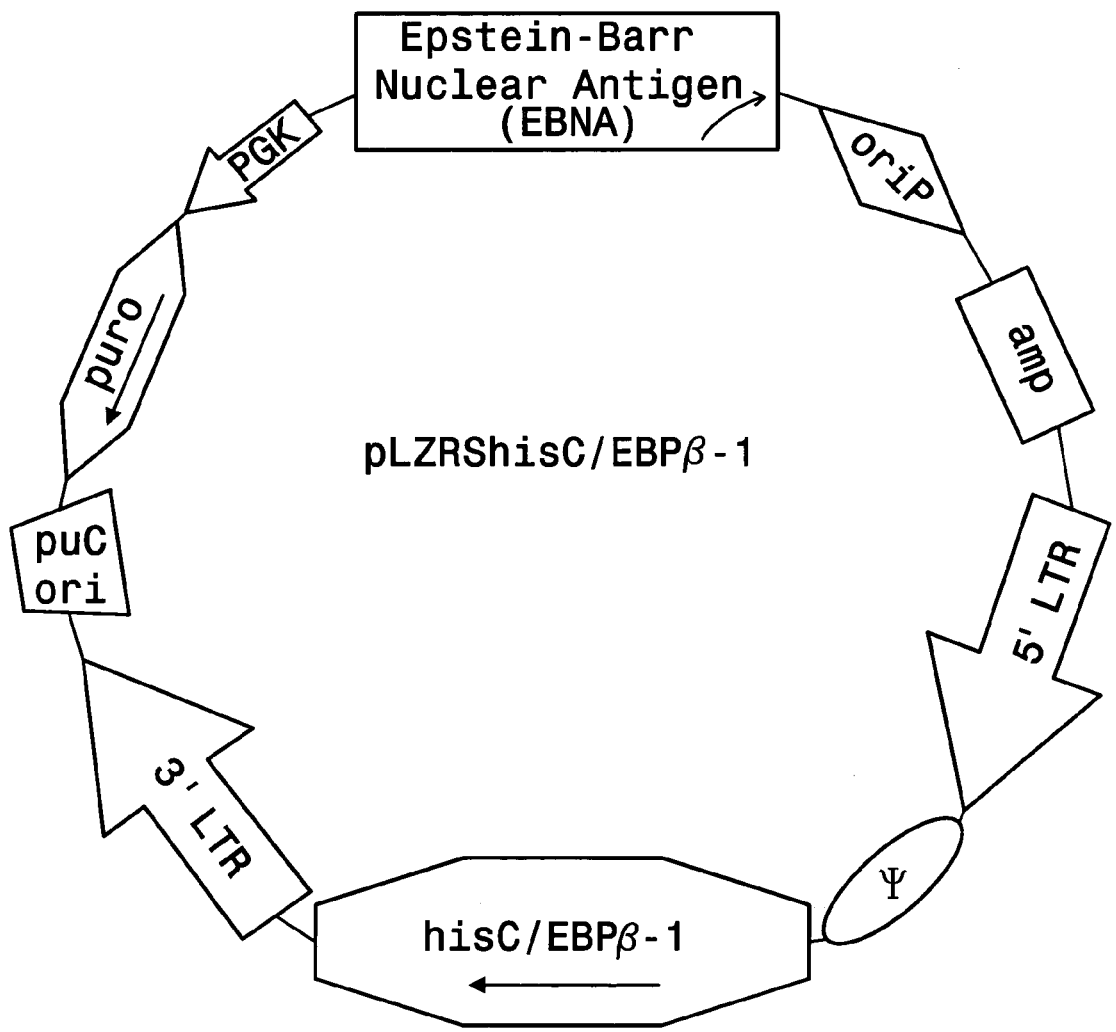

FIG. 11G is a diagram of the pLZRShisC/EBPβ-1 vector.

FIG. 12 is a diagram of the preferred human DNA codons with the order of preference from left to right adjacent to each amino acid.

Figure 13:
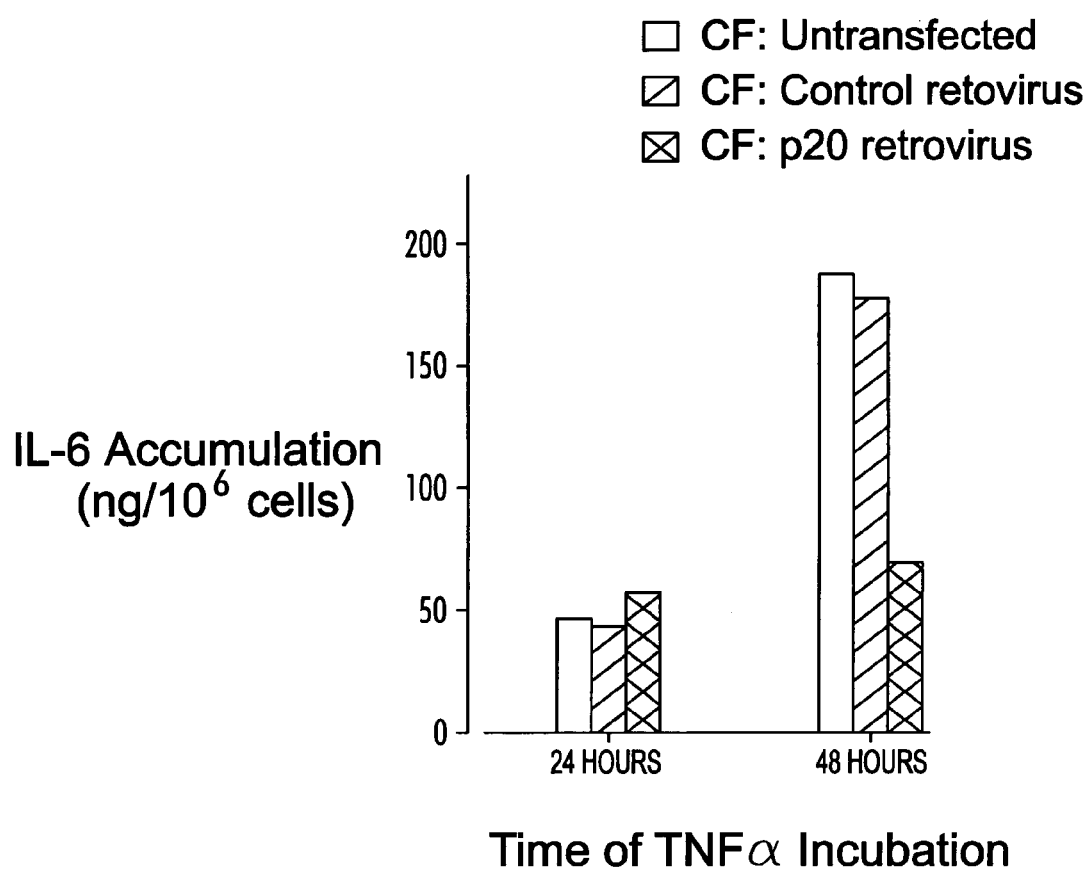

FIG. 13 is a graph which quantifies treatment by administering p20 to human cystic fibrosis (CF) bronchial epithelial airway cells (IB3 cells) which are used as an in vitro model system for analyzing the chronic inflammation of CF.

Accumulation of IL-6 (in ng/10⁶ cells) is shown at 24 hours and 48 hours (normalized to IL-6 present at 0 hours) for untreated IB3 cells (open bars), IB3 cells treated with control retrovirus (without a p20 insert, crosshatched bars), and IB3 cells treated with pLZRShisC/EBPβ-3 (p20 expressing IB3 cells, solid bars).

FIG. 14 shows the importation of MTS-p20 into the nuclei of NIH 3T3 cells by contacting the cells with the MTS-p20 as detected by fluorescent conjugated anti-p20 antibody (top right panel). The other panels show controls. The locations cell nuclei are shown in the left top and left bottom panels. The bottom right panel shows that p20 is not imported without the MTS (and without other methods of translocation of the cellular membrane).

DETAILED DESCRIPTION OF THE INVENTION

1.00 Definitions

In describing the present invention, the following terms are used. The meanings of the terms are understood by one of ordinary skill in the art and include the information provided below, which is listed by way of example so that the invention may be more easily understood.

All patents, patent publications, references, and citations listed herein are hereby incorporated in their entirety by reference and made part of this application.

No aspect, embodiment, objective, claim, or other element of the present invention is bound by theory or mechanism.

The singular forms "a," "an," and "the" include plural references in this specification, including the claims, unless the content clearly dictates otherwise.

As used herein, "isolated polynucleotide" means a polynucleotide the structure of which is not identical to that of any naturally occurring nucleic acid or to that of any fragment of a naturally occurring genomic nucleic acid spanning more than three separate genes naturally contiguous genes. The term therefore covers, for example, (a) a nucleic acid incorporated into a vector or into the genomic DNA of a prokaryote or eukaryote in a manner such that the resulting molecule is not identical to any naturally occurring vector or genomic DNA; (b) a separate molecule such as a cDNA, a genomic fragment, a fragment produced by polymerase chain reaction (PCR), or a restriction fragment; and (c) a recombinant nucleotide sequence that is part of a hybrid gene, i.e., a gene encoding a fusion protein. This definition of "isolated polynucleotide" supersedes and controls all other definitions known in the art.

As used herein, "hybridization probe" means a nucleic acid or mimetic that is labeled for detection, such as labeling with radiation (e.g., 33P, 32P, 14C, 3H labeled nucleotides), fluorescence, color, enzymatic detection, and the like. Labels and labeling systems or kits are readily available in the art. Hybridization probes (including nucleic acid mimetics, such as, peptide nucleic acids) are well known in the art.

As used herein, "culturing the cell" means providing culture conditions that are conducive to polypeptide expression. Such culturing conditions are well known in the art.

As used herein, "high stringency hybridization conditions" or "highly stringent hybridization conditions" means the following: hybridization at 42 C in the presence of 50% formamide; a first wash at 65 C with about 2×SSC containing 1% SDS; followed by a second wash at about 65 C with 0.1×SSC.

The terms "nucleotide", "nucleic acid", "nucleic acid sequence", "nucleotide sequence", "DNA", and "RNA" are known to one of ordinary skill in the art. Definitions of these terms are also found in the World Intellectual Property Organization (WIPO) Handbook on Industrial Property Information and Documentation, Standard ST.25: Standard for the Presentation of Nucleotide and Amino Acid Sequence Listings in Patent Applications (1998), including Tables 1 through 6 in Appendix 2, incorporated herein by reference. (Hereinafter "WIPO Standard ST.25 (1998)"). In certain embodiments of the present invention, the terms "nucleic acid", "nucleic acid sequence", "DNA", and "RNA" include derivatives and biologically functional equivalents. In certain embodiments of the present invention, the terms "nucleic acid", "nucleic acid sequence", "polynucleotide" and "nucleotide sequence" are used interchangeably. These terms refer to a polymer of nucleotides (dinucleotide and greater), including polymers of 2 to about 100 nucleotides in length, including polymers of about 101 to about 1,000 nucleotides in length, including polymers of about 1,001 to about 10,000 nucleotides in length, and including polymers of more than 10,000 nucleotides in length.

The terms "amino acid" and "amino acid sequence" are known to one of ordinary skill in the art. Definitions of these terms are also found in the WIPO Standard ST.25 (1998)". In certain embodiments of the present invention, the terms "amino acid" and "amino acid sequence" include derivatives, mimetics, and analogues including D- and L-amino acids which may not be specifically defined in WIPO Standard ST.25 (1998). The terms "peptide", "polypeptide", and "amino acid sequence" are used interchangeably herein and refer to any polymer of amino acids (dipeptide or greater) typically linked through peptide bonds. The terms "peptide", "polypeptide", and "amino acid sequence" include oligopeptides, protein fragments, analogues, nuteins, and the like.

An "isolated" or "purified" polypeptide or polynucleotide as used herein refers to a polypeptide or polynucleotide that has been at least partially removed from its natural environment. An "isolated p20 polypeptide" is separated to some extent from the natural milieu of proteins and factors found in a mammalian cell expressing p20. In one example, a p20 polypeptide expressed in a host cell not of mammalian origin is an isolated p20 polypeptide. An "isolated p20 polynucleotide" does not include more than three contiguous genes (including the p20) as found in native genomic DNA.

The term "fusion protein" means a polypeptide sequence that is comprised of two or more polypeptide sequences linked by a peptide bond(s). "Fusion proteins" that do not occur in nature can be generated using recombinant DNA techniques. For example, a nucleic acid encoding a membrane transport sequence (membrane transport sequence) is part of an expression insert that also includes a nucleic acid sequence encoding p20. Expression of the insert results in the production of an MTS-p20 fusion protein. This could also be called a fusion polypeptide.

A "membrane transport signal" (also known as an "importation competent signal peptide") is a sequence of amino acids generally of a length of about 10 (possibly fewer) to about 50 or more amino acid residues, many (typically about 55–60%) residues of which are hydrophobic such that they have a hydrophobic, lipid-soluble portion. The hydrophobic portion is a common, major motif of the signal peptide, and it is often a central part of the signal peptide of protein secreted from cells. The MTS peptides of this invention are "importation competent," i.e., capable of penetrating through the cell membrane from outside the cell to the interior of the cell. Specific MTS sequences are provided in U.S. Pat. No. 6,043,339 to Lin et al. and U.S. Pat. No. 5,807,746 to Lin et al., each patent incorporated herein by reference.

Meanings of the term "gene expression" are known to those with skill in the art. "Gene expression" includes the production of a polypeptides or proteins from RNA and the production of a RNA from a DNA. A gene is said to be "expressed" when it is transcribed into RNA, but this meaning also includes translation into a peptide or protein. The term "gene expression" is often shortened to "expression", "expressed", or the like. Additional meanings of the term "gene expression" are known to those with skill in the art.

The term "consensus" sequence is used herein to indicate a sequence of general agreement between multiple nucleic acid or peptide sequences that are aligned and examined for sequence similarities.

The terms "transfect", "transfection" or "transfecting" are used to indicate the act or method of introducing a molecule, usually a nucleic acid, into a cell.

The terms "treating" and "therapy" mean the reduction or elimination of symptoms of a disease of interest. This can be through alteration of physiological or molecular level abnormalities. Therapy can also refer, herein, to the reduction or elimination of signs, symptoms, or conditions of disease through unknown mechanism as the present invention is not bound by theory or mechanism. The term "treatment" can also refer to a substance or process applied to an experimental or medical condition.

The terms "disease", "disorder", and "condition" are used interchangeably herein.

With reference to an inflammation or an inflammatory response, it is understood that the terms "inhibiting", "attenuating", and "terminating" mean that the inflammatory response is decreased and/or stopped. For example, inhibiting an inflammatory response means that the severity of the response or symptoms of the response are decreased for eliminated. In another example, terminating an inflammatory response means that the response is substantially eliminated, but may or may not be completely eliminated.

Meanings of the terms used herein are known to those of ordinary skill in the art and, unless stated otherwise, can include meanings not specifically mentioned in the definitions above. Additional terms and meanings are provided herein.

2.00 Inflammation

Inflammation is a natural response of a subject to injuries, immunologic reactions, infections, altered endogenous substances, defective endogenous pathways, and foreign substances. In certain cases, the cause of inflammation is unknown. The process of inflammation typically serves to destroy, dilute, or wall off both the injurious agent and the injured cells or tissues. It is characterized in the acute form by the classical clinical signs of pain, heat, redness, swelling, and loss of function. Histologically inflammation is indicated by dilatation of arterioles, capillaries, and venules, with increased permeability and blood flow; exudation of fluids, including plasma proteins; and leukocyte migration into the inflammatory focus. Inflammation can be detected in subjects as simple as single cells. For example, expression or secretion of interleukin-6 (IL-6) and/or IL-8 into the cell medium is an indication of an inflammatory response in cultured cells.

2.01 Acute-Phase Reaction

The acute-phase reaction includes the early inflammatory response to insult or injury that consists of fever, an increase in inflammatory humoral factors, and an increased synthesis by hepatocytes of a number of proteins or glycoproteins usually found in the plasma; the reaction is typically mediated by endogenous pyrogens, the hypothalamus, adrenal hormones, cytokines, and other factors. The neutrophil is generally the predominate inflammatory cell present during the acute-phase reaction. The acute phase is followed by a maintenance phase and, in optimal conditions, resolution of the inflammation with restoration of tissue without significant damage. In less than optimal conditions, resolution may result in suppuration (formation of pus or an abscess which typically produces scarring), fibrosis (a scar characterized by a fibrin mesh, collagen, fibroblasts, macrophages, and capillaries), or chronic inflammation. Chronic inflammation can also occur without the observance of an acute phase.

2.02 Resolution Phase of Inflammation

In a normal response to an inflammatory stimulus or injury (including exposure to certain cytokines, prostanoids, and other biological factors), the cells, tissues, organs, and/or body typically attenuate the inflammation in what is called the resolution phase. Current knowledge about the resolution of inflammation is limited. Certain aspects of the present invention are that a cellular p20 expression is part of the normal mechanism for the resolution of inflammation and that deficiencies in the p20 response are associated with a prolonged or persistent inflammatory reaction and/or chronic inflammation.

2.03 Chronic Inflammation

A condition of chronic inflammation often develops when the inflammatory response is unable to eliminate the injurious agent or to repair the injured tissue to its normal physiological state. For example, when foreign particles are too large to be internalized by the neutrophil through phagocytosis, the neutrophil can be killed, spilling its enzymes and cytotoxic chemicals into the extracellular matrix, further enhancing the response including attracting additional cells, such as macrophages. In general, the tissue becomes the site of a long term inflammatory response. The primary inflammatory cells observed in sites of chronic inflammation include (non-limiting): macrophages, lymphocytes (T-cells and B-cells), cytotoxic natural killer cells, eosinophils (especially in allergic reactions), and neutrophils. Although specific terms have been associated with the inflammatory response in these sections (e.g., acute or chronic), it is clear that inflammation is a continuum; thus, these terms are not meant to be limiting.

2.10 Inflammation as a Component of Disease

The medical literature is rife with examples of inflammation (acute and chronic) being associated with painful and life-threatening diseases including, but not limited to: asthma, cystic fibrosis (CF), adult respiratory distress syndrome (ARDS), idiopathic fibrosis (IPF), Crohn's disease, viral infection, bacterial infection (including of the stomach or intestine), peptic ulcer, psoriasis, diabetes, sepsis syndrome, cirrhosis of the liver, encephalitis, allergic rhinitis. In addition, inflammation is a normal, but sometimes undesirable, component of mechanical injuries; such as a sprained ankle, surgery, or inhalation of a noxious substance. Certain diseases are described in more detail below for purposes of example and their specific mention is not meant to limit the scope of the invention.

2.11 Cystic Fibrosis (CF)

Cystic fibrosis is an inherited disease of exocrine glands, affecting most characteristically the pancreas, respiratory system, and sweat glands, usually beginning in infancy and typified by chronic respiratory infections, pancreatic insufficiency, and susceptibility to heat prostration. About 30,000 children and young adults suffer from CF in the United States and more than fifty percent of them do not live beyond their mid-thirties. Cirrhosis of the liver occurring during childhood is common and may produce portal hypertension, splenomegaly, and hypersplenism. Ten million Americans carry a defect in the cystic fibrosis transmembrane regulator (CFTR) gene which underlies CF, but are asymptomatic. The CF defect disrupts transport of sodium and chloride within epithelial cells that line various organs and leads to hallmark inflammation of the lungs and pancreas.

2.12 Asthma

Asthma is a leading cause of morbidity among children in the United States and throughout the world with about 14.9 million Americans afflicted from the disease. In addition, there is convincing evidence to suggest that its prevalence and morbidity are increasing despite a better definition of its pathogenesis and increased use of anti-asthma therapy. The reasons for this increase are not fully understood and probably multifactorial.

Our understanding of the pathogenesis of asthma has changed during the past decades, with the recognition that inflammation underlies the clinical syndrome. The degree of inflammatory changes within the lung is generally believed to be related to airway hyper-responsiveness. Analyses of endobronchial biopsies and bronchoalveolar lavage fluids have revealed that subjects with mild asthma often have evidence of inflammation within their lungs. A review of studies by the Expert Panel of the National Heart, Lung and Blood Institute National Education Program (1991) led to the conclusion that airway inflammation is present in virtually all patients with asthma. Superimposed on this chronic inflammatory state are acute inflammatory episodes triggered by several environmental factors which lead to worsening airway hyper-responsiveness and exacerbation of asthma symptoms.

2.13 Idiopathic Pulmonary Fibrosis (IPF)

IPF is characterized by alveolitis which is inflammation of the alveoli (air sacs) in the lungs. In time, the alveoli tissues and intrastitium develop fibrosis (scarring) that makes the lungs stiff and impedes gas transfer. Breathing becomes increasingly difficult and in many cases the resulting low oxygen pressure causes pulmonary hypertension (high blood pressure inside the lungs). The average survival rate after diagnosis is about five years. The cause of IPF is not known, but might involve a auto-immune reaction or an infection as the trigger for inflammation. Treatment of IPF consists of high dose corticosteroids, the efficacy of which is unproven. Lung transplantation is a last resort treatment.

2.14 Adult Respiratory Distress Syndrome (ARDS)

ARDS is the rapid onset of progressive malfunction of the lungs. It is usually observed in conjunction with multiple organ failure due to an inability to absorb oxygen. Typically, a massive inflammatory response to trauma, infection (especially sepsis), pneumonia, or shock underlies the alteration in oxygen absorption. The fatality rate in ARDS is approximately fifty percent even with assisted respiration and ARDS affects approximately 150,000 people in the United States annually. ARDS is treated with respiratory intervention and anti-inflammatory agents. Anti-inflammatory treatment consists of high dose corticosteroids, the efficacy of which is questionable.

2.15 Sepsis Syndrome

Sepsis syndrome is a systemic response to infection, characterized by hypothermia or hyperthermia, tachycardia, tachypnea, a clinically evident focus of infection or positive bacterial blood cultures, one or more end organs with either dysfunction or inadequate perfusion, cerebral dysfunction, hypoxemia, increased plasma lactate or unexplained metabolic acidosis, and oliguria. It is one of the most common causes of ARDS. While usually related to infection, it can also be associated with noninfectious insults such as trauma, burns, and pancreatitis.

2.16 Heart Disease

Information provided by the American Heart Association describes a role for chronic inflammation in heart disease (including atherosclerosis and stroke). Evidence suggests that inflammation is a indicator of risk for future heart attacks and strokes. Researchers have found that blood levels of a protein that reflects underlying levels of chronic inflammation are elevated many years before a first heart attack or stroke (Ridker et al. (1997) New England Journal of Medicine 366:973–979, incorporated herein by reference). The particular protein tested was C-reactive protein (CRP). The study found that among 1,086 apparently healthy men participating in the Physicians' Health Study, followed over an eight-year period for future development of their first myocardial infarction (heart attack), stroke or venous thrombosis (a blood clot in a vein), the men with the highest levels of C-reactive protein, compared to men with lower levels of the protein, have a threefold increase in their risk of future heart attack, have a twofold increase in their risk of future stroke. These risks were independent of other traditional risk factors for heart disease and stroke, including high cholesterol, smoking, high blood pressure and obesity.

Moreover, elevated levels of C-reactive protein were found to predict risk of first heart attacks as many as six to eight years into the future. That is enough time for affected persons to begin an aggressive program of prevention. Thus, in certain embodiments, treatment with p20 (protein, or as expressed from a p20 encoding nucleic acid) is used to lower the risks of heart attack and stroke and other diseases associated with chronic inflammation. In certain embodiments, for example, a patient with an elevated level of CRP, IL-6, IL-8, or other inflammatory indicator is treated by administering a therapeutically effective amount of p20. A therapeutically effective amount of p20 (protein or encoding nucleic acid) is an amount which lowers the level of an inflammatory indicator. Preferably, the level (or expression) of the inflammatory indicator is lowered below a level indicative of risk for heart or other disease. Measurements of the inflammatory indicator can be determined by sampling the blood or tissue and can utilize standard immunoassays and the like. The new data suggest that measurement of the body's response to inflammation may provide new means for preventing diseases related to inflammation including cardiovascular disease.

2.20 C/EBPβ and the C/EBP Family of Transcription Factors

C/EBPβ is one of six currently known members of the CCAAT/enhancer-binding protein (C/EBP) family of transcription factors which includes C/EBPα, C/EBPβ, C/EBPγ, C/EBPδ, C/EBPε, and C/EBPξ. The C/EBP family is involved in several biological activities including roles in the regulation of development, metabolism, proliferation, differentiation, and inflammation (for review, see Poli (1998) J Biol Chem 273(45):29279–29282, incorporated herein by reference). C/EBP transcription factors are modular proteins comprised of a basic domain-leucine zipper (bZIP) and a transactivation domain. The bZIP enables two compatible bZIP molecules, including various C/EBP family members, to noncovalently bind together through their leucine zipper domains into a dimeric structure. The dimeric form is then capable of noncovalently binding to specific deoxyribonucleic acid (DNA) sequences through interactions with the basic DNA binding domain of the bZIP. Higher order multimeric structures may also be possible. Upon binding to a DNA site, the transactivation domain is positioned to interact with other transcriptional machinery to stimulate, or otherwise regulate, gene expression. Additional mechanisms of action including direct protein-protein interactions are also contemplated.

2.30 Isoforms of C/EBPβ

The human, mouse, and rat C/EBPβ genes contain three open reading frames (ORFs) with in-frame ATG translation start sites which correspond to three C/EBPβ isoforms; referred to herein as C/EBPβ-1, C/EBPβ-2, and C/EBPβ-3 (see FIGS. 1, 3A, 3B, 3C, 3D, 3E, and 3F). The first ATG gives rise to C/EBPβ-1 (52 kDa in humans and 42 kDa in mice and rats). The second ATG gives rise to C/EBPβ-2 (45 kDa in humans and 36 kDa in mice and rats). The C/EBPβ-1 isoform is about 23 amino acids longer than the C/EBPβ-2 isoform in human cells and about 21 amino acids longer in mice and rats. The molecular weights are approximate as determined by SDS-PAGE and can additionally vary by phosphorylation and other modifications. The third ATG gives rise to C/EBPβ-3 (20 kDa in both humans and mice). Alternate names used for C/EBPβ-3 include p20 (in reference to a protein with approximate molecular weight of 20 kDa) and liver-enriched transcriptional inhibitor protein (LIP). The term p20 is commonly used herein and refers to the C/EBPβ-3 isoform of C/EBPβ.

As used herein, the term "C/EBPβ" means a C/EBPβ-1 isoform and/or a C/EBPβ-2 isoform. As used herein, the term "C/EBPβ" does not mean a C/EBPβ-3 isoform (p20).

3.00 Autoregulation of IL-6 and IL-8 is Defective in CF

The inventors examined the production of the pro-inflammatory mediators, IL-6 and IL-8, over time following an inflammatory stimulus of normal human bronchial epithelial cells (BEAS cells), a cell line derived from bronchial epithelial cells of a patient with CF (IB3), and a CF bronchial epithelial cell line that has been corrected with the (cystic fibrosis transmembrane conductance regulator) CFTR gene (C38 cells). Samples of each cell type were incubated in cell culture with 30 ng/ml TNFα using serum free media. At multiple time points the subsets of the cells were counted and the supernatants were assayed for IL-6 and IL-8 expression (ng cytokine/$10^6$ cells). Additional cells of each type were incubated in serum free media for determination of basal cytokine expression. For each time point, the basal cytokine concentration was subtracted from the raw TNFα stimulated concentration to determine the cumulative TNFα-stimulated IL-6 or IL-8 production (measured in units of ng/$10^6$ cells). This is the amount of IL-6 or IL-8 that accumulated in the supernatant of each cell culture normalized for basal expression.

Figure 6A:
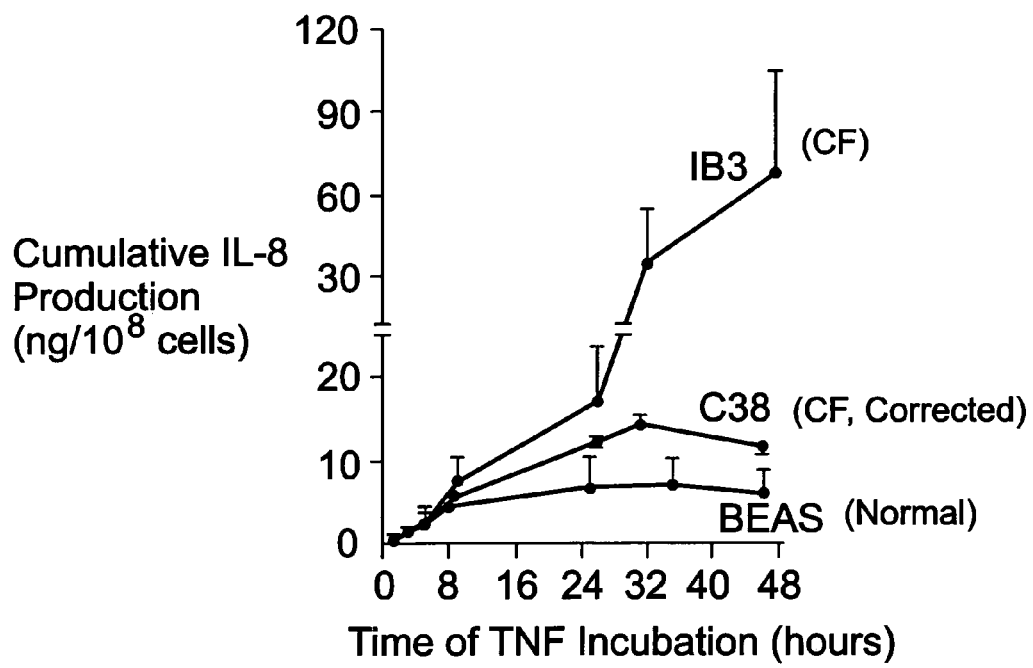

The inventors found that cells which express wild-type CFTR autoregulate IL-6 and IL-8 production so that no further generation of these cytokines occurs after a period of time despite the continued presence of the stimulating agent (FIG. 6A). In marked contrast, there was no evidence for such autoregulation in the CF cells. FIG. 6A summarizes three independent studies conducted in the three cell types and highlights the presence of an "off-switch" in the normal and the corrected CF cells and complete lack of autoregulation in the CF cells. After 24 to 32 h of TNFα there was no further increase in IL-8 accumulation in the normal or the corrected cells. In the CF cells, IL-8 continued to accumulate during the second 24 h of stimulation and the accumulation rate actually accelerated. Therefore, at the end of the 48-h period of TNFα stimulation there was on average about 7 ng of IL-8 per million normal cells (BEAS), about 14 ng IL-8/one million CF corrected cells (C38), and about 70 ng IL-8 per one million CF cells (IB3). Thus, a dysregulation of IL-8 production was observed in the CF cells, specifically a defect in down regulating IL-8 expression following an inflammatory stimulus such as TNFα administration.

A similar dysregulation of cytokine production after stimulation by an inflammatory agent (e.g., TNFα, IL-1, chronic inflammation) was discovered in the production of IL-6. The CF cells failed to turn off IL-6 generation after 24 hours of TNFα stimulation whereas the BEAS and the corrected CF cells were able to down-regulate the production of IL-6. Taken together, the inventors have found that with continued TNFα stimulation, normal cells (with normal CFTR regulation) are capable of autoregulating IL-8 and IL-6 generation and that this "off-switch" is absent or non-functional in CF cells. Furthermore, the CF cells and the expression of inflammatory mediators therefrom (e.g., IL-6 and IL-8) are a model system for CF in humans and other mammals and a model system for chronic, dysregulated, or persistent inflammation, in general, also in mammals and other humans.

3.10 Expression of p20 Correlates with Resolution of Inflammation

The inventors conducted experiments designed to determine the expression pattern of C/EBPβ in CF and corrected CF cells in addition to normal lung airway cells. The inventors incubated IB3, C38, and BEAS cells with TNFα (30 ng/ml) using serum free media conditions for 0 to 48 h and evaluated full length C/EBPβ (p42) and p20 in whole cell lysate using Western blot (known to one with skill in the art) and an antibody to the C-terminal 19 amino acids of C/EBPβ which is common to all three C/EBPβ isoforms. This antibody is commercially available from Santa Cruz.

Figure 6B:
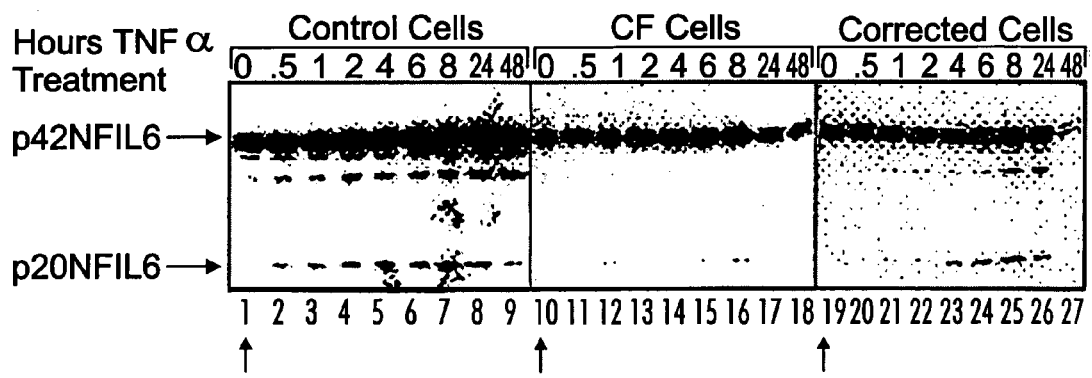

FIG. 6B shows data from this experiment. The p42 isoform was observed in all three cell types to a similar degree in the unstimulated state (lanes 1, 10, and 19). A small amount of basal p20 synthesis was observed in the BEAS and CF cells (lanes 1, 10, and 19). In contrast, the expression of p20 was dramatically increased by TNFα stimulation in the wild-type BEAS cells, peaking at 8 hours post TNFα stimulation. The stimulation of p20 expression was intermediate in the CF corrected cells and nearly nonexistent in the CF cells. Accordingly, the ratio of full-length C/EBPβ to p20 decreased with time post TNFα stimulation in the wild-type (BEAS) and CF corrected cells (C38); however, as can be seen in FIG. 6B, the ratio of full length C/EBPβ to p20 remained dramatically higher in the CF cells (IB3) compared to the BEAS and CF corrected cells.

Thus, in normal BEAS cells and the corrected CF cells, the stimulation of p20 expression and/or the decrease in the relative ratio of full-length C/EBPβ to p20 correlates with the suppression of IL-6 and IL-8 production following TNFα stimulation. However, the production of little or no p20 in CF cells and the relatively high ratio of full length C/EBPβ to p20 in the TNFα stimulated CF cells correlates with the continued production of IL-6 and IL-8 in the inflammation prone CF cells. It is believed by the present inventors that p20 functions in the autoregulation of pro-inflammatory cytokines in normal cells. Without being bound to theory or mechanism, in certain aspects of the present invention it is considered that the braking action of p20 is lost in cells in which the regulation of inflammation or the ability to resolve inflammation is reduced or is defective.

3.20 The Inflammatory Response in Normal and IPF Lung Fibroblasts

In an effort to define differences in fibroblast phenotype which might be relevant to idiopathic pulmonary fibrosis (IPF), the inventors have cultured fibroblasts from the lungs of 7 patients with IPF from either biopsy specimens or from lungs removed at the time of transplantation and from 12 normal lungs from organ donors. These cells can be maintained in primary culture for 8–10 passages and the inventors utilize stocks of cells frozen in early passage for experimentation.

Figure 7:
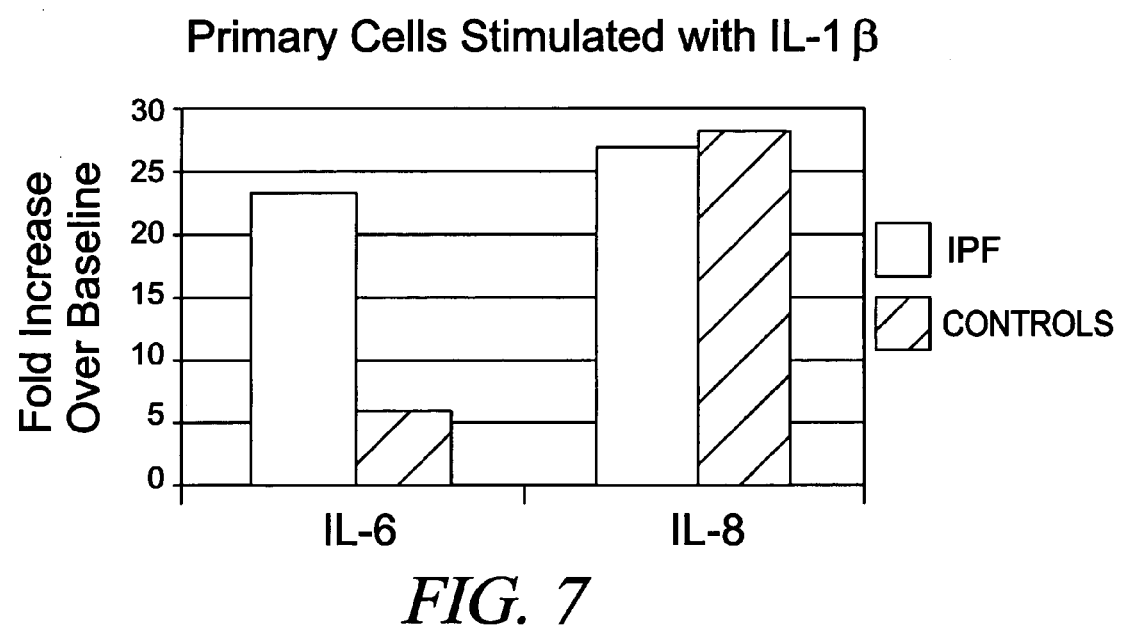

Primary cultures of two different normal lung fibroblasts and three different IPF lung fibroblasts were stimulated with IL-1β (1 pg/ml culture media) for twenty-four hours. IL-6 and IL-8 production were measured by ELISA for the IL-1β stimulated cultures and compared to identical cultures that were not stimulated with IL-1β (baseline). As shown in FIG. 7, the IPF and normal lung fibroblasts produce similar amounts of IL-8 compared to baseline when stimulated with IL-1β (reported as fold increase of IL-8 over baseline). However, the IPF fibroblasts consistently produce approximately five times more of the pro-inflammatory cytokine IL-6 when stimulated with IL-1β compared to baseline (FIG. 7).

Figure 8A:
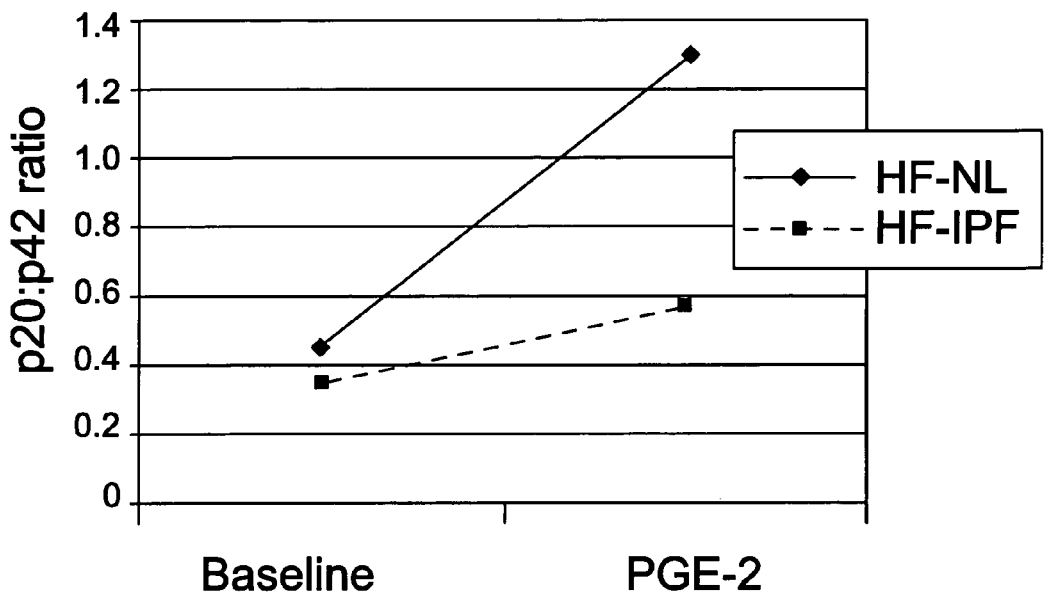
FIG. 8A is a graph showing the change in p20/p42 ratio following stimulation of normal lung fibroblasts and IPF derived fibroblasts with PGE$_2$, a well known pro-inflammatory mediator. The ratio of p20 to p42 (isoforms of C/EBPβ) dramatically increases in the normal human lung fibroblasts, but shows a relatively weak increase in the IPF fibroblasts.
Figure 8B:
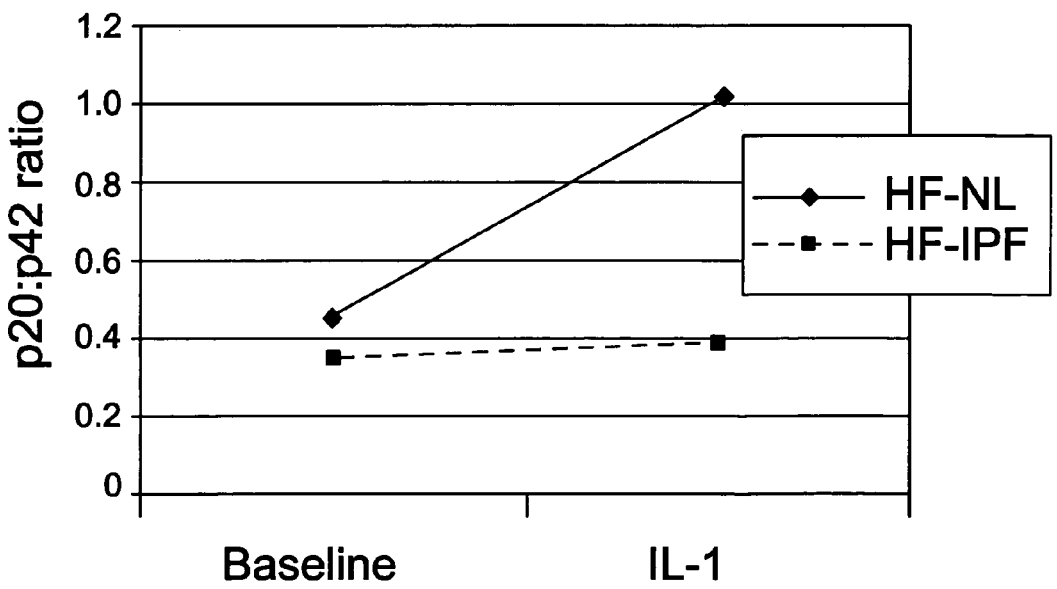
FIG. 8B is a graph showing the change in p20/p42 ratio following stimulation of normal lung fibroblasts and IPF derived fibroblasts with IL-1, also a well known pro-inflammatory mediator. The ratio of p20 to p42 (isoforms of C/EBPβ) dramatically increases in the normal human lung fibroblasts, but is essentially unchanged in the IPF fibroblasts.

Further investigation of the regulation of inflammation in IPF fibroblasts revealed that stimulation of IPF fibroblasts, this time with $PGE_2$ (1 µM) for four hours, results in a dramatic increase in the ratio of p20 to p42 in normal lung fibroblasts compared to IPF lung fibroblasts (FIG. 8A). The p20 and p42 content was determined by Western blot as described herein and the data were quantified by densitometric scanning of a autoradiograph of the Western blot. HF-NL in FIG. 8A means human fibroblasts from normal lung. HF-IPF in FIG. 8A means human fibroblasts for lung samples from patients with IPF. The increase in p20 to p42 ratio was predominately affected by the dramatic 2.5 fold increase in p20 expression observed in the normal lung fibroblasts (FIG. 8B). Essentially no increase in p20 expression was observed in the $PGE_2$ stimulated IPF fibroblasts (FIG. 8B).

Once again, the inventors have discovered that an increase in p20 expression is a normal cellular response to an inflammatory stimulus. This has been demonstrated for two different diseases herein, CF and IPF, both of which are associated with a dysregulated inflammatory response and more specifically an inability to downregulate inflammation (i.e., the resolution phase). It is an aspect of the present invention that increasing an activity of p20 in a subject will inhibit or terminate inflammation in the subject. In another aspect of the present invention, a method of preventing an inflammatory response in a subject comprises increasing an activity of a p20 in the subject. The activity of p20 can be increased, for examples, by administering p20 polypeptide or nucleic acid encoding and capable of expression p20 to cells associated with the inflammation (or distal to the inflammation, but wherein the effects of p20 administration are felt through the reduction of inflammatory factors from the cells which travel to other sites in the tissue, organ, or body).

3.30 Expression of p20 Inhibits C/EBPβ Mediated Transactivation

The inventors determined whether they could transfect cells with a construct expressing the p20 gene and whether this would inhibit C/EBPβ-dependent gene expression. The commonly used RSV promoter contains a C/EBPβ binding site and is regulated by C/EBPβ, but the CMV promoter does not contain a C/EBPβ binding site and is not regulated by C/EBPβ. The inventors co-transfected cells with an RSV-luciferase construct (pRSV-luc) and a CMV-p20 (pCMV-p20) construct and measured luciferase in cell lysates as the outcome variable. FIG. 10A shows luciferase in a series of studies in which the amount of pRSV-luc was held constant while varying the amount of pCMV-p20 (and keeping total DNA constant with irrelevant plasmid DNA). There is a clear dose-related inhibition of luciferase expression by co-transfection with the p20 expression vector (FIG. 10A). These data demonstrate that delivery of a functioning p20 gene to mammalian cells achieves inhibition of C/EBPβ related gene expression.

3.40 Treatment of an Inflammatory Response with p20

In normal cells or in a normal inflammatory response, there is an down-regulation of the expression of pro-inflammatory mediators (such as, IL-6 and IL-8) in cells or tissues which corresponds to the resolution phase of the inflammatory reaction. CF cells are characterized by a persistent inflammatory response and the data presented in FIG. 6A show that stimulated CF cells exhibit a dysfunctional autoregulation (or down-regulation) of IL-6 and IL-8 expression. Additional data in IPF fibroblasts demonstrate that these cells display a characteristic dysfunction of C/EBPβ activity with over stimulation of full length C/EBPβ (C/EBPβ-1 and/or C/EBPβ-2) production in the IPF fibroblasts in response to stimulation with $PGE_2$ and IL-1.

Furthermore, the inventors have discovered that an increase in the expression of the p20 isoform of C/EBPβ is correlated with the resolution of inflammation in normal cells, but that the increase in expression of p20 in the CF cells is dysfunctional (non-existent or nearly non-existent, see FIG. 6B). Thus, an increase in p20 expression is a characteristic of the resolution of the inflammatory response. Accordingly, the present invention provides compositions and methods for providing p20 to a subject for the inhibition of an inflammatory response and/or the suppression of inflammation related factors (e.g., IL-6 and IL-8 cytokine production).

The inventors determined that expression of p20 in vivo, results in a decrease in inflammatory indicators. The inventors injected an adenoviral vector containing a CMV promoter driven p20 gene and a CMV driven fluorescent green protein gene (GFP) intravenously into a piglet. In this embodiment, the vector included adenoviral genetic control elements, two CMV promoters, a p20 gene sequence, a fluorescent green protein gene sequence, and an IRES genetic control element. An IRES is an "internal ribosome entry site" and is used to drive expression of multiple genes from a single transcript vector (STV).

After 72 hours, a liver-lung in situ preparation was made with the animal using standard techniques. The inventors took baseline blood and lung and liver tissue samples. While continuously monitoring perfusion flow rate and lung inflow and outflow pressures (in order to calculate pulmonary vascular resistance), 25 ug endotoxin was added to the perfusate reservoir monitoring was continued for 2 hours; several perfusate samples were taken over this period for measurement of cytokines and prostanoids. Additional tissue samples of liver and lung were also taken at the conclusion of the experiment.

FIG. 10B shows fluorescent photomicrographs of control piglet liver and liver and lung tissue from the transfected animal at the time of the perfusion experiment. There was extensive green fluorescence in liver tissue (left panel, FIG. 10B), including in hepatocytes, but essentially no fluorescence was detected in the lungs (right panel, FIG. 10B). No specific fluorescence was observed in control untransfected liver (middle panel, FIG. 10B).

That the transgenes were expressed predominantly in the liver is also illustrated a Western blot of samples extracted from tissues taken 72 hours after endotoxin perfusion (FIG. 10C). The slightly larger size of the transgene generated p20 compared to native p20 is probably because the transgene includes a histidine tag for purification the expression product. Tissue samples were also taken before (0 time) and 2 hours after (120 min) the addition of endotoxin to the perfusion The transgene generated p20 is detected predominantly in the liver. Endogenous p20 decreased following endotoxin treatment in both liver and lung (this is probably part of the pathology associated with a response to endotoxin). Transgene generated p20 is exuberantly expressed in the liver at baseline and after endotoxin as would be expected.

FIG. 10D shows the pulmonary vascular resistance (PVR) response to endotoxin in the transfected animal compared to the response in untransfected animals. The upper line is from control studies in which only endotoxin was given. The lower line is the response in a pig 72 hours after intravenous delivery of an adenoviral vector containing a p20 transgene driven by a CMV promoter. This is the same p20 expression vector and animal from which the tissue for FIGS. 10B and 10C were obtained. The endotoxin-induced PVR response was dramatically attenuated in the p20 transfected animals. Thus, administration of p20 to the animal resulted in a reduction in the inflammatory response observed to an inflammatory agent.

Human cystic fibrosis (CF) bronchial epithelial airway cells (IB3 cells) are used as an in vitro model system for analyzing the chronic inflammation of CF and identifying and quantifying treatments for such inflammation. Indicators of inflammation were analyzed following stimulation of CF cells with TNFα (approximately 30 ng/ml of culture medium) at 0, hours, 24 hours and 48 hours post-stimulation. The IB3 cells were in one of the following groups: untransfected controls, infected with control retrovirus (e.g., pLZRS), and IB3 infected with high titer pLZRShisC/EBPβ-3 (for p20 expression) virus (approximately $2 \times 10^6$ (infectious units). As shown in FIG. 13, the p20 expressing IB3 cells show an ability to resolve the inflammatory stimulation of the TNFα by 48 hours. This is similar to the case for normal cells. The control cells (untransfected and control retrovirus) show an inability to resolve the inflammatory stimulation (see FIG. 13). Thus, administering p20 to CF cells and other cells with a defective or reduced inflammation resolving capacity is a method of treating the inflammation thereof.

Without being bound to this mechanism, it is contemplated that one pathway through which p20 inhibits the inflammatory response is by competing with C/EBPβ (C/EBPβ-1 and/or C/EBPβ-2) for binding to the C/EBPβ promoter element in the IL-6 and IL-8 genes. In this case, the ratio of C/EBPβ (C/EBPβ-1 and/or C/EBPβ-2) to p20 (C/EBPβ-3) is considered to be important to the balance of regulatory power for IL-6 and IL-8 expression. When the ratio of C/EBPβ to p20 is high, the cell will express greater amounts of the pro-inflammatory cytokines IL-6 and IL-8. When the ratio of full length C/EBPβ to p20 is lower, the cell will express reduced amounts of these pro-inflammatory cytokines. Another pathway through which p20 is contemplated to inhibit the inflammatory response (again without being bound by mechanism) is by disrupting protein to protein interactions between full length C/EBPβ and NF-κB, especially in the relation to the synergistically activating promoter elements for C/EBPβ and NF-κB in the IL-6 and/or IL-8 genes.

In certain embodiments, p20 based therapy is used in the treatment of an inflammatory response in a subject in need thereof. In certain preferred embodiments, p20 based therapy is used in the treatment of cystic fibrosis (CF), idiopathic pulmonary fibrosis (IPF), adult respiratory distress syndrome (ARDS), allergic rhinitis, and asthma. Each of these diseases is characterized by over-exuberant or persistent inflammation, increased amounts of the pro-inflammatory cytokines, IL-6 and IL-8 are produced, C/EBPβ is an important up-regulator of IL-6 and IL-8 expression, and nonspecific suppression of inflammation with high doses of corticosteroids has been used as therapy in each of these diseases (although the efficacy of high does corticosteroids is doubtful in IPF and ARDS).

5.00 How to Make and Use p20 as an Anti-Inflammatory Agent

In certain embodiments, the present invention provides compositions and methods for treating an inflammation in a subject in need thereof by increasing the activity of p20 in the subject by an anti-inflammatory amount.

A preferred subject for treatment is a human or other mammal (including, but not limited to: pets, horses, racehorses, show horses, livestock (cattle, sheep, goats, etc.) and competition livestock). The exemplary subject is a human. In certain embodiments the subject is a cell in culture, wherein the cell is derived from a human or other mammal. The cell can be physiologically normal with regard to inflammation or express a deficiency or defect in the resolution of inflammation (e.g., as determined by detecting or measuring inflammatory factors, such as, IL-6 and IL-8).

The preferred method for increasing the activity of the p20 in the mammal is by administering a therapeutically effective amount of the p20 to a cell of the mammal. Administering the p20 to a tissue, an organ, or body component is equivalent to administering p20 to a cell of the mammal. Such administration can be in vivo, in vitro, or ex vivo. It is preferred that p20 is combined with an excipient for administration. As used herein, the term "excipient" means the same as the phrase "pharmaceutically acceptable carrier", both terms are known in the art.

One example of a preferred method for increasing the activity of the p20 in a mammal is by administering a p20 polypeptide to a cell of the mammal. Another example of a preferred method for increasing the activity of the p20 in the subject is by administering a nucleic acid encoding p20 to a cell of the mammal wherein the nucleic acid expresses a p20 expression product in the cell of the mammal. Alternatively, the activity of p20 can be increased in a cell by administering an exogenous compound to stimulate p20 production in the cell. For example, TNFα stimulates p20 production, at least in normal cells.

Administration of p20 or a nucleic acid encoding p20 can be carried out by contacting the cell with the p20 or the nucleic acid encoding p20. In preferred examples, the p20 or nucleic acid encoding the p20 are mixed with a pharmaceutically acceptable carrier forming a pharmaceutical composition. It is preferred that administration of a pharmaceutical composition containing p20 to a cell results in the introduction of the p20 into the cell. Likewise, it is preferred that administration of a pharmaceutical composition containing a nucleic acid encoding p20 to a cell results in the introduction of the nucleic acid into the cell and expression of the p20 from the nucleic acid in the cell.

The p20 may be made using any method known to one with skill in the art for the purposes of the present invention as long as the method of production is consistent with pharmaceutical administration of the p20. Functionally equivalent and/or modified forms of p20 may be made using any method known to one with skill in the art for the purposes of the present invention as long as: the method of production is consistent with pharmaceutical administration of the equivalent and/or modified variants of p20 and at least one biological activity of the variants (inhibition of inflammation, inhibition of inflammatory mediators (TNFα, IL-1, etc.), inhibition of cytokine production (such as IL-6 or IL-8), or inhibition of clinical symptoms of inflammation) is retained such that a therapeutically effective amount of the variant can be administered. Several simple tests for determining the activity, including the anti-inflammation biological activity of p20, functional equivalents, and modified variants are described herein.

In using p20 (including functional variants) as an anti-inflammation agent, the polypeptide form of p20 may be contacted to a cell or introduced into a cell through any of a variety of manners known to those with skill in the art. In certain embodiments, the preferred method of administering p20 polypeptide is in combination with an excipient (forming a p20 pharmaceutical composition). The p20 pharmaceutical composition may be administered by any mode or route known and to any cell, tissue, or organ of the mammal.

In preferred embodiments, the production of p20 is caused in a cell by the introduction of a nucleic acid, wherein at least a portion of the nucleic acid encodes p20 or variant thereof, wherein the nucleic acid is compatible with the cellular machinery for the expression of the encoded product. Whether the p20 is supplied as a protein or encoded in a nucleic acid, it is preferred that it is combined with a pharmaceutically acceptable carrier for optimization of delivery. A number of such formulations are described herein, but any that are known in the art may be employed in light of the present disclosure.

A variety of nucleic acid expression systems and methods for their introduction into a cell are known in the art and are useful in conjunction with the present invention. In general, a nucleic acid expression system is comprised of an expression vector into which a polynucleotide insert (or inserts) can be cloned. A nucleic acid expression system may also refer to an expression vector complete with polynucleotide insert. Genetic elements are typically included in the expression vector or, in certain cases included in the insert, that drive the production or expression of the polynucleotide insert in the proper environment. The set of exogenous genetic elements for driving expression include, but are not limited to: promoters, enhancers, ribosomal binding sites, internal ribosome entry sites, polyadenylation signals, nuclear localization signals, etc. A number of these elements are described in U.S. Pat. No. 5,910,488 to Nabel et al.; incorporated herein by reference. Expression environments include in vitro expression, wherein all necessary expression factors (either purified or partially purified) are added in a mixture for the support of expression. Additional environments encompass cellular expression (in vivo expression). In embodiments described herein, the preferred expression environment is a mammalian cell.

As used herein, a "p20 nucleic acid expression system" includes an expression vector and a p20 polynucleotide insert, designed for expression of p20 in a mammalian cell. At least a portion of the p20 insert encodes a p20 polypeptide. The coding sequence may or may not be interrupted, such as with a recombinant intron. Such expression can result in the generation of p20 mRNA. Such expression also can result in the generation of p20 protein in the targeted cells.

Techniques for obtaining a p20 polynucleotide sequence and for incorporating the sequence into an appropriate expression system are known in the art (Descombes et al. (1991) Cell:569–579, incorporated herein by reference; U.S. Pat. No. 5,215,892 to Kishimoto et al., incorporated herein by reference; and U.S. Pat. No. 5,360,894 to Kishimoto et al., incorporated herein by reference). The selection of specific restriction endonucleases to cleave the expression vector and to cleave a p20 polynucleotide sequence is known to one of skill in the art and is aided by the sequence listings and FIGS. 2A–2D, 3A–3F. The cloning of a p20 polynucleotide into a vector containing a CMV promoter is described in FIG. 11. Methods for ligating the expression vector with one insert in the proper orientation for expression and methods for selection and analysis of p20 expression vector clones including sequencing of the clones by dideoxy sequencing (the Sanger method and variations thereof) are all known to one with ordinary skill in the art. Furthermore, methods for inserting multiple p20 inserts (including multiple variants) or p20 and a non-p20 expression insert into an expression vector are known in the art. In certain embodiments, an internal ribosome entry site (IRES) is used to drive expression of multiple copies of p20 from a single transcript vector (STV); as described in U.S. Pat. No. 4,937,190 to Palmenberg et al., incorporated herein by reference.

For example, RNA or DNA encoding p20 may be introduced to the cell by any manner known in the art. In certain preferred embodiments, the p20 is introduced into the cell through the introduction of a DNA segment which encodes p20. In some such embodiments, it is envisioned that the DNA segment further comprises the p20 gene operatively linked to expression control sequences. The p20 gene may be operatively linked to a suitable promoter and a suitable terminator sequence. The construction of such gene/control sequence DNA constructs is well-known within the art. In particular embodiments, the promoter is selected from the group consisting of CMV, SV40 IE, and RSV LTR. The construction and use of the CMV promoter is described in U.S. Pat. No. 5,385,839 to Stinski, incorporated herein by reference and U.S. Pat. No. 5,168,062 to Stinski, incorporated herein by reference.

In certain embodiments, the DNA segment and expression control sequences may be located on a vector, preferably an expression vector. For example, a preferred expression vector is a plasmid DNA expression vector. Another preferred vector is a viral-based expression vector. The viral vector may be, for example, a retroviral vector or an adenoviral vector, or another vial-based vector. The genetic elements of a viral derived vector may have been subsequently modified by nature or by the hand of man. Preferably, the viral-based expression vector with a p20 insert supports the expression of p20 in a mammalian cell to which the vector is introduced, especially a human cell. The term "insert" refers to the nucleic acid segment or polynucleotide incorporated into the vector for expression. Preferred inserts include nucleic acids encoding p20. The insert may include non-coding polynucleotide sequences such as restriction enzyme sites and introns. The vector may be used to deliver a p20 gene to a cell in certain gene therapy embodiments of the invention. Also, such vectors can be used to transform cultured cells, and such cultured cells could be used, inter alia, for the expression of p20 gene products in vitro and for the transfer of p20 expressing cells into a compatible mammalian host (ex vivo gene transfer).

Methods of identifying an inflammatory response or symptom of inflammation are known in the art. Such methods include observation or measurement of increased inflammatory cells (e.g., neutrophils, macrophages, lymphocytes (T-cells and B-cells), cytotoxic natural killer cells, and eosinophils) and mediators (e.g., IL-6, IL-8, and IL-1) in the organ or tissue and clinical signs and symptoms. Classic symptoms of inflammation include pain, heat, redness, swelling, and loss of function. Histologically dilatation of arterioles, capillaries, and venules, with increased permeability and blood flow is seen in inflammation. Exudation of fluids, including plasma proteins; and leukocyte migration into the inflammatory focus is also observed.

Pharmaceutical formulations for both protein and nucleic acid based therapeutics, dosage, modes and routes of administration, and methods of measuring therapeutic effectiveness are known to those with skill in the art and any of these methods and formulations may be used in conjunction with the present invention provided that they are pharmaceutically acceptable. Several of these compositions and methods are described herein.

5.01 Special Considerations for C/EBPβ-3 Expression

In certain embodiments, it is preferred that nucleic acids for the expression of p20 include the full length C/EBPβ gene sequence (e.g., SEQ ID NO:1 genomic human, SEQ ID NO:2 C/EBPβ-1 CDS). Using such compositions and methods has certain advantages including the possibility of a more natural distribution of expression (cell type and temporal) by inclusion of additional C/EBPβ genetic control elements (both known and unknown). Also, if p20 is generated by a proteolytic mechanism within the cell, then the synthesis (meaning expression) of C/EBPβ-1 from an exogenously introduced nucleic acid is contemplated to result in the production of p20 by these mechanisms. However, it is preferred that C/EBPβ-2, and optionally, C/EBPβ-1 are not expressed from the C/EBPβ encoding nucleic acid. Therefore, in certain preferred embodiments, the nucleic acid is modified to prevent a production of the C/EBPβ-2 isoform.

Possible modes of C/EBPβ-2 production include, but are not limited to: translation initiation at the C/EBPβ-2 ATG translation initiation start site, proteolytic cleavage of a more encompassing polypeptide (e.g., a C/EBPβ-1 polypeptide), RNA processing, and blockage of other translation initiation start sites (e.g., the C/EBPβ-1 AUG). Any of these modes of C/EBPβ-2 production, and others, can be blocked to prevent C/EBPβ-2 expression.

The preferred method of preventing C/EBPβ-2 isoform production from a C/EBPβ polynucleotide is by using site-directed mutagenesis to eliminate the C/EBPβ-2 translation initiation start site (located in human CEBPB at approximately positions 368–370 of SEQ ID NO:1, see FIG. 3A). It is also preferred that alternative sequences of C/EBPβ such as mouse and rat C/EBPβ are modified to eliminate the C/EBPβ-2 translation initiation start site. As a result of the elimination of the C/EBPβ-2 translation start site, C/EBPβ polynucleotides (including C/EBPβ-1) are not able to, or do not, express C/EBPβ-2 in cells into which they are introduced. These nucleic acids will express p20 and are contemplated to express C/EBPβ-1.

Optionally, it is preferred to prevent expression of both C/EBPβ-1 and C/EBPβ-2 from a C/EBPβ clone. The preferred method for preventing C/EBPβ-1 expression from a C/EBPβ clone is the same as for C/EBPβ-2; elimination of the ATG translation initiation site. These nucleic acids will express p20 only. These methods may apply to any expression of p20 (in vitro, in vivo, ex vivo, etc.)

In certain embodiments, it is preferred to enhance the expression of p20 from a nucleic acid. For example, a polynucleotide segment including p20 is mutated through site-directed mutagenesis to create a Kozak sequence at the C/EBPβ-1 translation initiation site (approximately positions 299 to 301 in SEQ ID NO:1(see FIG. 3A). The use of a Kozak sequence to enhance expression of a gene is well known in the art. In the present invention, the Kozak sequence may be used to selectively enhance the expression of one C/EBPβ isoform over another For example, p20 expression is enhanced over C/EBPβ-1 and C/EBPβ-2 expression through the use of a Kozak sequence at the p20 start site.

If undesirable proteolytic digestion of C/EBPβ-1, C/EBPβ-2, or C/EBPβ-3 (p20) is found to occur in a particular system, the protease binding site can be optionally mutated to prevent proteolysis. Significant proteolytic cleavage is not expected to arise, however. In other methods, the C/EBPβ isoform protein can be combined with a protease inhibitor, protein stabilizing agent, or stored under protein stabilizing conditions (i.e., refrigeration, freezing, desiccated, etc.).

5.02 Special Considerations for Nuclear Import

It is believed by the inventors that p20 acts in the nuclear compartment of the cell (without being bound to mechanism). Therefore, in certain preferred embodiments, compositions including a p20 sequence contain a nuclear localization sequence (NLS) to facilitate nuclear import (either peptide or encoding nucleic acid). C/EBPβ contains two putative NLS segments. Both of these segments are in the p20 portion of the C/EBPβ gene/polypeptide as determined by PSORT II an online sequence analysis tool.

The results of the PSORT II analysis tool predict that KKTVDKHSDEYKIRR (SEQ ID NO:19 and NLS A in FIG. 5) and RRERNNIAVRKSRDKAK (SEQ ID NO:20 and NLS B in FIG. 5) are nuclear localization sequences. Both of these sequences are located in the C-terminal portion of C/EBPβ reference sequence and are contained within p20. In certain embodiments of the present invention, any NLS may function to facilitate nuclear import of p20 (see e.g., Stochaj et al. (1993) J of Cell Science 104:89–95, incorporated herein by reference). A preferred NLS is RRERNNIAVRKSRDKAK (SEQ ID NO:16) and certain preferred polypeptide sequences (or encoding nucleic acids) will include this peptide sequence (or encoding nucleic acid sequence). An even more preferred NLS is KKTVDKHSDEYKIRR (SEQ ID NO:15) and certain even more preferred polypeptide sequences (or encoding nucleic acids) will include this peptide sequence (or encoding nucleic acid sequence). In certain embodiments, preferred sequences will include both NLS A and NLS B (FIG. 5). The threonine with an "*" over it in FIG. 5 and at approximately position 68 (SEQ ID NO:7) is a potential phosphorylation site that the inventors believe may enhance p20 activity. In certain preferred embodiments, polypeptides (or encoding nucleic acids) will include this threonine.

5.10 Preferred and Alternative Sequences of p20

Preferred polynucleotide and polypeptide sequences of p20 are the human reference or consensus sequences. The p20 sequence can be found in databases provided by the National Center for Biotechnology Information (NCBI) located at the United States National Library of Medicine (NLM). The NLM is physically located at 8600 Rockville Pike, Besthesda, Md. 20894; phone: 301-594-5983. One of ordinary skill in the art is able to use the identification assignments shown in FIGS. 2A–2D to determine the reference or consensus sequence for human and mouse C/EBPβ, respectively. The positions of C/EBPβ-1, C/EBPβ-2, and C/EBPβ-3 (p20) within the C/EBPβ sequence can be determined through the literature by one of ordinary skill in the art and are provided in FIGS. 3A–3F).

Figures 1, 2A:
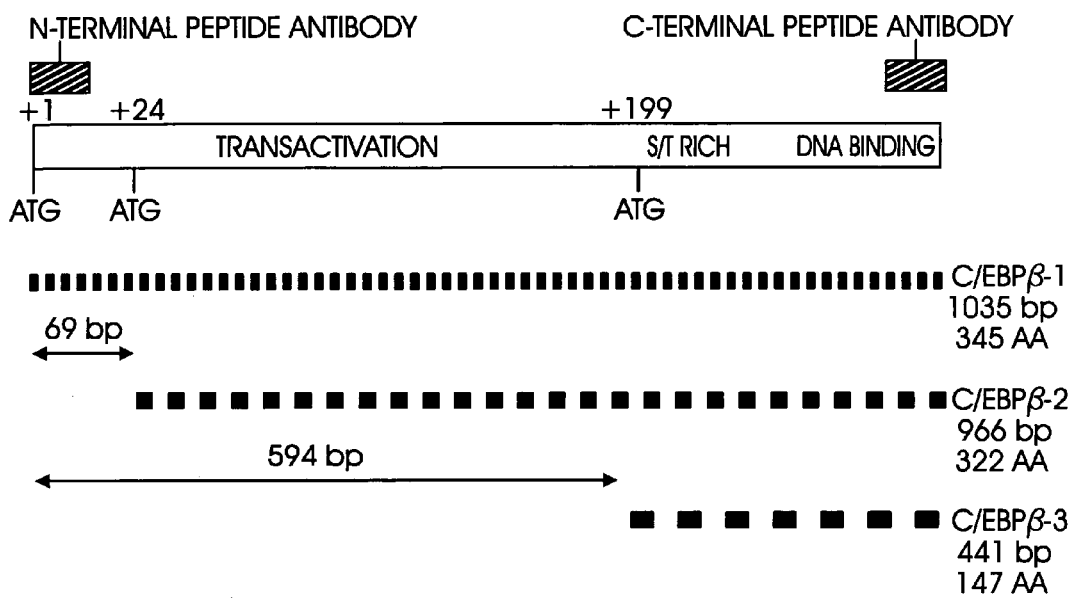

FIG. 1 provides a diagram of the genetic structure of the C/EBPβ gene and the relationship between C/EBPβ-1, C/EBPβ-2, and C/EBPβ-3 (p20) isoforms. It is believed that the expression products of the isoforms arise in the cell from a leaky ribosomal translation initiation of a single mRNA polynucleotide. However, the present invention is not bound by this mechanism of production. It is also possible that the C/EBPβ-2 and/or p20 protein isoforms arise in the cell through proteolytic cleavage of a longer polypeptide (i.e., C/EBPβ-1 or C/EBPβ-2, respectively); however, the inventors do not believe this mechanism to be correct or, at least, physiologically relevant. The mechanism is not important because it is shown herein that p20 functions as an anti-inflammatory agent. In addition, for a given population of cells, it is shown herein that p20 inhibits the production of the pro-inflammatory cytokines IL-6 and IL-8.

It is evident from FIG. 1 that C/EBPβ-1, C/EBPβ-2, and C/EBPβ-3 (p20) are all generated from the genetic material of the CEBPB locus in mammalian genomes. The genomic DNA for the C/EBPβ gene does not contain an intron; thus, the mRNA corresponds to the genomic sequence without interruption. All three isoforms of C/EBPβ have similar 3' or C-terminal ends (DNA, RNA, or protein). In humans, C/EBPβ-1 is comprised of about 345 amino acids (SEQ ID NO:5 and FIG. 3B) coded for by about 1038 nucleotides (including the TAG stop codon) (SEQ ID NO:2 and FIG. 3A). Human C/EBPβ-2 is comprised of the about 322 C-terminal amino acids (SEQ ID NO:6) coded for by the about 969 nucleotides (SEQ ID NO:3). Human C/EBPβ-3 (p20) is comprised of the about 147 C-terminal amino acids (SEQ ID NO:7) coded for by the about 444 nucleotides (SEQ ID NO:4). The human C/EBPβ isoforms are best viewed in FIGS. 1, 3A, and 3B.

A preferred p20 polynucleotide is the human p20 nucleic acid coding sequence set forth in SEQ ID NO:4 and shown in FIG. 3A. This is the "consensus" human C/EBPβ-3 polynucleotide consisting of approximately the 444 basepairs and a portion of the sequence identified by Accession Number X52560 in GenBank as annotated in FIG. 3A. The C/EBPβ-3 isoform of the CEBPB gene originates from the third in frame "ATG start codon" FIGS. 1 and 3A).

A preferred p20 polypeptide is the human p20 peptide sequence set forth in SEQ ID NO:7 and shown in FIG. 3B. Information provided by LocusLink on the C/EBPβ polypeptide is shown in FIGS. 2A–2D. The consensus p20 polypeptide can be used in the present invention. It is preferred that pharmaceutical formulations of p20 are in a purified form containing minimal amounts of C/EBPβ-1 or C/EBPβ-2. In certain embodiments, pharmaceutical formulations including partially purified p20 are preferred. Minimal amounts of C/EBPβ-1 or C/EBPβ-2 means herein that p20 is the major protein in the purified composition. In certain preferred embodiments, p20 accounts for about 51% or more of the protein in the sample Protein composition can be determined easily by SDS-PAGE and silver staining techniques as is known in the art and may include Western blot techniques for further identification. The amount of each type of protein in a lane of a silver stained gel can be measured densitometrically. In certain more preferred embodiments, p20 accounts for about 52% to about 85% of the protein in the sample; in even certain more preferred embodiments, p20 accounts for about 85% to about 95% or more of the protein in the sample; in still more preferred embodiments, p20 accounts for about 99% or more of the protein in the sample. The sample then being used to mix with a pharmaceutically acceptable carrier forming a pharmaceutical composition or formulation.

Alternative p20 sequences include the mouse p20 nucleotide sequence of approximately positions 560 to 998 of SEQ ID NO:8 (FIG. 3C) and the mouse p20 polypeptide sequence of approximately residues 152 to 196 of SEQ ID NO:9 (FIG. 3D). The mouse p20 coding sequence (CDS) is located at approximately residues 560 to 998 (including the TAG stop codon) of SEQ ID NO:8 (FIG. 3C). The basic isoform structure of the mouse CEBPB locus is similar to the human structure as shown in FIG. 1 and FIG. 4A. FIG. 4A shows one possible alignment of the human and mouse C/EBPβ polypeptides along with the start site of each C/EBPβ isoform and the C-terminal cysteine at about position 345 (human) or 296 (mouse) in the peptide sequences. In this alignment, gaps in the mouse polypeptide relative to the human polypeptide are shown as dashes and identical amino acids (residues) are shown by the star symbol "*". Non-identical amino acids are shown by a space.

5.20 Biological Functional Equivalents

In certain embodiments, it is desirable to utilize biologically functional equivalents of polypeptides and polynucleotides described herein. Preferred and alternative polynucleotide and polypeptide sequences useful for embodiments of the present invention are provided herein. Thus, it is generally not necessary to identify additional polynucleotide or polypeptide sequences to practice the present invention. However, as is known to one with skill in the art, the biological function or activity of a gene product may not correspond directly to an absolute polynucleotide or polypeptide sequence of the gene product. Therefore, the inventors specifically contemplate that alterations to sequences provided herein, including in the Sequence Listings of this Specification, may be made or used wherein the altered sequences, or methods of use thereof, are equivalent to sequences, or methods of use thereof, and are within the spirit and scope of the present invention. These equivalent sequences are referred to as biologically functional equivalents, or simply as functional equivalents. Functional equivalents can include, but are not limited to: conservatively modified variants, degeneracy of the nucleic acid code, polymorphisms, certain insertions and deletions, and certain length variants. Methods for altering sequence residues and testing the altered sequences for function or activity are known in the art or described herein. These alterations may be natural or made by the "hand of man".

At the nucleotide level, different codons can encode the same amino acid. In other words, the genetic code is degenerate (Alberts et al., Molecular Biology of the Cell, (1989) 2nd Edition, Garland Publishing, Inc., and incorporated herein by reference). The terms "wobble" and "nucleic acid degeneracy" are used herein to refer to codons that encode the same amino acid, such as the six codons for arginine or serine. FIG. 12 lists the preferred human codons. The codons are listed in decreasing order of preference from left to right in the table (Wada et al. (1990) Nuc. Acids. Res., 18:2367–2411, included herein by reference). Codon preferences for other organisms also are well known to those of skill in the art (Wada et al., 1990, supra). Thus, one with skill in the art knows that two different polynucleotides can encode identical polypeptide sequences due to codon wobble.

It is understood in the art that amino acid and nucleic acid sequences may include additional residues, such as additional N-terminal or C-terminal amino acids or 5' or 3' sequences, and yet still be essentially as set forth in one of the sequences disclosed herein; so long as the sequence meets the criteria set forth herein, including the maintenance of at least one biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes between coding regions (Alberts et al., supra, incorporated herein by reference). Thus; about 1, 2, 3, 4, 5, 6, 7, or more than 7 amino acids could be added to a polypeptide and the polypeptide may still retain at least one biological activity. Or; about 1, 2, 3, 4, 5, 6, 7, or more than 7 nucleotides could be added to a polynucleotide and expression products of the polynucleotide may still retain at least one biological activity.

It also is understood in the art that amino acid and nucleic acid residues may be removed from the N-terminal or C-terminal ends of polypeptide or 5' or 3' ends of polynucleotide sequences, and yet still be essentially as set forth in one of the sequences disclosed herein; so long as the sequence meets the criteria set forth herein, including the maintenance of at least one biological protein activity where protein expression is concerned. The removal of terminal sequences particularly applies to nucleic acid sequences that may, for example, include various non-coding sequences flanking either of the 5' or 3' portions of the coding region or may include various internal sequences, i.e., introns, which are known to occur within genes between coding regions (Alberts et al., supra, incorporated herein by reference). Thus; about 1, 2, 3, 4, 5, 6, 7, or more than 7 amino acids could be removed from a polypeptide and the polypeptide may still retain at least one biological activity. Or; about 1, 2, 3, 4, 5, 6, 7, or more than 7 nucleotides could be removed from a polynucleotide and expression products of the polynucleotide may still retain at least one biological activity.

C/EBPβ does not contain an intron as found in various organisms including, but not limited to: human, mouse, and rat. However, if desired, it is possible using techniques known to one with skill in the art, to include an intron in a recombinant C/EBPβ polynucleotide sequence. For example, a bovine growth hormone (bGH) intron including splice sites may be added. In certain instances, the addition of an intron to a recombinant polynucleotide has been observed to increase expression of the encoded expression product in eukaryotic cells. It is understood that the addition of an intron creates a functionally equivalent sequence.

It is understood further in the art that insertions and deletions may be made within the amino acid and nucleic acid sequence, and yet still be essentially as set forth in one of the sequences disclosed herein, so long as the sequence meets the criteria set forth herein, including the maintenance of biological protein activity where protein expression is concerned. In general, insertions or deletion of residues in the coding region of a listed nucleic acid encoding a p20 protein should be made such that the net insertion or deletion is a multiple of 3. Thus, it is preferred that the reading frame of the polynucleotide sequence be maintained, as is known in the art (Alberts et al., supra, incorporated herein by reference).

Excepting intronic or flanking regions, and allowing for the degeneracy of the genetic code, sequences that have between about 70% and about 79%; or more preferably, between about 80% and about 89%; or even more preferably, between about 90% and about 99% of nucleotides that are identical to the nucleotides shown in the sequences of SEQ ID NO:1–4, 8, 10 and 17–20 will be sequences that are "essentially as set forth in SEQ ID NO:1–4, 8, 10 and 17–20". Sequences that are essentially the same as those set forth in SEQ ID NO:1–4, 8, 10 and 17–20 also may be functionally defined as sequences that are capable of hybridizing to a nucleic acid segment containing the complement of SEQ ID NO:1–4, 8, 10 and 17–20 under high stringency conditions. Suitable conditions are described in the summary herein.

At the protein level, peptide sequences that are essentially the same, in general, are capable of cross-reacting with antibody raised against the respective peptide factor. However, in the case of C/EBPβ, an antibody raised against a C-terminal epitope that is common to each isoform will then cross-react with each isoform containing the common epitope. Thus, for example, one may wish to use an antibody raised against the peptide in SEQ ID NO:14 for the positive identification of C/EBPβ-1. Methods for isolating, resolving, and analyzing protein/antibody interactions are well known in the art including techniques such as SDS-PAGE and Western analysis. Using SDS-PAGE and Western analysis in conjunction with the C-terminal C/EBPβ antibody (FIG. 1), one with skill in the art can resolve and identify proteins that cross react with p20 from biological samples through observation of molecular weight and reaction with the antibody. Polypeptides that cross react with p20 and migrate with a similar molecular weight are essentially the same as p20 (the molecular weight is not absolute, because some N-terminal or C-terminal amino acids may be added as described above (or encoded in a nucleic acid)).

Naturally, the present invention also encompasses nucleic acid segments that are complementary, or essentially complementary, to the sequences set forth in SEQ ID NO:1–4, 8, 10 and 17–20. Nucleic acid sequences that are "complementary" include those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1–4, 8, 10 and 17–20 under high stringency conditions.

The nucleic acid segments of the present invention, regardless of the length of the coding sequence itself, may be combined with other DNA sequences, such as promoters, polyadenylation signals, additional restriction enzyme sites, multiple cloning sites, other coding segments, nuclear localization sequences, membrane transport sequences, and the like, such that their overall length may vary considerably. It is therefore contemplated that a nucleic acid fragment of almost any length may be employed, with the total length preferably being limited by the ease of preparation and use in the intended recombinant DNA protocol. Therefore, the terms "p20 gene" or "p20 polynucleotide" may also comprise any combination of associated control sequences. Furthermore, those skilled in the art of mutagenesis will appreciate that other analogs, as yet undisclosed or undiscovered, may be used to construct p20 analogs (mutants, variants, etc). Additional meanings of biological functional equivalents, similarity, percent similarity, equivalents, substantially identical sequences, essentially the same, and essentially similar sequences and activities are described in U.S. Pat. No. 5,922,688 to Hung et al., incorporated herein by reference.

Naturally, the present invention also encompasses peptides and polypeptides (or the nucleic acid sequences that encode such peptides and polypeptides) that contain conservatively modified variants of the sequences listed in the Sequence Listings. One with skill in the art is able to readily determine conservative sequence modifications. In the case of a polypeptide, amino acid substitutions, such as those which might be employed in modifying C/EBPβ are generally based on the relative similarity of the amino acid side-chain substituents, for example, their hydrophobicity, hydrophilicity, charge, size, and the like.

An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., J. Mol. Biol. (1982) 157(1):105–32, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity. U.S. Pat. No. 4,554,101 to Hopp, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, supra, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

5.30 Sequence Modification Techniques

Modifications to p20 sequences may be made during chemical synthesis of the polymers (either nucleotide or peptide synthesis). Although, chemical synthesis of p20 polymers is possible, it is not cost effective at the time of filing. Therefore, the preferred method for changing the sequence of a p20 polymer is through site directed mutagenesis of an encoding nucleic acid, i.e., human CEBPB (SEQ ID NO:1). Where the p20 protein is desired, then the mutated sequence is expressed in culture (in vitro or ex vivo) or in vivo through administration and expression in cells of the mammal in need of treatment.

Site-specific mutagenesis is a technique useful in the preparation of individual peptides, or biologically functional equivalent proteins or peptides, through specific mutagenesis of the underlying DNA. Several methods for site directed mutagenesis are described in U.S. Pat. No. 4,873,192 to Kunkel, incorporated herein by reference and in U.S. Pat. No. 4,351,901 to Ball, incorporated herein by reference. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about 5 to 10 residues on both sides of the junction of the sequence being altered.

The technique of site-specific mutagenesis is well known in the art as exemplified by publications (Adelman et al., (1983) DNA 2(3)183–193, incorporated herein by reference). As will be appreciated, the technique typically employs a phage vector which exists in both a single stranded and double stranded form. Typical vectors useful in site-directed mutagenesis include vectors such as the M13 phage. These phage are readily commercially available and their use is well known to those skilled in the art. Double stranded plasmids are also routinely employed in site directed mutagenesis which eliminates the step of transferring the gene of interest from a plasmid to a phage. Kits for phage based site directed mutagenesis are commercially available. In addition PCR based methods which may, or may not, involve phage are known in the art and kits for such purposes are commercially available.

In certain known techniques, site-directed mutagenesis is performed by first obtaining a single-stranded vector or melting apart the two strands of a double stranded vector which includes within its sequence a DNA sequence which encodes the desired CEBPB isoform. An oligonucleotide primer bearing the desired mutated sequence is prepared, generally synthetically as is known to one of ordinary skill in the art. This primer is then annealed with the single-stranded vector, and subjected to DNA polymerizing enzymes such as *Escherichia coli* (*E. coli*) polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement. Various selection methods that increase the percentage of specifically modified clones over wild-type are known and available commercially.

Kalderon et al. (1984) report several mutagenic methods which have proved useful in mutating the native LT gene. Specifically, Kalderon et al. teach deletion mutations by displacement-loop mutagenesis and by the random insertion of Eco RI linkers into the LT gene. Further, point mutation by deletion-loop mutagenesis is taught. The reference also teaches screening procedures for determining the success of such mutations. The teachings of Kalderon et al. (1984) Virology 139(1)109–137 are incorporated herein by reference.

The preparation of sequence variants of the selected gene using site-directed mutagenesis is provided as a method of producing potentially useful p20 and is not meant to be limiting as there are other ways in which sequence variants of these peptides may be obtained. For example, recombinant vectors encoding the desired genes may be treated with mutagenic agents to obtain sequence variants for the mutagenesis of plasmid DNA using hydroxylamine or random mutagenesis may be performed using the PCR technique. Sequence analysis of a potentially mutant nucleic acid sequence is carried out by methods known in the art, typically by either Sanger dideoxy sequencing (Sanger et al., PNAS (1977) 74:5363–5467, incorporated herein by reference; U.S. Pat. No. 4,871,929 to Barnes; and U.S. Pat. No. 4,962,020 to Tabor et al., each patent incorporated herein by reference) or automated sequencing (U.S. Pat. No. 5,365,455 to Tibbetts et al., incorporated herein by reference).

In addition to the C/EBPβ peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

In addition to sequence equivalents, the inventors also specifically contemplate further biological variations of p20 that are functionally equivalent to p20. For example, p20 may be altered by phosphorylation, glycosylation, or other biological modification. The expression of p20 in mammalian cells is known to result in a biologically active molecule with regard to these additional modifications, as demonstrated herein. Sequences modified by any technique can be tested for biological activity according to known methods including those described in the Examples section in order to determine if that modified sequence is an equivalent, a conservatively modified variant, a biologically function equivalent, a biological variant, or is otherwise similar to a sequence described or listed herein.

5.40 Polynucleotide Compositions and Methods of Use thereof

In certain exemplary embodiments, the administration of an anti-inflammatory amount of p20 includes introducing a nucleic acid to a cell, wherein the nucleic acid includes a polynucleotide insert having at least a portion encoding p20. It is preferred to administer the nucleic acid directly to a cell in the mammal and that an anti-inflammation amount of p20 is expressed in the cell. These methods may be referred to as in vivo gene therapy or p20 gene therapy. However, other methods are acceptable including ex vivo administration to a cell taken from the mammal or administration to a cell from another organism that is compatible with introduction into the mammal (not immunogenic to the mammal).

It is preferred that the nucleic acid including the polynucleotide segment encoding p20, further include an expression vector operatively linked to the segment and include at least one control element for expression of the p20 isoform in the cell. In a general sense, the polynucleotide segment is often referred to as an "insert" or an "expression vector insert". The construction and use of expression vectors in genetic expression systems is well known in the art. In general, an insert encoding a factor to be expressed is cloned into the expression vector utilizing a bank of restriction sites located such that control elements in the vector will regulate expression of the insert (expression of a product from the insert). Genetic control elements may also be included in the insert. Exogenous genetic elements for driving expression include, but are not limited to: promoters, enhancers, ribosomal binding sites, nuclear localization sequences, membrane transport sequences, polyadenylation signals, etc. A number of these elements are described in U.S. Pat. No. 5,910,488 to Nabel et al.; incorporated herein by reference. The terms "control elements", "genetic regulatory elements", "genetic control elements", and grammatically similar expressions are used interchangeably herein. In certain embodiments, preferred inserts include, but are not limited to, the p20 polynucleotide segment (SEQ ID NO:4).

Numerous gene expression systems or expression vectors, methods for the construction of the expression vectors, methods for the insertion of desired nucleic acid sequences into the vectors, and methods for optimizing gene product expression from the vectors in various cells are known to those with skill in the art and may be used in conjunction with the present invention. The specific insertion of nucleic acid sequences encoding p20 into an expression vector of choice will be obvious to one with skill in the art including the techniques of molecular cloning which are described by numerous sources (see, Sambrook et al., Molecular Cloning: A Laboratory Manual, Second Edition (1989) Cold Spring Harbor Laboratory Press), incorporated herein by reference). In certain preferred embodiments, the expression vector contains the nucleic acid sequence encoding p20 along with various genetic elements that promote the constitutive or inducible expression of the desired gene product.

5.41 Expression Vectors

Many desirable expression vectors, including plasmid expression vectors, are available through commercial sources (e.g., Roche, Stratagene, In Vitrogene, Promega, etc)

and are useful for the expression of p20 in mammalian cells. In certain embodiments, the nucleic acid is transcribed and it is preferred that the resulting transcript is translated into a protein. Thus, in certain embodiments, expression includes both transcription of a gene and translation of a RNA into a gene product including p20. In other embodiments, expression only includes transcription of the nucleic acid, for example, to generate antisense constructs.

Particularly useful vectors are contemplated to be those vectors in which a coding portion of the DNA segment, whether encoding a full length protein, polypeptide or smaller peptide, is positioned under the transcriptional control of a genetic control element. One highly preferred control element includes a promoter. In certain aspects "promoter" refers to a DNA sequence recognized by the synthetic machinery of the cell, or introduced synthetic machinery, required to initiate the specific transcription of a gene. The phrases "operatively positioned", "under control" "regulates", or "under transcriptional control" include the meaning that the promoter is in the correct location and orientation in relation to the nucleic acid to control RNA polymerase initiation and expression of the gene. These terms are known to one of ordinary skill in the art.

The promoter may be in the form of the promoter that is naturally associated with a gene, as may be obtained by isolating the 5' non-coding sequences located upstream of the coding segment or exon, for example, using recombinant cloning and/or polymerase chain reaction (PCR™) technology (see U.S. Pat. No. 4,683,202 to Mullis; U.S. Pat. No. 4,683,195 to Mullis et al.; U.S. Pat. No. 4,800,159 to Mullis et al.; U.S. Pat. No. 4,965,188 to Mullis et al.; U.S. Pat. No. 5,656,493 to Mullis et al.; each patent incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a gene in its natural environment. Such promoters may include promoters normally associated with other genes, and/or promoters isolated from any other bacterial, viral, eukaryotic, or mammalian cell, and/or promoters made by the hand of man that are not "naturally occurring," i.e., containing elements from different promoters, or mutations that increase, decrease, or alter expression.

Naturally, it will be important to employ a promoter that effectively directs the expression of the DNA segment in the cell type, organism, or mammal, chosen for expression; the exemplary mammal being a human. The use of promoter and cell type combinations for protein expression, including various types of human cells, is known to those of skill in the art of molecular biology (for example, see Sambrook et al. (1989), supra). The promoters employed may be constitutive, or inducible, and can be used under the appropriate conditions to direct high level expression of the introduced DNA segment, such as is advantageous in the large-scale production of recombinant proteins or peptides.

Generally at least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region about 30–110 base pairs upstream of the start site, although a number of promoters have been shown to contain functional elements downstream of the start site as well. The spacing between promoter elements is often observed to be flexible, so that promoter function is preserved when elements are inverted or moved relative to one another. In the tk promoter, the spacing between promoter elements can be increased to 50 basepairs apart before activity begins to decline. Depending on the promoter, it appears that individual elements can function either cooperatively or independently to activate transcription.

In certain embodiments, the particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. In other embodiments, a particular promoter that directs expression to a certain tissue or allows for regulation of expression by an additional control element may be desired. The selection and use of such particular promoters will be apparent to those with skill in the art (see, e.g., U.S. Pat. No. 5,858,774 to Malbon et al.; Gene-Expression Systems (1998) Fernandez et al., eds. Academic Press; M. Kriegler, Gene Transfer and Expression: A Laboratory Manual (1991) Oxford University Press; Gene Therapy of Cancer (1999) Lattime et al., (eds.) Academic Press; and Gene Expression: General and Cell Type Specific (1993) M. Karin (ed.) Birkhauser; each reference being incorporated herein by reference).

In various embodiments, the human cytomegalovirus (CMV) immediate early gene promoter, the SV40 early promoter, and the Rous sarcoma virus long terminal repeat can be used to obtain high-level expression of the nucleic acid. The use of other viral or mammalian cellular promoters which are well-known in the art to achieve expression are contemplated as well, provided that the levels of expression are sufficient for a given purpose as stated in the specification including the claims. For example, in certain embodiments herein, the purpose is the treatment of an inflammatory response and inhibition of pro-inflammatory mediators (e.g., IL-6 and IL-8). Elements and promoters from the following genes and viral genomes may be useful, in the context of the present invention, to regulate the expression of a gene: β-Actin, metallothionein, H2B (TH2B) histone, mouse or type I collagen, SV40, polyoma virus, retroviral promoters, papilloma virus, hepatitis B virus, human immunodeficiency virus, cytomegalovirus, RSV LTR, whey acidic protein (WAP), and β-casein.

Inducible elements and promoter can be derived from the following genes and viral genomes with the inducing agent in parentheses: MT II (phorbol ester (TFA) and heavy metals), mouse mammary tumor virus (MMTV, stimulated by glucocorticoids), adenovirus 5 E2 (E1a), and SV40 (TPA). In certain embodiments, it is preferable to employ inflammation-specific promoters (i.e. promoters that are more active in inflamed cells than in non-inflamed cells). Preferred examples of such a promoters include, the interleukin 1β (IL-1β) promoter and the CMV promoter. These lists are not intended to be exhaustive of all the possible useful promoter elements involved in the promotion of expression, but they are exemplary thereof. Additional control elements are discussed, infra.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver), CC10 (lung) and prostate-specific antigen (prostate) will permit tissue-specific expression of p20 polynucleotides. This list is not intended to be exhaustive of all the possible elements useful in the promotion of p20 expression but, merely, to be exemplary thereof. In certain preferred embodiments, the promoter of choice is the CMV promoter which remains active with high levels of p20 expression. The CMV promoter and methods of use thereof, are described in U.S. Pat. Nos. 5,385,839 and 5,168,062 to Stinski, each patent incorporated herein by reference.

Enhancers were originally detected as genetic elements that increased transcription from a promoter located at a distant position on the same molecule of DNA. They are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter has one or more elements that direct initiation of RNA synthesis at a particular site and in a particular orientation, whereas enhancers generally lack such specifics. Promoters and enhancers are often overlapping and contiguous, often seeming to have a very similar modular organization. Additionally any promoter and enhancer combination could also be used to drive expression. Additional promoters and enhancers are described in the Eukaryotic Promoter Database (Rouaïda Cavin Périer et al. (1999) Nuc Acid Res 27:307–309, incorporated herein by reference and located on the World Wide Web at the URL "http//www.epd.isb-sib.ch", incorporated herein by reference).

In embodiments that use an expression vector, it is preferred that the vector contain an insert having at least a portion encoding p20, conservatively modified variant thereof, or a biologically functional equivalent genetic sequence of p20. The p20 genes should be positioned in the vector relative to control elements such that the p20 genes are transcribed and ultimately translated in a desired environment in the cell targeted by the treatment. Preferred control elements include, but are not limited to: promoters, enhancers, polyadenylation signals, translation control elements, nuclear localization signals, and membrane transport sequences. The control elements may enhance transcription, RNA processing, translation, secretion, cellular compartmentalization, or any other useful biological process. The control elements may regulate the biological processes of gene expression such that p20 is expressed from the vector when stimulated by an catalyst applied during treatment. Another element that may be used to enhance p20 expression is the creation of a Kozak sequence at the start site of p20 translation. A Kozak sequence is a translation initiation enhancer sequence. (For examples of translational enhancer compositions and methods of use thereof, see U.S. Pat. No. 5,807,707 to Andrews et al., incorporated herein by reference; U.S. Pat. No. 5,723,332 to Chernajovsky, incorporated herein by reference; U.S. Pat. No. 5,891,665 to Wilson, incorporated herein by reference).

Control may regulate translation in addition to transcription. Thus, another preferred control element includes an internal ribosome entry site (IRES), described in U.S. Pat. No. 4,937,190 to Palmenberg et al., incorporated herein by reference. The IRES facilitates the delivery of two proteins into animal cells using a single-transcript vector (STV). In such constructs a multiple cloning site (MCS) is located immediately downstream of a single promoter and is followed by the IRES sequence and a second multiple cloning site (or at least one unique restriction site for inserting a second gene sequence). This configuration enables two gene sequences on a single transcript to both be translated into protein. This system has been used with retroviral IRES-STVs in which a selectable drug marker gene was inserted immediately following the IRES. After drug selection, up to 99% of infected cells expressed the MCS-inserted gene as well. The ITES technology is available through Clontech Laboratories, Inc., Palo Alto, Calif.

In certain embodiments of the invention, the delivery of an expression vector in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. Red and Green Fluorescent Protein Markers are available from Clontech, supra. The selectable marker employed is not believed to be important, so long as it is capable of being expressed along with the polynucleotide encoding p20. Further examples of selectable markers and methods for constructing and using markers are well known to one of skill in the art.

One typically will include a polyadenylation signal (polyA) to effect proper polyadenylation of the transcript. The nature of the polyadenylation signal is not believed to be crucial to the successful practice of the invention, and any such sequence may be employed. The inventors prefer the bovine growth hormone (bGH) polyA for or plasmid vectors, the Moloney murine leukemia virus (MoMLV) polyA for retroviral vectors, the SV40 polyA for adenoviral vectors, in that it was convenient and known to function well in the target cells employed. Also contemplated as an element of the expression construct, but not preferred, is a terminator separate from the polyA. These elements can serve to enhance message levels and to minimize read through from the construct into other sequences.

Other expression vectors known in the art that may be useful for the expression of encoded genes in mammalian cells include, but are not limited to: pUC and Bluescript™ plasmid series, direct uptake of naked DNA, as well as receptor-mediated uptake of DNA complexes, DNA-liposome complexes (described in U.S. Pat. No. 5,676,954 to Brigham, incorporated herein by reference), cosmids, and phage constructs. A general resource for the construction and use of plasmid, recombinant, and viral vectors for gene-therapy that can be used, in certain embodiments, in light of the present invention is U.S. Pat. No. 5,545,563 to Darlington et al., incorporated herein by reference.

Once the expression construct has been delivered into the cell the nucleic acid encoding the gene of interest may be positioned and expressed at different sites within the cell. In certain embodiments, the nucleic acid encoding the gene may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments, gene transfer may more easily be performed under ex vivo conditions. Ex vivo gene therapy commonly refers to the isolation of cells from the mammal, the delivery of a nucleic acid into the cells, in vitro, and then the return of the modified cells back into the mammal. This may involve the surgical removal of tissue/organs from the mammal or the primary culture of cells and tissues. U.S. Pat. No. 5,399,346 to Anderson et al., incorporated herein by reference, disclose several ex vivo therapeutic methods. The preferred animal herein is a mammal and an especially preferred animal is a human. Particularly good methods of administration of plasmid expression vectors is by injection of naked DNA, inhalation of aerosolized naked DNA, incorporation into liposomes and uptake by treated cells, association with cationic liposomes by charge-charge interactions, instillation, and injection or aerosolization in general.

Advantages to plasmid expression vector based expression systems include: plasmids generally do not integrate into the genomic DNA of the host cell, plasmid systems are typically less immunogenic than viral based expression systems, broad range of host expression cell available, selective expression in certain host cells possible, temporal expression possible, and the bystander effect allows effective treatment even when gene transmission rates are low. The bystander effect is an known in the art as a substantial therapeutic effect resulting from transduction of a relatively small population of targeted cells. For example, an illustration of the bystander effect would be the regression of a tumor following gene therapy of the tumor in which fewer than 10% of the tumor cells were transformed by the gene therapy. The bystander effect is contemplated to influence treatment of inflammation also. The bystander effect is described in Gene Therapy of Cancer (1999) Lattime et al., (eds.) Academic Press, especially Chapter 10, incorporated herein by reference. The bystander effect also is described in U.S. Pat. No. 5,866,340 to Vogelstein et al., incorporated herein by reference. The description of the benefit plasmid based gene therapy by the bystander effect is not meant to limit the present invention, but merely to be illustrative thereof. The bystander effect is expected to benefit viral expression vector based therapy and other embodiments as well.

In certain embodiments of the present invention, expression vectors (including viral-based expression vectors, infra) are used to transduce various cell types including, but not limited to: BEAS, IB3, C38), and primary cells derived from pig and human lung samples. Primary cell samples are obtained from animal models and patients with diseases including, but not limited to: allergic rhinitis, asthma, adult respiratory distress syndrome (ARDS), cystic fibrosis (CF), and idiopathic pulmonary fibrosis (IPF). In certain embodiments, expression vectors (including viral-based expression vectors) are used for ex vivo or in vivo transduction of mammalian tissues or cell types including, but not limited to: epithelial, endothelial, hepatocyte, lymphoid, myeloid, vascular endothelium, and lung and bronchial epithelium. In certain embodiments, a measurements are made of IL-6 and IL-8 secretion from cells that are treated with p20.

5.42 Viral-Based Expression Vectors

In certain embodiments, viral expression vectors are preferred. Preferred viral based expression vectors include hybrid retrovirus/Epstein Barr virus vector (e.g., pLZR-SpBMN-Z described in U.S. Pat. No. 5,830,725 to Nolan et al., incorporated herein by reference; see Examples 2 and 3, FIGS. 9A–D, and 10A–C) and adenoviral expression vectors (e.g., pGEM-RecA; see Examples 4 and 5).

The viral vectors described in certain embodiments herein are non-replicating, meaning that no further virus spread occurs after infection. To distinguish this process from a natural virus infection where the virus continues to replicate and spread, the terms "transduce", "transduced", and "transduction" are commonly used and may be used herein.

Numerous viral-based viral expression systems are described in the prior art and the use of any of these systems, or any system developed in the future, in conjunction with the compositions and methods of the present invention and in light of the present disclosure, is contemplated. However, it is preferred that the viral expression system is compatible with administration to a mammal and that it facilitate the expression of p20 in a mammalian cell.

5.43 Retrovirus

The retroviruses are a group of single-stranded RNA viruses characterized by an ability to convert their RNA to double-stranded DNA to infected cells by a process of reverse-transcription (Retroviruses (1997) Coffin et al. (eds.), Cold Spring Harbor Laboratory; incorporated herein by reference; Gene Therapy of Cancer (1999) Lattime et al., (eds.) Academic Press, Chapter 4, incorporated herein by reference). Typically, the resulting DNA then stably integrates into cellular chromosomes as a provirus and directs synthesis of viral proteins. The integration results in the retention of the viral gene sequences in the recipient cell and its descendants. The retroviral genome contains gag, pol, and env genes that code for capsid proteins, polymerase enzyme, and envelope components, respectively. A sequence found upstream from the gag gene, termed $\psi$ contains a signal for the packaging of the viral genome into virions. Two long terminal repeat (LTR) sequences are present at the 5' and 3' ends of the viral genome. These contain strong promoter and enhancer elements and also direct integration of the viral nucleic acid into the host cell genome.

In order to construct a retroviral vector, in general, a nucleic acid encoding a promoter is inserted into the viral genome replacing the gag, pol, and env genes producing a replication deficient virus genome. In order to produce virions, a packaging cell line containing the gag, pol, and env genes; but without the LTR and $\psi$ components is constructed. Numerous packaging cell lines are known to one with skill in the art, are available commercially, and are available through the American Type Culture Collection (ATCC, Rockville, Md.).

When a recombinant plasmid containing a human cDNA, together with the retroviral LTR and $\psi$ sequences is introduced into the packaging cell line (by calcium phosphate precipitation for example), the $\psi$ sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. However, integration and stable expression is enhanced by the division of host cells.

Several concerns regarding the use of retroviral vectors include the potential for disruption of native genes of the host cell through random integration and the possibility of regeneration of a replication-competent particle through recombination in the packaging cell line. However, packaging cell lines are now available that should greatly decrease the likelihood of recombination (Markowitz et al. (1988) Virology 167(2):400–406; Markowitz et al. (1988) J. Virol. (62)1120–1124; Hersdorffer et al. (1990) DNA Cell Biol., (9) 713–723; each incorporated herein by reference).

Another limitation to the use of retrovirus vectors in vivo is the limited ability to produce retroviral vector titers greater than $10^6$ U/milliliter. Titers 10- to 1,000-fold higher are preferred for many in vivo applications.

Nevertheless, several innovations in the application of retroviruses demonstrate the utility of retroviral vectors for delivering the anti-inflammatory agent p20 in conjunction with the present invention. U.S. Pat. No. 5,911,983 to Barranger et al., incorporated herein by reference, describes the use of a retroviral vector for gene therapy of Gaucher disease. U.S. Pat. No. 5,910,434 to Rigg et al., incorporated herein by reference, describes packaging cell lines and methods of generating high titer retrovirus useful for gene therapy. U.S. Pat. No. 5,741,486 to Pathak et al., incorporated herein by reference, describes a method of preventing the formation of replication competent retrovirus particles by providing a retroviral vector that deletes an essential encapsidation sequence upon reverse transcription in the target cells. U.S. Pat. No. 6,017,761 to Rigg et al., describes a method for obtaining retroviral packaging cell lines producing high transducing efficiency retroviral supernatant. The treatment of tumors in a mammal using retroviral vectors and a p53 gene is described in U.S. Pat. No. 5,532,220 to Lee et al., incorporated herein by reference.

5.44 Hybrid Retrovirus

The preferred expression system for high efficiency gene transfer in the present invention includes a hybrid Epstein-Barr virus(EBV)/retroviral vector construct (LZRSpBMN-Z ) (U.S. Pat. No. 5,830,725 to Nolan et al., incorporated herein by reference). In addition to a murine retroviral backbone with a polylinker region to facilitate insertion of cDNAs, the LZRSpBMN-Z vector contains the Epstein-Barr virus Nuclear Antigen (EBNA) gene, EBV origin of replication and nuclear retention sequences (oriP), and a puromycin resistance gene (FIG. 11C). The nuclear replication and retention functions of this vector allow for rapid establishment of recombinant retroviral producer DNA as stable episomes within human retroviral packaging cell lines. Episomes are maintained at 5–20 copies per cell (approximately) for up to 2–3 months, given selection for puromycin resistance, resulting in high viral titers. The retroviral backbone in this vector consists of full-length Moloney murine leukemia virus longer repeat (LTR) and extended $\psi$ packaging sequences derived from the MFG series of retroviral vectors developed by Mulligan and colleagues (U.S. Pat. No. 4,868,116 to Morgan et al., incorporated herein by reference).

Helper-free retrovirus is produced by transfecting the LZRS-based his-C/EBPβ-1, his-C/EBPβ-3, or a control β-gal construct (see Examples 2 and 3) into a 293T-based amphotropic packaging cell line termed (φ)nx-ampho (provided by Gary Nolan, Stanford University, Calif., USA). The 293T-derived cell lines are transfected with high efficiency (50% to 80%, or more of total cells being transfected) using calcium phosphate mediated transfection. The (φ)nx-ampho packaging cell line was specifically developed by G. Nolan to produce high titer, helper free recombinant retrovirus. The improvements were designed to alleviate instability of retroviral production capacity and potential recombination problems. Thus, hygromycin and diphtheria toxin resistance genes were introduced as co-selectable markers for the gag-pol and amphotropic envelope constructs respectively. To reduce the potential for recombination, the gag-pol and envelope constructs are driven by different, non-MoMuLV promoters. The risk of rearrangements is further reduced when LZRS-based constructs are maintained episomally in fnx-based packaging lines, resulting in the safe production of helper-free retroviral stocks.

5.45 Adenovirus

Another method for in vivo delivery, including gene therapy, involves the use of an adenovirus vector. The use of adenoviral vectors for the delivery of gene therapy is known in the art. Adenoviral vectors and methods for use thereof, that include non-native coat proteins for reduced immunogenicity and increased cellular uptake are described in U.S. Pat. No. 5,965,541 to Wickham et al.; the life cycle of adenovirus, adenoviral vector compositions, and methods of use thereof for gene therapy are described in U.S. Pat. No. 5,731,190 to Wickham et al.; the use of adenoviral vectors incorporating a novel tumor suppressor gene in the treatment of cancer is described in U.S. Pat. No. 5,922,688 to Hung et al.; each patent is incorporated herein by reference.

Viral vectors based on the adenovirus are particularly suited for gene transfer and gene therapy because of its mid-sized genome, ease of manipulation, high titer viral particle production, wide target-cell range, and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP, located at 16.8 mµ is particularly efficient during the late phase of infection, and all the mRNA's issued from this promoter possess a 5'-tripartite leader (TL) sequence which makes them preferred mRNA's for translation.

In some cases, recombinant adenovirus is generated from homologous recombination between a shuttle vector and a provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

In certain embodiments, a method of introducing the p20 to a mammal is to introduce a replication-deficient adenovirus containing a polynucleotide segment or insert encoding p20. Certain preferred constructs are made replication deficient by deletion of the viral E1B and E3 genes. This avoids viral reproduction inside the cell and transfer to other cells and infection of other people. In other words, the viral infection activity is shut down after it transduces the target cell, but the p20 gene is still expressed inside the cells. Also, adenovirus is able to transfer the p20 gene efficiently into both proliferating and non-proliferating cells. Further, the extrachromosomal location of adenovirus in the infected cells decreases the chance of cellular oncogene activation within the treated mammal (adenoviruses do not generally integrate into the host cell genome).

The nature of the adenovirus vector is not believed to be crucial to the successful practice of the invention. Of course, as discussed above, it is advantageous if the adenovirus vector is replication defective, or at least conditionally defective, The adenovirus may be of any of the 42 different known serotypes or subgroups A–F. Adenovirus type 5 of subgroup C is the preferred starting material in order to obtain the conditional replication-defective adenovirus vector for use in certain embodiments of the present invention. This is because Adenovirus type 5 is a human adenovirus about which a great deal of biochemical and genetic information is known, and it has historically been used for most constructions employing adenovirus as a vector. The preferred adenoviral vector is pGEM-RecA (see Examples section).

Adenovirus is easy to grow and manipulate and exhibits broad host range in vitro and in vivo. This group of viruses can be obtained in high titers, e.g., $10^9$ $10^{11}$ plaque-forming units per ml, and the particles are highly infective. The life cycle of adenovirus does not require integration in to the host cell genome. The foreign genes delivered by adenovirus vectors are episomal and, therefore, have low genotoxicity to host cells. No side effects have been reported in certain studies of vaccination with wild-type adenovirus, demonstrating their safety and therapeutic potential as in vivo gene transfer vectors. However, other findings have shown a limitation with regard to immunogenic responses to adenoviral antigens.

U.S. Pat. No. 5,923,210 to Gregory et al., incorporated herein by reference, and U.S. Pat. No. 5,824,544 to Armentano et al., incorporated herein by reference, describe modifications to adenoviral vectors, and medical uses thereof, that decrease the potential for spontaneous generation of a replication competent adenovirus; thus, making the vectors even more safe for clinic use. The patents involve the deletion of the E1A (both patents) and E1B adenovirus genes (U.S. Pat. No. 5,923,210) and deletion (U.S. Pat. No. 5,923,210) or relocation (U.S. Pat. No. 5,824,544) of the adenovirus IX gene.

U.S. Pat. No. 5,792,453 to Hammond et al., incorporated herein by reference, describes adenoviral vectors useful for gene therapy for peripheral vascular disease and heart disease, including myocardial ischemia. The adenoviral vector is administered by intra-femoral artery or intracoronary injection conducted deeply in the lumen of the one or both femoral or coronary arteries (or graft vessels) in an amount sufficient for transfecting cells in a desired region.

Enhanced gene transfer to cancers arising from epithelial cells using adenoviral vectors and a transfer enhancing reagent, namely ethanol, is described in U.S. Pat. No. 5,789,244 to Heidrun et al., incorporated herein by reference.

Enhanced gene transfer to vascular cells using adenoviral and retroviral vectors and a transfer enhancing reagent, namely polyols, is described in U.S. Pat. No. 5,552,309 to March, incorporated herein by reference.

Successful delivery and expression of the cystic fibrosis transmembrane conductance regulator (CFTR) gene into the tracheobronchial passages of rhesus monkeys including the alveolar sacs using an adenovirus 5 based vector with a CFTR gene insertion and a technique for generating a viral aerosol is described in U.S. Pat. No. 5,952,220 to Sene et al., incorporated herein by reference.

5.45 Other Expression Systems

It is believed that the choice of expression vector, including viral-based expression vectors, is limited only by the pharmaceutical administration of the vector to the cell or mammal depending on the embodiment. Thus, it is preferred that the vector does not elicit an adverse immunological (meaning toxic) response in the mammal when treatment of a mammal is concerned. It is preferred that the vector does not support integration into the host cell genome because this may disrupt host cell gene expression. It is preferred, also, that the vector system support a level of expression of a composition of the present invention in a chosen cell that is therapeutically effective according to the particular embodiment (e.g., treating an inflammatory response or decreasing cellular pro-inflammatory cytokine production). Therefore, in addition to the non-infectious vectors, retroviral vectors, hybrid EBV/retroviral vectors, and adenoviral vectors; other expression vector systems, both known and to be developed, are contemplated to be useful in certain embodiments of the present invention in light of the present disclosure.

Alternative expression systems are pointed out below by way of example only. In certain embodiments of the present invention, the expression construct can be introduced into the cell using adenovirus assisted transfection. Increased transfection efficiencies have been reported in cell systems using adenovirus mediated systems as described in U.S. Pat. No. 5,928,944 to Seth et al. and U.S. Pat. No. 5,830,730 to German et al., each patent incorporated herein by reference. Other viral vectors may be employed as expression constructs in the present invention including, but not limited to: avipox, suipox, iridoviruses, picornavirus, calicivirus, and togavirus (all described in U.S. Pat. No. 5,656,465 to Panicali et al., incorporated herein by reference); a vaccinia virus modified for use in gene therapy (U.S. Pat. No. 5,858,373 to Paoletti et al., incorporated herein by reference); and gene therapy of liver tumors utilizing transcriptional elements of alpha-fetoprotein incorporated into SIN vectors is described in U.S. Pat. No. 5,843,776 to Tamaoki et al., incorporated herein by reference.

In vitro and in vivo gene therapy including the eye using LUX viral vector and Rb insert is described in U.S. Pat. No. 5,858,771 to Lee et al., incorporated herein by reference. Ocular gene therapy using recombinant vector and adenovirus vector is described in U.S. Pat. No. 5,827,702 to Cuthbertson, incorporated herein by reference. Gene therapy of the myocardium utilizing intra-femoral artery or intracoronary injection of adenoviral gene therapy vectors deep in the lumen of one or both femoral or coronary arteries (or graft vessels) is described in U.S. Patent Hammond et al., incorporated herein by reference.

U.S. Pat. No. 5,770,580 to Ledley et al., incorporated herein by reference, describes somatic gene therapy to cells associated with fluid spaces, such as follicles of the thyroid, the synovium of the joint, the vitreous of the eye and the inner or middle ear. Formulated DNA expression vectors are introduced with or without formulation elements into fluid spaces under conditions in which cells associated with the fluid space can incorporate the formulated DNA expression vector. Formulated DNA expression-mediated gene therapy allows treatment of diseases involving cells associated with fluid spaces. Recombinant viral and plasmid vectors for gene-therapy directed to the lung are described in U.S. Pat. No. 5,240,846 to Collins et al., incorporated herein by reference.

Generation of high titers of recombinant adeno-associated virus (AAV) vectors and the application of AAV vectors in gene therapy is described in U.S. Pat. No. 5,658,776 to Flotte et al., incorporated herein by reference. AAV-mediated gene therapy is also described in Gene Therapy of Cancer (1999) Lattime et al., (eds.) Academic Press, Chapter 6, incorporated herein by reference.

5.50 Production and Purification of p20 Protein

In certain embodiments, p20 polypeptide is used for treatments described in the present invention. Although the p20 polypeptide can be isolated from natural sources such as rat, mouse, or human cells; it is preferred that they be produced using recombinant techniques due to the increased risk of contamination by pathogens when derived from native sources. The cloning of and propagation of the human C/EBPβ nucleotide sequence in plasmid vectors are described in U.S. Pat. No. 5,215,892 to Kishimoto et al. and U.S. Pat. No. 5,360,894 to Kishimoto et al., each patent incorporated herein by reference. Additional methods for cloning and propagation of nucleotide sequences in general, and the p20 nucleotide sequence in particular is known to one with ordinary skill in the art. Methods for obtaining such sequences from different sources (i.e., murine, rat, chicken, xenopus, etc.) are also known.

In general, p20 protein can be made by inserting an encoding nucleic acid sequence into an expression vector suitable for expression in the host cell of choice including bacteria (e.g., BL21-pLysS, which does not phosphorylate the protein product), yeast (e.g., SF9), insect (phosphorylated peptides, used in conjunction with a baculovirus vector), and mammalian host cells which provide wild type phosphorylation. These recombinant expression systems are known in the art and commercially available.

The present invention also provides purified, and in certain preferred embodiments, substantially purified p20 polypeptide. The term "purified p20 polypeptide" as used herein, is intended to refer to a p20 proteinaceous composition, isolatable from endogenous or recombinant sources, wherein the p20 polypeptide is purified to any degree relative to its naturally-obtainable state, i.e., relative to its purity within a cellular extract. A purified p20 polypeptide therefore also refers to a wild-type or mutant p20 polypeptide free from the environment in which it naturally occurs.

Generally, "purified" will refer to a p20 polypeptide composition that has been subjected to fractionation to remove various non-p20 proteins, polypeptides, or peptides, and which composition substantially retains its p20 activity (Examples). Where the term "substantially purified" is used, this will refer to a composition in which the p20 polypeptide forms the major component of the composition, such as constituting about 51% of the proteins in the composition or more. In preferred embodiments, a substantially purified protein will constitute more than 70%, 80%, 90%, or even more than 95% of the proteins in the composition. In even more preferred embodiments, a substantially purified protein will constitute 99%, or even more than 99% of the proteins in the composition. The amount of a particular protein can be determined by comparing the opacity of the protein band with other proteins in the same lane after running the sample by SDS/PAGE and visualizing the proteins by silver staining as is known in the art.

A peptide, polypeptide or protein that is "purified to homogeneity," as applied to the present invention, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of p20 protein will be known to those of skill in the art in light of the present disclosure. These include, for example, determining the specific p20 protein activity of a fraction, or assessing the number of polypeptides within a fraction by gel electrophoresis. Assessing the number of polypeptides within a fraction by SDS/PAGE analysis will often be preferred in the context of the present invention as this is straightforward.

To purify a p20 polypeptide a natural or recombinant composition comprising at least some p20 polypeptides will be subjected to fractionation to remove various non-p20 components from the composition. In addition to those techniques, various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another example is the purification of an p20 fusion protein using a specific binding partner. Such purification methods are routine in the art. As the Kishimoto U.S. Pat. No. 5,215,892 patent provides a C/EBPβ nucleotide sequence; then any fusion protein purification method can now be practiced. This is exemplified by the generation of an p20 glutathione S-transferase fusion protein, expression in *E. coli*, and isolation (including to homogeneity) using affinity chromatography on glutathione-agarose. Given the DNA and proteins described in the present invention, any purification method can now be employed.

The preferred method of protein isolation is by affinity chromatography of a 6×His Tag included in the nucleic acid encoding the p20 protein products (see the Examples section). The 6×His Tag adds an additional 0.84 kDa to the overall molecular weight of the protein product and does not interfere with the p20 activity. The expression product is then purified by chromatography on a nickel-nitrilotriacetic acid (Ni-NTA) column. If the 6×His Tag is found to interfere with an activity of the protein product for a specific purpose, the tag can be removed. All of these protein product purification techniques are known to one with skill in the art (see e.g., Petty (1996) Current Protocols in Molecular Biology Vol. 2, John Wiley and Sons Publishers, incorporated herein by reference) and are commercially available from Qiagen (Valencia, Calif. 91355).

Although preferred for use in certain embodiments, there is no general requirement that the p20 polypeptide always be provided in their most purified state. Indeed, it is contemplated that less substantially purified p20 compositions which are nonetheless enriched in p20 protein, relative to the natural state, will have utility in certain embodiments. These include, for example, antibody generation where subsequent screening assays using purified p20 proteins are conducted. Methods exhibiting a lower degree of relative purification may have advantages in total recovery of protein product, or in maintaining the activity of an expressed protein. Inactive products also have utility in certain embodiments, such as, e.g., in antibody generation.

Turning to the expression of the proteins, once a suitable clone or clones have been obtained, whether they be cDNA based or genomic, one may proceed to prepare an expression system. The engineering of DNA segment(s) for expression in a prokaryotic or eukaryotic system may be performed by techniques generally known to those of skill in recombinant expression. It is believed that virtually any expression system may be employed in the expression of the proteins.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. In general, it is believed that the use of a cDNA version will provide advantages in that the size of the gene will generally be much smaller and more readily employed to transfect the targeted cell than will a genomic gene, which will typically be up to an order of magnitude or more larger than the cDNA gene. Although, it is contemplated that a genomic version of a particular gene may be employed where desired. In the present case, however, C/EBPβ (including C/EBPβ-3) does not contain an intron. Thus, the genomic and cDNA sequences are similar without intervening intron(s).

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette, in certain embodiments, is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the translation initiation site for C/EBPβ-1 and/or C/EBPβ-2 may be modified to prevent expression of C/EBPβ-1 and/or C/EBPβ-2. Such nucleic acids are contemplated to be useful for the expression and purification of p20 (C/EBPβ-3). The amount of C/EBPβ-1 and/or C/EBPβ-2 in the starting fraction would be reduced or eliminated depending on the host cell (certain mammalian cells may express some C/EBPβ-1 and/or C/EBPβ-2, but other cells will not). Such a construct may be useful also in conjunction with a vector for gene therapy in certain embodiments. Preferred methods to modify the translation start site include eliminating the ATG (for C/EBPβ-1 and/or C/EBPβ-2) by site-directed mutagenesis. In certain embodiments, it is also preferred that a Kozak sequence be formed around the third ATG (for enhanced p20 expression).

It is proposed that proteins, polypeptides or peptides may be co-expressed with other selected proteins, wherein the proteins may be co-expressed in the same cell or a gene(s) may be provided to a cell that already has another selected protein. Co-expression may be achieved by co-transfecting the cell with two distinct recombinant vectors, each bearing a copy of either of the respective DNA. Alternatively, a single recombinant vector may be constructed to include the coding regions for both of the proteins, which could then be expressed in cells transfected with the single vector. In either event, the term "co-expression" herein refers to the expression of both the gene(s) and the other selected protein in the same recombinant cell.

As used herein, the terms "engineered" and "recombinant" cells or host cells are intended to refer to a cell into which an exogenous DNA segment or gene, such as a cDNA or gene encoding an protein has been introduced. Engineered cells are thus cells having a nucleic acid, a gene, or genes introduced through the hand of man. Therefore, engineered cells are distinguishable from naturally occurring cells which do not contain a recombinantly introduced exogenous DNA segment or gene. Recombinant cells include those having an introduced cDNA or genomic gene, and may also include genes positioned adjacent to a promoter not naturally associated with the particular introduced gene.

To express a recombinant protein, polypeptide or peptide, whether mutant or wild-type, in accordance with the present invention one would prepare an expression vector that comprises a wild-type, or mutant protein-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" (i.e., 3') of the chosen promoter. The "upstream" (i.e., 5') promoter stimulates transcription of the DNA and promotes expression of the encoded recombinant protein. This is a meaning of "recombinant expression" in this context.

Many standard techniques are available to construct expression vectors containing the appropriate nucleic acids and transcriptional/translational control sequences in order to achieve protein, polypeptide or peptide expression in a variety of host-expression systems. Cell types available for expression include, but are not limited to, bacteria, such as *E. coli* and *B. subtilis* transformed with recombinant bacteriophage DNA, plasmid DNA, or cosmid DNA expression vectors. The use of cosmid DNA and artificial chromosomes is common particularly in yeast or mammalian expression systems.

Certain examples of prokaryotic hosts are *E. coli* strains: DH5α (preferred), HB101, *E. coli* BL21, *E. coli* BL21-pLysS, *E. coli* BL21-pLysE, RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy method for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors. In certain preferred embodiments, the T7 promoter is used.

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media, for example, LB. The expression of the recombinant protein may be induced, e.g., by adding IPTG to the media or by switching incubation to a higher temperature. After culturing the bacteria for a further period, generally of between 2 and 24 hours, the cells are collected by centrifugation and washed to remove residual media.

The bacterial cells are then lysed, for example, by disruption in a cell homogenizer or by sonication (preferred) and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case for C/EBPβ isoforms, the inclusion bodies can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol). These techniques are known in the art.

In certain embodiments, it is preferred to incubate the protein for several hours under conditions suitable for the protein to undergo a refolding process into a conformation which more closely resembles that of the native protein. Such conditions generally include low protein concentrations, less than 500 mg/ml, a reducing agent (high levels of a reducing agent are preferred for the present invention), concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns. As described supra, a polyhistidine tag and Ni-agarose chromatography are preferred.

For expression in *Saccharomyces,* the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are may also by ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus (CaMV) or tobacco mosaic virus, (TMV)) or transformed with recombinant plasmid expression vectors (e.g., Ti plasmid) containing one or more protein, polypeptide or peptide coding sequences.

In a useful insect system, *Autograph californica* nuclear polyhedrosis virus (AcNPV) is used as a vector to express foreign genes. The virus grows in *Spodoptera frugiperda* cells. The protein, polypeptide or peptide coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, Smith, incorporated herein by reference).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation, phosphorylation) and processing (e.g., cleavage) of protein products may be important for the function of the protein in certain embodiments. Different host cells have characteristic and specific mechanisms for the post-translational processing and modification of proteins. Appropriate cells lines or host systems can be chosen to ensure the correct modification and processing of the foreign protein expressed. In addition, the protein product (e.g., p20) may be co-expressed with a specific kinase which will provide the desired phosphorylation of the protein product.

Expression vectors for use in mammalian cells ordinarily include an origin of replication (as necessary), a promoter located in front of the gene to be expressed, along with any necessary ribosome binding sites, RNA splice sites, polyadenylation site, and possibly transcriptional terminator sequences. The origin of replication may be provided either by construction of the vector to include an exogenous origin, such as may be derived from SV40 or other viral (e.g., polyoma virus, adenovirus, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the gene sequence(s), provided such control sequences are compatible with the host cell systems.

A number of viral based expression systems may be utilized, for example, commonly used promoters are derived from polyoma, Adenovirus 2, and frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 basepair sequence extending from the Hind III site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1, E3, or E4) will result in a recombinant virus that is viable and capable of expressing proteins, polypeptides or peptides in infected hosts.

Specific initiation signals may also be required for efficient translation of protein, polypeptide or peptide coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements and transcription terminators.

In eukaryotic expression, one will also typically desire to incorporate into the transcriptional unit an appropriate polyadenylation site (e.g., 5'-AATAAA-3') if one is not contained within the original cloned segment. Typically, the poly A addition site is placed about 30 to 2000 nucleotides "downstream" of the termination site of the protein at a position prior to transcription termination.

For long-term, high-yield production of a recombinant protein, polypeptide or peptide, stable expression is preferred. For example, cell lines that stably express constructs encoding an protein, polypeptide or peptide by the methods disclosed herein may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (tk), hypoxanthine-guanine phosphoribosyltransferase (hgprt) and adenine phosphoribosyltransferase (aprt) genes, in tk-, hgprt- or aprt- cells, respectively. Also, antimetabolite resistance can be used as the basis of selection for dihydrofolate reductase (dhfr), that confers resistance to methotrexate; gpt, that confers resistance to mycophenolic acid; neomycin (neo), that confers resistance to the aminoglycoside G-418; and hygromycin (hygro), that confers resistance to hygromycin. Also, puromycin is often used.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth). Non-anchorage dependent or suspension cultures from continuous established cell lines are the most widely used method of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use: the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the proteins, polypeptides or peptides produced by the methods of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

5.60 Pharmaceutical Compositions, Administration, and Dosage

In preferred embodiments, the administration of p20 comprises introducing p20 protein and/or p20 encoding nucleic acid to a mammalian cell. Preferably, the nucleic acid form expresses p20 in the mammalian cell. The administration to the cell can be conducted in vivo, ex vivo, or in vitro. These terms are known in the art. In certain preferred embodiments, the ex vivo approach is used where tissue is removed from the mammal (or an acceptable donor organism), treated, and placed back into the mammal. In certain exemplary embodiments, the in vivo approach is used where the cell is treated directly in the mammal. Naturally, it is preferred that the p20 is administered to the cell in the context of a pharmaceutical formulation or composition.

In certain embodiments, the preferred method of administering the p20 isoform of C/EBPβ is in combination with an excipient (a pharmaceutically acceptable carrier). The excipient combined with the p20 may be administered by any mode or route known and to any cell, tissue, or organ of the mammal. The combination of an pharmaceutically acceptable carrier and the pharmaceutically active ingredient (including, but not limited to, p20 as other active ingredients may be included) is referred to herein as a pharmaceutical formulation.

The particular excipient is not believed to be critical as long as it is compatible with the biological activity of the active ingredient and compatible with administration to the subject (including a cell, mammal, or human). The choice of excipient depends on the nature of the inflammation or cell being treated, the location of treatment, and the active ingredient. A pharmaceutical formulation of liposomes (excipient) and hybrid retro/EBV-p20 expression vector is highly preferred in certain embodiments. This formulation can be injected into the local tissue or the afferent blood supply for treatment of inflammation or the prevention of inflammation in a population of cells, it can be combined with additional inert or carrier ingredients and used as a topical salve (e.g., for treatment of inflammation-associated skin disease), and it can be used with an aerosolization device for inhalation (e.g., to treat a bronchiopulmonary inflammatory reaction). The inventors specifically contemplate that p20 will be used to prevent inflammation or inflammatory reactions (e.g., an inhaler that delivers a metered and aerosolized dose of p20 may be used to prevent an asthmatic reaction to cold, exercise, and allergen).

As mentioned, the choice of excipient depends on the type, location, and nature of the inflammation; as well as, the route and mode of administration. The choice of pharmaceutically acceptable carrier can be made by one with skill in the art, such as the treating physician. The liposome/adenoviral formulation and additional recommended carriers, formulations, and modes of administration are described below.

Pharmaceutical compositions of the present invention will have an effective amount of a gene or peptide for therapeutic administration in combination with a pharmaceutically acceptable carrier. The gene or peptide may be dissolved or dispersed in the carrier and the carrier may be as simple as water. Although purified and sterile water is preferred and the addition of salts, pH buffers, and preservatives may be desired.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Thus, the numerous examples of pharmaceutically acceptable carriers that are provided herein, are provided by way of example and are not meant to limit the scope of the present invention. Supplementary active ingredients, such as other anti-inflammatory agents either known or discovered after the filing date hereof, can also be incorporated into the compositions. Also, compounds that are found to act synergistically with agents of the present invention may be used in combination or incorporated into the pharmaceutical compositions. The present invention may also be performed in combination with surgery. In one example, the present compositions and methods may be used to render an untreatable inflammatory response, treatable by other known methods. So, the present invention can be applied to an inflammatory response making the inflammatory response treatable by, for example, corticosteroid treatment.

The expression vectors and delivery vehicles of the present invention may include classic pharmaceutical preparations. Administration of these compositions according to the present invention will be via any common route so long as the target tissue is available via that route. This includes, but is not limited to: oral, dermal, nasal, buccal, rectal, vaginal or topical. Administration may be by orthotopic, intradermal, subcutaneous, intramuscular, intraocular, intraperitoneal or intravenous injection. An exemplary route of administration is inhalation of an aerosol for treatment of inflammation associated with the lungs. Such compositions would normally be administered as pharmaceutically acceptable compositions, described supra.

In certain embodiments, pharmaceutical formulations of the present invention are directly injected into an inflamed foci or among a population of cells. In the case of direct injection, it is preferred that the pharmaceutical formulation is injected into the foci, optionally multiple times, optionally multiple times spaced about 5 millimeters apart over the area of the foci.

In embodiments wherein an inflammatory response is identified, the response can be in and treated in any body component or in multiple body components including, but not limited to the: adipose, bladder, bone, brain, central nervous system, cartilage, cervix, eye, fallopian tube, heart, intestine, joint, kidney, liver, lung, lymphoid, muscle, ovary, pancreas, peripheral nervous system, peritoneum, prostate, skin, spleen, stomach, tendon, testicle, uterus, and vasculature.

In certain embodiments the above body components are treated when an inflammatory response has not been identified (e.g., for the prevention of inflammation) or when a subject has not been examined for inflammation. The purposes of such treatment include, but are not limited to: the prevention of inflammation and the inhibition of pro-inflammatory mediators.

The vectors of the present invention are advantageously administered in the form of injectable compositions either as liquid solutions or suspensions; solid forms suitable may be solubilized or suspended in liquid prior to injection. These preparations also may be emulsified. In certain embodiments, a typical composition comprises about 50 mg or up to about 100 mg of human serum albumin per milliliter of phosphate buffered saline. Other pharmaceutically acceptable carriers include aqueous solutions, salts, preservatives, buffers and the like. Examples of non-aqueous solvents are propylene glycol polyethylene glycol. vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well known parameters.

Additional formulations are suitable for oral administration. Oral formulations include such typical excipients as; for example, pharmaceutical grades of mannitol, lactose, starch, magnesium stearate, sodium saccharine, cellulose, magnesium carbonate, and the like. The compositions take the form of solutions. suspensions tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

All the essential materials and reagents required for treating an inflammation may be assembled together in a kit. When the components of the kit are provided in one or more liquid solutions, the liquid solution preferably is an aqueous solution, with a sterile aqueous solution being particularly preferred. Containers for the components may include an inhalant, syringe, pipette, eye dropper, or other apparatus, from which the formulation may be applied to an infected area of the body, such as the lungs, injected into a mammal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container within the kit. The kits of the invention may also include an instruction sheet defining administration of p20 polypeptide therapy and/or gene therapy and the pharmaceutical indications of the kit components.

The kits of the present invention also will typically include a vessel for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of a mammal. Such an instrument may be an inhalant, syringe, pipette, forceps, measured spoon, eye dropper or any such medically approved delivery vehicle.

Parenteral administration, such as intravenous or intramuscular injection, is an exemplary method of delivering the anti-inflammation agents of the present invention to many cell populations. Administration of polypeptides and nucleic acids by injection for the treatment of disease is described in U.S. Pat. No. 5,580,859 Felgner et al., incorporated herein by reference. Alternatively non-parenteral administration may be desired, including: oral administration; time release capsules; and any other form known in the art, including cremes, lotions, mouthwashes, inhalants and the like. In one example, gene therapy using the intestine is described in U.S. Pat. No. 5,821,235 to Henning et al., incorporated herein by reference.

The active compounds of the present invention will often be formulated for parenteral administration, e.g., formulated for injection via the intravenous, intramuscular, subcutaneous, and intraperitoneal routes. Typically, such compositions can be prepared as injectables, either as liquid solutions or suspensions; solid forms suitable for preparation of solutions or suspensions upon the addition of a liquid prior to injection may be desired; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions can be used. It is preferred that the form is sterile and that it is fluid to the extent that it can be aspirated into a syringe. It should be stable under the conditions of manufacture and storage and should be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as needed, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media which can be employed will be known to those of skill in the art in light of the present disclosure. For example, one dosage could be dissolved in 1 milliliter of isotonic NaCl solution and either added to about 1 liter of hypodermoclysis fluid or injected at the proposed site of infusion, (see for example, "Remington's Pharmaceutical Sciences" 15th Edition, pages 1035–1038 and 1570–1580, incorporated herein by reference). Some variation in dosage will necessarily occur depending on the condition of the subject being treated. The person responsible for administration will, in any event, determine the appropriate dose for the individual subject.

Targeting of inflamed tissues may be accomplished in any one of a variety of ways. Plasmid vectors and retroviral vectors, adenovirus vectors, and other viral vectors all present methods by which to target human inflamed. The inventors anticipate particular success for the use of liposomes to transfer polynucleotides and polypeptides of the present invention into cells including inflamed or non-involved lung cells. In one of the first series of clinical phase to be performed, DNA encoding p20 will be mix with liposomes, and this p20-vector/liposome complex will be administered to patients with certain forms of advanced stage adult respiratory distress syndrome (ARDS) by inhalation of an aerosol. The preferred vector for the initial phase is the pCMV-p20(His) (see FIG. 11A, also called pcDNA3.1HisC/EBPβ-3) because administration of this vector backbone (containing a different insert) is known by the inventors to not elicit an inflammatory response when administered as an aerosol to the lungs of a human patient. Intravenous injection into the afferent blood supply to the organ can also be used to direct the gene to most or all cells of the lung. Directly injecting the liposome-p20 based pharmaceutical formulation into the proximity of an inflamed foci can also provide for targeting of the formulation. Of course the potential for liposomes that are selectively taken up by a certain populations of cells exists, and such liposomes will also be useful for targeting the gene.

Those of skill in the art will recognize that the best treatment regimens for using compositions of the present invention, including p20, to suppress inflammation can be straightforwardly determined. This is not a question of experimentation, but rather one of optimization which is routinely conducted in the medical arts. The in vivo studies in nude mice provide a starting point from which to begin to optimize the dosage and delivery regimes. The frequency of injection will initially be once a week. However, this frequency might be optimally adjusted from one day to every two weeks to monthly, depending upon the results obtained from the initial clinical trials and the needs of a particular patient. Human dosage amounts can initially be determined by extrapolating from tests with anti-tumor biological therapeutics; for example, U.S. Pat. No. 5,922,688 to Hung et al., incorporated herein by reference. Accordingly, approximately 15 μg of nucleic acid (p20 encoding, referred to here as p20 DNA) per 50 kg body weight is desirable. Based on this, a 50 kg woman would receive a dose of approximately 15 mg of p20 DNA per treatment. In certain embodiments it is envisioned that this dosage may vary from between about 100 μg/50 kg body weight to about 5 μg/g body weight; or from about 90 μg/50 kg body weight to about 10 μg/g body weight or from about 80 μg/50 kg weight to about 15 μg/g body weight; or from about 75 μg/50 kg body weight to about 20 μg/g body weight; or from about 60 μg/50 kg body weight to about 30 μg/g body weight about 50 μg/50 kg body weight to about 40 μg/g body weight. In certain embodiments this dose may be about 0.015, 0.15, 0.5, 1, 2, 3, 5, 8, 10 15, or 20 μg/50 kg of body weight. Of course, these dosage amounts may be adjusted upward or downward, as is routinely done in such treatment protocols, depending on the results of the initial clinical trials and the needs of a particular patient. Dosage amounts may be adjusted upward or downward by any amount determined to be needed including 10 fold, 100 fold, and 1000 fold.

5.61 Administration by Transfection

The term "transfection" generally refers to the introduction of a nucleic acid into a eukaryotic cell. The present invention also contemplates the transfer or "transfection" of polypeptide/protein forms of p20 into mammalian cells. In many the instances, the methods used for nucleic acid transfection are easily adopted for the transfer of proteins and are known in the art (see, e.g., Gene Transfer and Expression Protocols (Methods in Molecular Biology, VOL 7) (1991) E. J. Murray (ed.) Humana Press; M. Kriegler, Gene Transfer and Expression: A Laboratory Manual (1991) Oxford University Press, each reference incorporated herein by reference). In addition, there are numerous commercially available transfection kits (e.g., Stratagene, InVitrogen, Roche, and the like). Transfection techniques being utilized in vivo and ex vivo, are disclosed in U.S. Pat. No. 5,858,784 to R. J. Debs et al., incorporated herein by reference. Transfection techniques are particularly useful for the transfer of nucleic acid compositions of the present invention into cells wherein transduction by viral-based expression vectors is not employed. Although, these techniques may be used in combination with viral-based vector transduction.

5.62 Lipid Mediated Transfer

Liposome mediated transfection is an exemplary method of introducing p20 polypeptide or polynucleotide compositions into a cell for treatment. Liposome and lipid based methods are readily known to those of skill in the art and numerous kits are available commercially (see e.g., Liposome Technology: Liposome Preparation and Related Techniques (1992) G. Gregoriadis (ed.) CRC Press, incorporated herein by reference; U.S. Pat. No. 5,279,833 to Rose, incorporated herein by reference; U.S. Pat. No. 5,567,433 to Collins, incorporated herein by reference; U.S. Pat. No.

4,515,736 to Deamer, incorporated herein by reference; Felgner et al., (1987) Proc. Nat. Acad. Sci., USA 84:471–477, incorporated herein by reference; and Gao et al (1991) Biochem. Biophys. Res. Comm. 179:280–285, incorporated herein by reference).

Currently, gene delivery with cationic lipids is currently the most clinically developed approach to gene therapy (Gene Therapy of Cancer (1999) Lattime et al., (eds.) Academic Press, Chapter 20, incorporated herein by reference). In general, cationic lipids are synthetically manufactured and can be readily mixed with any polynucleotide or polypeptide desired and form linkages based on non-covalent charge-charge interactions; although, covalent linkage is possible also. Numerous cationic lipids are available commercially and can be used in conjunction with the present invention for gene delivery (including in vivo, in vitro, and ex vivo). One of the biggest advantages to using cationic or liposome mediated gene transfer is that the non-infectious expression vectors described herein are not immunogenic when administered to a mammal including a human. This is especially true when compared to adenoviral-based expression systems which may be the most immunogenic (although useable) embodiment described herein.

Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. One such commercially available liposomal transfection reagent is Lipofectamin™ (DOTMA:DOPE by Gibco-BRL).

In certain embodiments of the present invention, the liposome may be complexed with a hemagglutinating virus (HVJ). This has been shown to facilitate fusion with the cell membrane and promote cell entry of liposome-encapsulated DNA. In other embodiments, the liposome may be complexed or employed in conjunction with nuclear non-histone chromosomal proteins (HMG-1). In yet further embodiments, the liposome may be complexed or employed in conjunction with both HVJ and HMG-1. In other embodiments, the delivery vehicle may comprise a ligand and a liposome to target the liposome to particular cell types or tissues.

U.S. Pat. No. 5,059,421 to Loughrey et al., incorporated herein by reference; describes a general method of attaching protein molecules to liposomes to achieve well-characterized and sized protein-liposome conjugate systems for interchangeable targeting applications. This pharmaceutical liposomal composition can be targeted to essentially any cell type or tissue, if desired. U.S. Pat. No. 4,885,172 to Bally et al., incorporated herein by reference; describes compositions and methods for storing liposomes including targeted liposomes and the loading of the such liposomes on an "as needed" basis. U.S. Pat. No. 5,851,818 to Huang et al., incorporated herein by reference; discloses improved methods for preparing nucleic acid/liposome complexes including selection of the working medium and liposome lipid to nucleic acid ratios. U.S. Pat. No. 5,279,883 to Rose, incorporated herein by reference; describes liposomal transfection of nucleic acids into animal cells. U.S. Pat. No. 5,225,212 to Martin, incorporated herein by reference; describes a liposome composition for extended release of a therapeutic compound into the bloodstream and methods for use thereof.

5.63 Membrane Transport Sequence (MTS) Mediated Transfer

In certain embodiments, a membrane transport sequence (MTS) can function as an agent for the administration of a composition of the present invention, including p20, to a cell. It is demonstrated that when a cell is contacted with a composition linked to an MTS, the entire MTS linked composition translocates through the cytoplasmic membrane of a cell (U.S. Pat. No. 5,807,746 to Lin et al., incorporated herein by reference and U.S. Pat. No. 5,877,282 to Nadler et al., incorporated herein by reference). Two functional MTS sequences are provided in the Sequence Listings (SEQ ID NO:12 and SEQ ID NO:13). Additional functional MTS sequences are described in U.S. Pat. No. 5,962,415 to Nadler, incorporated herein by reference.

The MTS can be combined with p20 chemically utilizing the carboxy and amino groups on the proteins or by molecular cloning of an MTS encoding DNA sequence into the p20 expression vector to form a fusion gene with subsequent expression of a fusion protein. The fusion protein may subsequently be expressed in vitro or in vivo. A fusion gene or fusion protein is one in which two or more sequences which are not combined in nature are combined by the hand of man. A similar term is "chimeric". The MTS-p20 chimera may include a linker sequence if desired.

5.65 Electroporation, Calcium Phosphate, and Particle Bombardment

In certain embodiments a composition of the present invention is introduced into a cell via electroporation. Electroporation involves the exposure of a suspension of cells and the composition to a high-voltage electric discharge (see U.S. Pat. No. 4,956,288 to Barsoum, incorporated herein by reference). Transfection of nucleic acids and proteins into eukaryotic cells using electroporation is quite successful and known in the art.

In certain embodiments a composition of the present invention is introduced into a cell using calcium phosphate precipitation. Transfection with calcium phosphate is described in U.S. Pat. No. 5,633,156 to Wurm et al., incorporated herein by reference. Human KB cells have been transfected with adenovirus 5 DNA using this technique (Graham et al., (1973) Virology 52:456–467, incorporated herein by reference).

In an alternative embodiment, a composition of the present invention is introduced into a cell by methods that include particle bombardment. This method depends on the ability to accelerate nucleic acid-coated microprojectiles to a high velocity allowing them to pierce cell membranes and enter cells without killing them. Several devices for accelerating small particles have been developed. One such device relies on a high voltage discharge to generate an electrical current, which in turn provides the motive force. The microprojectiles used have consisted of biologically inert substances such as tungsten or gold beads.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed. and still obtain a like or similar result without departing from the spirit and scope of the present invention.

EXAMPLE 1

Materials and Methods

Human Macrophage Cell Line

This line is obtained from ATCC and is designated U-937. This is a human histiocytic lymphoma cell line and is one of the few human cell lines still expressing many of the monocyte-like characteristics exhibited by cells of histiocytic origin. The cells are readily cultured in RPMI.

Normal Primary Human Bronchial Epithelial Cells

The inventors purchase primary human bronchial cells obtained from a normal human subject from Clonetics (San Diego, Calif.). The cells are maintained in LHC8 medium.

Primary Human Lung Fibroblasts (Normal and IPF)

The inventors have collected, cultured and frozen away lung fibroblasts obtained from 7 patients with IPF and 12 normal lungs. The inventors have early passage specimens available from all of these lines.

Transformed Normal and CF Human Bronchial Epithelial Cells

The inventors will use transformed human bronchial epithelial cells which express wild-type cystic fibrosis transmembrane conductance regulator, CFTR, (BEAS cells, obtained from Dr. Curtis Harris at the National Cancer Institute, Laboratory of Human Carcinogenesis, Bethesda, Md.) or transformed human bronchial epithelial cells expressing mutant CFTR (IB3, obtained from Dr. Pamela Zeitlin at Johns Hopkins University, Baltimore, Md.), The BEAS cell lines were transformed using an adenovirus-12 SV 40 hybrid. The 2CF cells were obtained from human tracheobronchial epithelium and a cell isolation technique was used which enhances recovery of epithelial cells from tracheobronchial submucosal glands. These cells were transformed using an SV 40 plasmid. BEAS cells are grown in LHC-8 media (Biofluids, Rockville, Md., USA) supplemented with penicillin/streptomycin and the cystic fibrosis cell lines are grown in DMEM/F12 (Gibco BRL, Grand Island, N.Y.) supplemented with 10% fetal calf serum, glutamine and penicillin/streptomycin.

ELISA Measurements of IL-6 and IL-8

IL-6 or IL-8 protein in cell culture supernatant is determined using sensitive ELISA kits obtained from R+D systems (Quantikine kit) according to manufacturer's instructions. Basically, samples are dispensed into microtiter wells precoated with murine monoclonal antibody specific for the desired cytokine. The plates are incubated with anti-human IL-6 or IL-8-horseradish peroxidase conjugate, then tetramethylbenzidine and hydrogen peroxide as substrate. The reaction is terminated with a stop buffer and absorbance read at 450 nm. Values of IL-6 or IL-8 are determined by reference to a standard curve Preparation of Cytoplasmic and Nuclear Proteins for Western Blot Cells are removed from culture dishes in solution containing protease and phosphatase inhibitors. After washing, the cells are resuspended in buffer containing the above inhibitors and 0.5% triton to lyse the cells. The suspension is centrifuged at 1000 g×10 min. The supernatant is the cytoplasmic fraction. The nuclear pellet is then lysed with Triton buffer, vortexed, diluted in SDS buffer, boiled×5min. This is the nuclear fraction. Total protein in each fraction is determined by the Bradford method (Bradford, 1976).

Western Blots

Aliquots of nuclear (50 g) or cytoplasmic proteins (100 g) are mixed with an equal volume of 2× sample buffer (containing 0.1% SDS and 2-ME) and boiled for 5 minutes. Denatured proteins are separated by electrophoresis on 5–20% or 10% SDS-polyacrylamide gel along with molecular weight markers and standards. Proteins are transferred to an Immobilon-P membrane in 25 mM Tris base, 192 mM glycine, 5% v/v, methanol pH 8.2, overnight at 40 V. Nonspecific binding is blocked by soaking the membrane in PBS/5% non-fat dried milk with 0.5% Tween 20 for 1 h at room temperature. Immunoreactive proteins are detected by incubating the filter with specific antibodies (anti-C/EBP peptide antibody directed against the 19 amino acid C-terminal peptide—Santa Cruz Biotechnology) for 1 h at room temperature with constant agitation. Nonspecific binding is washed away by rinsing the filter in PBS containing 0.5% Tween 20. The filters are incubated with horseradish peroxidase (HRP) conjugated goat anti-rabbit IgG and detected with Supersignal CL-HRP (for C/EBP) Western Blot luminescent reagent.

Detection of p20 by Immunofluorescence

Cells are grown in special plates containing a central well with glass bottom (Mat-Tek) to confluence and all processing done in the plate. Cells are washed, formalin fixed for 10 min, rewashed ×3 and permeabilized with triton (0.1% triton X 20 min), washed ×3 and blacked with 5% BSA. Fluorescent primary anti-His antibody is then added and the cells incubated for 1 hour, washed ×4 with 0.1% triton buffer, rinsed and Aquamount added. Slides are kept in the dark to dry until ready to view on fluorescent microscope.

EXAMPLE 2

This example demonstrates attenuation of TNFα or IL-1β stimulated production of IL-6 and IL-8 in cell lines relevant to human lung diseases by transfection of a plasmid expression vector containing the gene encoding p20 driven by a CMV promoter (pCMVp20). Cell lines studied include: a human macrophage line, primary and transformed normal human bronchial epithelial cells, transformed human bronchial epithelial cells expressing the cystic fibrosis defect, primary normal human lung fibroblasts, and primary lung fibroblasts from humans with idiopathic pulmonary fibrosis. These cell lines are transfected with pCMV-p20-His (which contains a histidine epitope tag for characterization of expression, see FIG. 11A and Example YYY), pRSV-luc (a control plasmid which expresses the luciferase gene), or no vector. The transfections are carried out in this example using cationic liposome mediated DNA delivery. The expression of p20 by Western blots and immunofluorescence (with a fluorescent antibody to the histidine epitope tag) and the expression of IL-6 and IL-8 in response to stimulation with the proximal cytokines IL-1β and TNFα are determined.

In each study, simultaneous untransfected, control transfected and p20 transfected cells are studied under identical conditions and using identical protocols. Initial studies are done to determine the time course of p20 expression following transfection as well as to estimate the fraction of cells expressing the transgene. Sister wells of cells are transfected with either control or pCMV-p20 vectors and immunofluorescence performed at daily intervals with the fraction of cells showing specific staining counted. At the time of peak p20 expression determined in this way, the inventors harvest cells and isolate cytoplasmic and nuclear protein fractions for Western blotting as an additional determination of transgene expression and to localize the transgene product.

The next series of studies is the determination of IL-6 and IL-8 responses in each of the cell types. In these studies, the inventors measure the effects of a range of concentrations of either TNFα or IL-1 on the production of IL-6 and IL-8 over various time periods as measured by ELISA performed on the medium. Such time periods include 30 minute, 2 hours, 4 hours, 8 hours, 12 hours, 18 hours, 24 hours, 36 hours, 48 hours, and 72 hours. For each cell type, the inventors transfect with either the control plasmid, the pCMVp20 vector or nothing and at the time of peak p20 expression determined above, will add a range of concentrations of TNF or IL-1 to the culture medium, incubate the cells for 24 hours (or another time period) and collect the medium for IL-6 and IL-8 analysis. The concentration range of the proximal cytokines (IL-1β and TNFα is from about 1 pg/ml to about 100 ng/ml).

The inventors find that expression of the p20 gene results in nuclear localization of increased amounts of the p20 protein and that these cells produce less IL-6 or IL-8 when stimulated with proximal cytokines because the p20 inhibits activity of C/EBPβ. The range of IL-6 or IL-8 production in the p20 treated cells is from about 15% less to about 1000 times less IL-6 or IL-8 produced than in the non-p20 treated cells. It is anticipated that pro-inflammatory markers will be suppressed and inflammation will be inhibited in cells derived from other diseases characterized by dysregulated inflammation, in addition to CF and IPF, including ARDS and asthma.

EXAMPLE 3

This example describes methods for delivering the p20 protein intra-cellularly using a liposome delivery system. Delivery of the p20 protein by this method results in the attenuation of TNFα or IL-1β stimulated production of IL-6 and IL-8 in the following cells: a human macrophage line, primary and transformed normal human bronchial epithelial cells, transformed human bronchial epithelial cells expressing the cystic fibrosis defect, primary normal human lung fibroblasts, and primary lung fibroblasts from humans with idiopathic pulmonary fibrosis.

Without being bound to this mechanism, the inventors believe that delivery of the p20 protein into the cytoplasmic compartment of a cell (transfer across the cytoplasmic membrane) results in the subsequent transfer of the p20 protein into the nuclear compartment of the cell because p20 contains nuclear localization signals and normally exists predominantly in the nucleus. Also without being bound to mechanism, the inventors believe that once in the nucleus the transferred p20 binds to C/EBPβ DNA binding sites and inhibits C/EBPβ transcriptional activation. Alternatively, and possibly in combination with the previous mechanism, the p20 may interrupt protein to protein interactions that are involved in the transactivation of pro-inflammatory cytokines or other factors which in turn drive the inflammatory response.

For these studies, the inventors are using a recombinant p20 protein containing a histidine tag so that it can be readily detected by immunofluorescence using an antibody to the histidine tag. There are numerous formulation strategies which might prove effective for delivering p20 as a lipid-protein complex. These could include encapsulation in anionic liposomes, addition of a poly-lysine tail to the p20 protein and creation of a cationic liposome-polylysine-p20 complex by charge-charge interaction, and chemically linking p20 to an appropriate lipid.

Initially two lipid based methods are tested: cationic liposome-p20 mixtures and an anionic liposome containing a surface transferrin as a targeting molecule complexed with p20 by charge-charge interaction. In some circumstances, addition of mixtures of cationic liposomes and cationic protein to cells results in uptake of the protein. Transferrin has been shown to be an active targeting molecule for a number of cell types. In the cell types listed above, the inventors add either anionic liposome-p20 complexes or mixtures of cationic liposomes and p20 in a range of lipid:DNA ratios and measure the delivery of the p20 by performing immunofluorescence on the cultures and counting the percent of positively staining cells. In addition, the inventors harvest cells and determine p20 by Western blot of separated cytoplasmic and nuclear protein fractions. This fluorescent antibody staining technique is used to determine a time course for the nuclear p20 signal and subsequent Western analyses and comparisons of various delivery strategies are then be done at a time of maximum signal.

Exogenous p20 protein, irrelevant protein, and no protein are delivered to each cell type listed above. In certain cases, either IL-1β or TNFα are added at a time that p20 in the nucleus is shown to be at its maximum. The concentrations of IL-6 or IL-8 are measured in the medium of the cells in each experiment at various time points (as above). The inventors find that cells containing exogenous p20 show diminished production of IL-6 or IL-8 when stimulated with proximal cytokines including cells from patients with CF, IPF, ARDS, and asthma. It is anticipated that pro-inflammatory marker will be suppressed and inflammation will be inhibited in cells derived from other diseases characterized by dysregulated inflammation including ARDS and asthma.

In alternative experiments the inventors encapsulate the p20 into anionic liposomes and creation of cationic liposome-polylysine-p20 complexes. Also different lipid-protein ratios and different liposome targeting strategies are tested. In certain experiments, different p20 delivery formulations are used for different cell types. Plus, the experiments are repeated with a recombinant p20 protein that lacks the histidine tag and a recombinant p20 protein made by mammalian cells which provide a p20 protein with full mammalian post-translational processing. Also, non-recombinant p20 is isolated from a natural source such as cultured mammalian cells for certain embodiments in this invention.

EXAMPLE 4

This example describes methods wherein the intracellular delivery and inhibitory activity of p20 are achieved by creating a recombinant fusion protein consisting of p20 and a "membrane translocating sequence" (MTS). An MTS has been described in U.S. Pat. No. 5,807,746 to Lin et al., incorporated herein by reference, to be capable of escorting a protein through the cytoplasmic membrane. The inventors find that a MTS-p20 fusion protein delivers functioning p20 to the nucleus and inhibits TNFα or IL-1β stimulated production of IL-6 and IL-8 in the same cell lines as in Examples 2 and 3.

EXAMPLE 5

In this example, the inventors administer the p20 protein to lung cells in vivo using a MTS-p20 fusion protein strategy. The MTS-p20 fusion protein is made using standard recombinant DNA cloning techniques in which the 3' end of a MTS polynucleotide (for example encoding the polypeptide set forth in SEQ ID NO:12) is ligated to the 5' end of a p20 polynucleotide sequence (SEQ ID NO:4) forming a MTS-p20 recombinant polynucleotide. The MTS-p20 recombinant polynucleotide is cloned into an expression vector by recombinant cloning methods and expressed. The resulting recombinant polypeptide is isolated by standard methods of protein isolation known to one with skill in the art (preferably by Ni-affinity chromatography of an incorporated polyhistidine tag). The recombinant MTS-p20 fusion protein is comprised of a 12-residue MTS (described in U.S. Pat. No. 5,807,746, supra, AAVLLPVLLAAP, SEQ ID NO:12) combined by its C-terminal end to the N-terminal end of the p20 polypeptide (SEQ ID NO:7) forming a MTS-p20 fusion polypeptide. Other combinations of an MTS-p20 fusion protein are also contemplated; such as, p20 being N-terminal to the MTS, or possibly, an MTS being inserted into a p20 polypeptide (or an in-frame insertion into an encoding nucleic acid).

The inventors will produce the recombinant fusion protein as follows. A synthetic oligonucleotide encoding the MTS sequence given above will be inserted into the inventors' expression vector containing the p20 gene at the N-terminal of the coding sequence (pcDNA3.1HisC/EBPβ-3, FIG. 11A). This vector will be used to produce the recombinant fusion protein in $E.\ coli$. The protein will be purified from bacterial cell lysates by Ni-affinity chromatography.

In the cell types listed above, the inventors will add a range of concentrations of the p20-MTS fusion protein and determine that protein is delivered to the cells by performing immunofluorescence and counting the percent of positively staining cells. In addition, the inventors will harvest cells and determine p20 by Western blot of separated cytoplasmic and nuclear protein fractions. In preliminary studies, the inventors will use the fluorescent antibody staining technique to determine a time course for the nuclear p20 signal and subsequent Western analyses will then be done at a time of maximum signal.

Having established that the p20-MTS fusion protein is targeted to the nucleus, the inventors will determine whether cells containing this exogenous p20 show diminished production of IL-6 and IL-8 when stimulated with proximal cytokines. The control studies will include untreated cells and cells which have been exposed to the same concentrations of p20 protein which does not contain the membrane translocation signal. In all cases, either IL-1β or TNFα will be added at a time that p20 in the nucleus was shown to be at its maximum and medium concentrations of IL-6 and IL-8 measured after 24 hours incubation.

The inventors anticipate that the p20-MTS fusion protein will effectively deliver p20 to the cells, that it will localize in the nucleus, inhibit transactivation activity of C/EBPβ and thus attenuate TNF or IL-1 stimulated production of IL-8 and IL-6. Although the MTS has been shown capable of delivering even larger proteins to cells, it is possible that that will not be the case for the inventors' cell preparations and p20. It is also possible that addition of MTS sequences to the p20 protein will mask nuclear localization signals and thus that the fusion protein will enter the cell but remain in the cytoplasm and thus not function to inhibit C/EBPβ. The inventors should know this from the immunofluorescence localization studies. This is not expected, though, as the inventors have predicted the location of two bipartite NLSs in p20 (FIG. 5) and these should not be affected by a terminal fusion protein. It is also possible that the fusion protein will enter the nucleus but not bind appropriately to DNA and therefore not serve as an inhibitor of C/EBPβ. In either of these cases, the inventors would place the MTS sequences on the end of the p20 gene encoding the C terminal sequence and repeat the experiments. In any event, the present invention is not bound by mechanism and it is determined herein that expression of p20 in cells stimulated by an inflammatory agent, inhibits the inflammatory response.

EXAMPLE 6

In this example, the inventors describe the construction of a hybrid retrovirus/Epstein Barr virus (hybrid retro/EBV) expression vector with a p20 insert. The vector with insert is referred to as pLZRSHis-C/EBPβ-3 or pLZRSHis-p20 (see FIGS. 11A–C). To obtain LZRS vector encoding epitope-tagged C/EBPβ-3, prsetALip plasmid (including the p20 sequence) is digested with Bam HI and Eco RI restriction endonucleases followed by gel electrophoresis and isolation of a 575 basepair p20 fragment. The p20 fragment is ligated into a similarly digested (Bam HI and Eco RI) pcDNA3.1HisC vector to generate pcDNA3.1His-p20 plasmid (FIG. 11A). This vector is then digested with Hin DIII/Not I restriction endonucleases followed by gel electrophoresis and isolation of a 711 basepair His-tagged p20 fragment. The pLZRSpBMN-Z plasmid is digested with Hin DIII/Not I also. A 11,452 basepair fragment is isolated and ligated to the 711 basepair His-tagged C/EBPβ-3 fragment to generate pLZRS-His-C/EBPβ-3 (FIG. 11B). Again the control vector contains the β-galactosidase gene. A diagram of the pLZRS-His-p20 vector is shown in FIG. 11C.

Helper-free retrovirus is obtained by transfecting the pLZRShis-p20 vector, or control LZRSpBMN-Z vector encoding β-galactosidase, into a 293T-based amphotropic packaging cell line termed φnx-ampho (provided by Gary Nolan, Stanford University, California, USA). These methods are known to those of skill in the art. Briefly, 1 μg of pLZRShis-p20 vector or 1 μg of LZRSpBMN-Z vector is transfected into the φnx-ampho cells using GenePorter liposome reagent according to the manufacture's directions. Transfected cells were maintained in puromycin to select for episomal maintenance of the transfected vector.

High titre virus is collected as follows. Three weeks prior to performing transfections, (φ)nx-ampho cells are reselected in the presence of diphtheria toxin and hygromycin B to increase envelope and gag-pol expression. Packaging cells are then transfected by standard calcium phosphate procedures, and viral supernatants (in culture medium) are harvested at 48 hours post-transfection, clarified, and stored frozen at 800 C. Cells are then trypsinized and replated in medium containing puromycin (to select for episomal maintenance of the LZRS-based construct). Upon reaching 70% confluence, cells are placed in puromycin free medium for 24 hrs prior to harvesting virus as before. This procedure is carried out for production and collection of viral stocks for up to 3 weeks post-transfection. For general reference, see, Nolan et al. (1998) Expression vectors and delivery systems. Curr. Opin. Biotechnol. 9, 447–450 and Grignani et al. (1998) High efficiency gene transfer and selection of human hematopoietic progenitor cells with a hybrid EBV/retroviral vector expressing the green fluorescence protein Cancer Res. 58, 14–19; each reference incorporated herein by reference. High titer, helper free C/EBPβ-3 retrovirus can be collected for about the first week after transfection.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. It will be apparent, also, that certain agents which are both chemically and physiologically related may be substituted for the agents described herein while the same or similar results would be achieved. All such similar substitutes and modifications apparent to those skilled in the art are deemed to be within the spirit, scope and concept of the invention as defined in the claims.

EXAMPLE 7

In this example, the inventors describe the construction of an epitope tagged C/EBPβ-1 retroviral vector with a mutation in the C/EBPβ-2 translation initiation site (the second in-frame ATG described in FIG. 3A). A hybrid Epstein-Barr virus (EBV)/retroviral vector construct, LZRSpBMN-Z, is provided by Gary P. Nolan (Stanford University, California, USA). The LZRSpBMN-Z is described in U.S. Pat. No. 5,830,725 to Nolan et al., incorporated herein by reference. The LZRSpBMN-Z vector features episomal replication which enables production of high titer virus and high efficiency gene transfer. In addition to a murine retroviral backbone with a polylinker region to facilitate insertion of cDNAs, the LZRSpBMN-Z vector contains the Epstein-Barr virus Nuclear Antigen (EBNA) gene, EBV origin of replication and nuclear retention sequences (oriP), and a puromycin resistance gene. The nuclear replication and retention function of this vector allow for rapid establishment of recombinant retroviral producer DNA as stable episomes within human retroviral packaging cell lines. Episomes are maintained at approximately 5–20 copies per cell for up to 2–3 months, given selection for puromycin resistance, resulting in high viral titers. The retroviral backbone in this vector consists of full-length Moloney murine leukemia virus (MoMLV) long terminal repeat (LTR) and extended ψ packaging sequences derived from the MFG series of retroviral vectors developed by Mulligan and colleagues.

To obtain LZRS vector encoding epitope-tagged C/EBPβ-1, the β-galactosidase gene encoded by the prototype LZR-SpBMN-Z vector is excised and replaced with his-tagged C/EBPβ-1 fragments to generate a pLZRShisC/EBPβ-1 vector. The construction of the pLZRShisC/EBPβ-1 vector is completed in several steps (FIGS. 11D–G). First a CMV-NFIL6 vector is digested with Sal I, incubated at 4 C with DNA Polymerase I to generate blunt ends, and digested with Eco RI to release a 1,045 basepair fragment containing C/EBPβ-1 from CMV-NFIL6. In this case the CMV-NFIL6 vector was obtained from S. Akira. However, a clone of C/EBPβ-1 can be obtained using standard methods known to one with skill in the art from a cDNA library or genomic DNA. Next, the 1,045 basepair fragment is inserted into the pRSETC vector (available from InVitrogen, San Diego, Calif., USA) for mutagenesis and to acquire the polyhistidine epitope tag which is included in the pRSETC vector (FIG. 11D). The pRSETC vector is digested with Hind III, incubated at 4 C with DNA Polymerase I, and digested by Eco RI, and the 1,045 basepair C/EBPβ-1 fragment is ligated into place forming the pRSETC-C/EBPβ (which is also called pRSETC-NFIL6) (FIG. 11D). Mutagenesis is conducted by replacing a 106 basepair Bgl II to Msc I fragment of the pRSETC-C/EBPβ-1 vector with synthetic oligos (commercially available) shown in FIG 11E. The top strand oligo is listed in SEQ ID NO:21. The bottom strand oligo is listed in SEQ ID NO:22. Several mutations in the top strand oligonucleotide create a Kozak sequence and are underlined in FIG. 11E and run from about position 293 to 302. The mutant residues eliminating the ATG for C/EBPβ-2 expression are underlined, also, in FIG. 11E at approximately positions 368 and 369. The mutations can be compared to the wild-type C/EBPβ sequence for this region as shown in FIG. 11E, also. FIG. 11F shows that cloning of the epitope tagged C/EBPβ-1 with Kozak and C/EBPβ-2 elimination mutations from pcDNA3.1HisAC/EBPβ-1 into pLZRSpBMN-Z forming the pLZRS-His-C/EBPβ-1 vector. FIG. 11G shows a diagram of the LZRS vector with an epitope-tagged C/EBPβ-1 insert (pLZRShisC/EBPβ-1). Control vector would remain unchanged and contain a β-galactosidase encoding sequence. Similar methods can be used to ensure selective expression of p20 by mutating the C/EBPβ-2 and/or C/EBPβ-1 translation start site and creating a Kozak sequence at the C/EBPβ-3 translation initiation site.

EXAMPLE 8

Figure 9A:
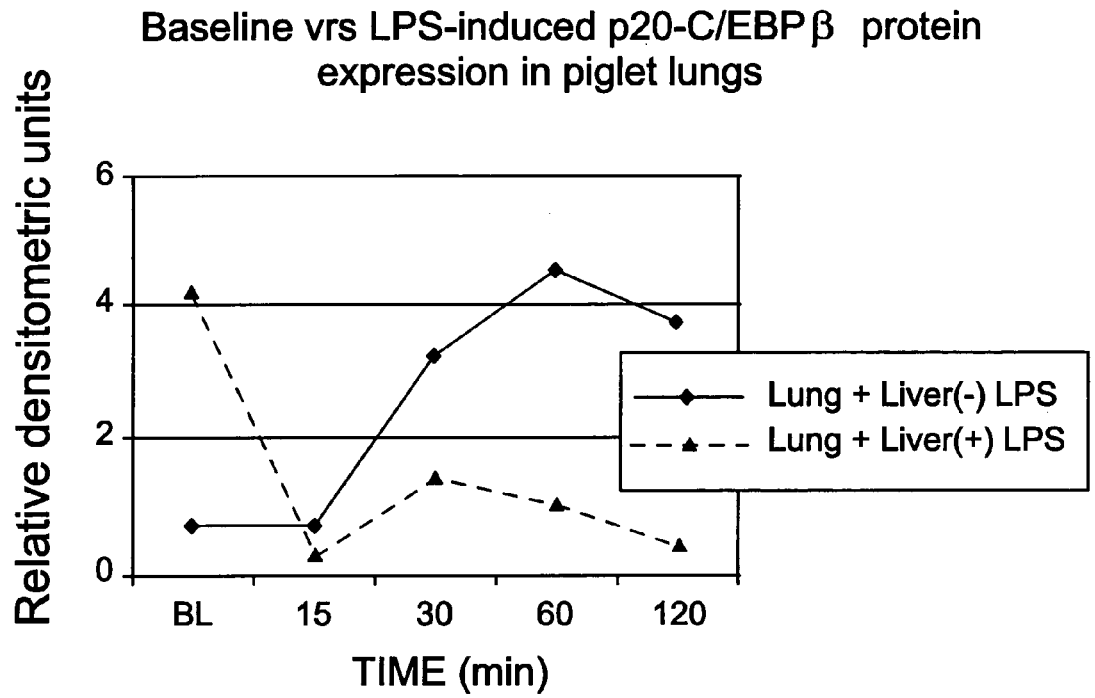
FIG. 9A is a graph showing the change in p20 (C/EBPβ-3) expression over time in piglet lungs following perfusion of the piglet lungs and liver with and without endotoxin (lipopolysaccharide, LPS). The p20 values are relative densitometric units determined by densitometric scans of autoradiographs of Western blots.

In this example, the inventors describe the effects of in vivo lipopolysaccharide (endotoxin) administration to piglets on p20 and p42 expression, wherein the lung and liver are placed in a perfusion circuit (optionally, the lung or the liver can be placed in a perfusion circuit independently). As seen in FIG. 9A, p20 expression in piglet lung tissue is increased in the control which is perfused, but not stimulated with LPS. This increase in p20 expression is believed to be the normal physiological response to an inflammatory stimulus, in this case, mechanical stress. The administration of LPS to the perfusion, however, shows a rapid decline in p20 expression over to essentially no expression within 15 minutes. These data suggest that endotoxin has a physiological mechanism for overcoming a normal response to inflammation and may explain some of the pathological activity of endotoxin (a prevention to the down regulation of the inflammatory response).

Figure 9B:
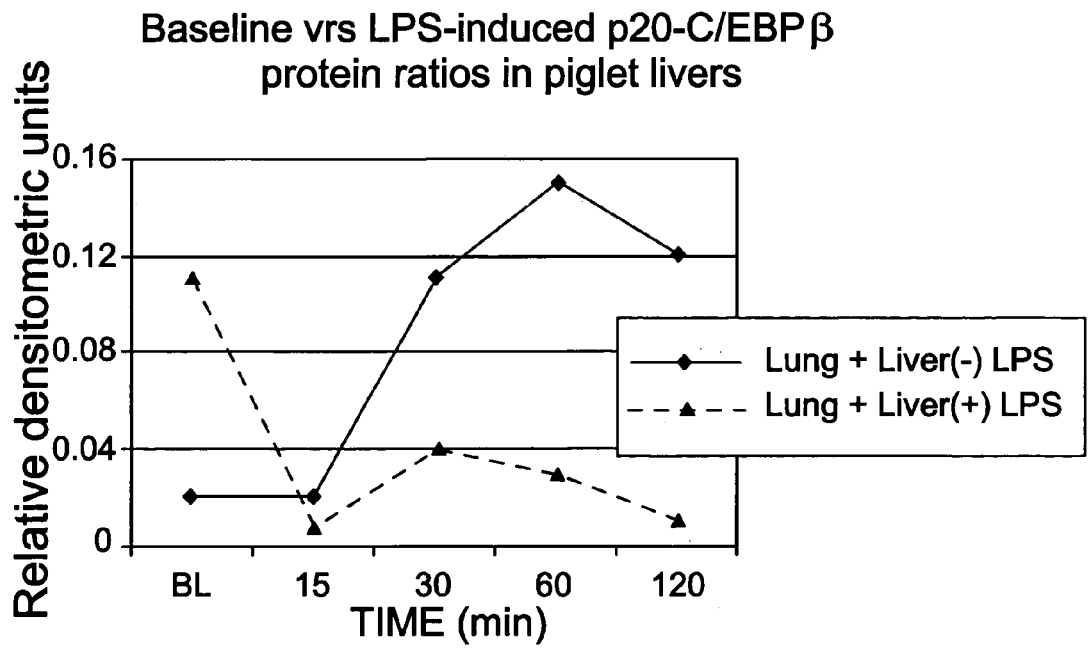
FIG. 9B is a graph showing the change in p20:p42 ratio over time in piglet lungs following perfusion of the piglet lungs and liver with and without endotoxin (lipopolysaccharide, LPS). The p20 values are relative densitometric units determined by densitometric scans of autoradiographs of Western blots.

The data in FIG. 9B show the relative ration of p20 to p42 expression in piglet lung tissue following (+/-) treatment with LPS (as above). (The data in each case are reported in relative densitometric units from scans of Western blots.) An increase in the p20 to p42 ratio is observed for the normal case following a pro-inflammatory stimulus (mechanical stress from the perfusion). A decrease in p20 to p42 ratio is observed in piglet lung tissue if LPS is administered (FIG. 9B). In conclusion, an increase in p20 expression and possibly an increase in the p20 to p42 ratio is a normal physiological response to an inflammatory stimulus. Certain inflammatory stimuli, such as endotoxin, which are associated with a hyper-reactive inflammatory response; are able to overcome the normal cellular safeguards which defuse the response. Therefore, in certain embodiments of the present invention, p20 (protein or encoded in a nucleic acid for expression) is used to inhibit or prevent an inflammation associated with an agent that overwhelms the cellular defenses to hyper-reactive inflammation.

EXAMPLE 9

In this example, the inventors describe one method for generation of a membrane permeable fusion protein, specifically a glutathione S-transferase (marker/reporter) plus p20 plus membrane transport sequence fusion polypeptide (GST-p20-MTS).

Using the sequence of C/EBPβ protein, described by Akira et al (GeneBank record:NM005194) the primers p20-1 and p20-2 were designed. The sequences are:

p20-1 (CCGGATCCCCATGGCGGGCTTCCCGTACGCGCTGCGC, SEQ ID NO:23)

and P20-2 (CCGGATCCCGCAGTGGCCGGAGGAGGCGAGCAGGGGCTC, SEQ ID NO:24).

Using cDNA of C/EBPβ protein provided by GeneRx+, Nashville, Tenn.; cDNA corresponding to the p20 protein was amplified by PCR (amino acids 596–1035 of the supplied C/EBPβ cDNA vector).

| PCR protocol: | |
|---|---|
| Reaction: | |
| 10 × Taq buffer | 5 ul |
| MgCl$_2$ 25 mM | 2 ul |
| p20-1 primer (10 uM) | 2.5 ul |
| p20-2 primer (10 uM) | 2.5 ul |
| cDNA (1 ng/ml) | 10 ul |
| dNTP (2.5 mM each) | 8 ul |
| Taq polymerase | 1 ul |
| Program: | |
| 95° C. × 5 min | |
| 65° C. × 2 min | 1 cycle |
| 72° C. × 2 min | |
| 95° C. × 1 min | |
| 65° C. × 2 min | 35 cycles |
| 72° C. × 2 min | |
| 4° C. × 8 hours | 1 cycle. |

Purification of PCR Product:

A 1% agarose gel, band corresponding to the PCR product was cut and cDNA purified using a Qiagen agarose extraction Kit.

Cloning PCR Fragment into pGEM-T Easy Vector:

| Ligation: | |
|---|---|
| 2 × rapid ligation buffer | 5 ul |
| Vector pGEM-T easy | 1 ul |
| PCR product | 4 ul |
| T4 DNA ligase | 3 ul |

Overnight reaction at 4 C

Plasmid Transformed into DH5α Bacteria:

Mini-preps and digestion with Bam-H1 from transformation were performed using techniques standard in the art, one clone (identified as #7) was positive for the insert. The plasmid pGEMT-p20 Midi-prep total yield was 300 ug/ml (in 1 ml).

The cDNA was digested with BamH1 restriction endonuclease and gel purified yielding a BamH1-BamH1 p20 cDNA.

Ligation of the Bam H1 Digested p20 Fragment into MTS-2 Vector (Provided by GeneRx+, Inc.:

| MTS-2 vector (BamH1/BamH1) CIP treated | 2 ul |
|---|---|
| P20 insert (BamH1/BamH1) | 2 ul |
| T4 DNA ligase Buffer | 1 ul |
| T4 DNA ligase | 1 ul |
| Water | 4 ul |

Reaction was incubated overnight at 18 C

Transformation into BL-21 Bacteria:

Mini-preps and digestion (Bstw-1/EcoR1) to identify colonies that are positive for the fusion insert and which have the insert in the right orientation were performed. A protein expression assay was carried out in four different clones that were positive by the restriction assay above, including non-permeable GST-p20. All were positive. Coomassie stain and Western blot analysis using and anti-C/EBPβ antibody (against COO terminal) confirmed this.

Protein Purification Using Glutathione Agarose Gel:

Bacteria strain BL-21(DE-3)RP was transformed with MTS-2-p20 plasmids for fusion polypeptide expression. Mini-preps and digestion (Bstw-1/EcoR1) were carried out to identify colonies that have the insert and which have the insert in the right orientation. Protein expression assays in four different clones, including non-permeable GST-p20 were all positive.

Import Assay:

An import assay (see Example 9) was performed to identify and/or quantify importation of MTS-linked polypeptide into mammalian cells. The protein was visualized by in-direct immunofluorescence in NIH3T3 cells (see FIG. 14).

EXAMPLE 9

Import Assay

NIH 3T3 cells were incubated with MTS-p20 fusion polypeptide and p20 polypeptide without an MTS at protein concentrations of approximately 50 μg protein/ml of culture medium. The MTS-p20 and the p20 both included a his tag for purification (see Example 8). After 1 hour, cells were stained with either nucleic acid stain or with antibody against p20 protein (C-terminal). Only cells incubated with MTS-p20 showed abundant presence of the p20 protein in the nucleus of the cell (see FIG. 14, p20 includes a strong nuclear transport signal).

What is claimed is:

1. A method of treating an inflammation in a lung of a mammal in need thereof, wherein the inflammation involves C/EBPβ-mediated transcription of a gene encoding an inflammatory mediator, comprising administering a therapeutically effective amount of an isolated nucleic acid including a sequence encoding a p20 polypeptide to a cell of the mammal and expressing the p20 polypeptide in the cell, wherein the p20 polypeptide comprises the amino acid sequence set forth in SEQ ID NO: 7, the amino acid sequence set forth in amino acid positions 152 to 296 of SEQ ID NO: 9, or the amino acid sequence set forth in amino acid positions 153 to 297 of SEQ ID NO: 11, thereby treating the inflammation in a lung of the mammal.

2. A method of treating an inflammation in a lung of a mammal in need thereof, wherein the inflammation involves C/EBPβ-mediated transcription of a gene encoding an inflammatory mediator, comprising administering a therapeutically effective amount of the isolated nucleic acid including a sequence encoding a p20 polypeptide to an ex vivo cell from the mammal wherein the p20 polypeptide comprises the amino acid sequence set forth in SEQ ID NO: 7, the amino acid sequence set forth in amino acid positions 152 to 296 of SEQ ID NO: 9, or the amino acid sequence set forth in amino acid positions 153 to 297 of SEQ ID NO: 11 and administering the ex vivo cell to the mammal, thereby treating the inflammation in a lung of the mammal.

3. A method of treating an inflammation in a lung of a mammal in need thereof, wherein the inflammation involves C/EBPβ-mediated transcription of a gene encoding an inflammatory mediator, comprising:

(a) mixing an isolated polynucleotide encoding a p20 polypeptide, wherein the p20 polypeptide comprises the amino acid sequence set forth in SEQ ID NO: 7, the amino acid sequence set forth in amino acid positions 152 to 296 of SEQ ID NO: 9, or the amino acid sequence set forth in amino acid positions 153 to 297 of SEQ ID NO: 11, with a pharmaceutically acceptable carrier to form a pharmaceutical composition, wherein the polynucleotide is capable of expressing the p20 polypeptide in a cell that is from the mammal; and (b) administering a therapeutically effective amount of the mixture from step (a) to the mammal.

4. The method of claim 3, wherein the pharmaceutically acceptable carrier includes a liposome.

5. The method of claim 3, wherein the mixture of step (a) is administered to the mammal by removing a cell from the mammal, introducing the mixture to the cell and providing the cell to the mammal.

6. The method of claim 3, wherein the inflammation comprises a symptom of a disease selected from a group consisting of: adult respiratory distress syndrome, asthma, bronchitis, bronchopulmonary dysplasia, cystic fibrosis, extensive allergic alveolitis, idiopathic pulmonary fibrosis, interstitial lung disease, and respiratory viral infection.

7. The method of claim 3, wherein the p20 polypeptide includes the amino acid sequence as set forth in SEQ ID NO: 15 or the polynucleotide includes a segment encoding the amino acid sequence as set forth in SEQ ID NO: 15.

8. A method of treating inflammation in a lung caused or exacerbated by an increased activity of a pro-inflammatory mediator in a mammal in need thereof, wherein the disease involves C/EBPβ-mediated transcription of a gene encoding an inflammatory mediator, comprising administering, to a cell in a mammal, a therapeutically effective amount of an isolated polynucleotide encoding a p20 polypeptide, wherein the p20 polypeptide comprises the amino acid sequence set forth in SEQ ID NO: 7, the amino acid sequence set forth in amino acid positions 152 to 296 of SEQ ID NO: 9, or the amino acid sequence set forth in amino acid positions 153 to 297 of SEQ ID NO: 11.

9. A method of inhibiting expression of an inflammatory mediator in a cell in a lung of a mammal, wherein C/EBPβ mediates transcription of a gene encoding the inflammatory mediator, comprising administering to the cell, in an amount effective to inhibit the expression of the inflammatory mediator, an isolated polynucleotide encoding a p20 polypeptide, wherein the p20 polypeptide comprises the amino acid sequence set forth in SEQ ID NO: 7, the amino acid sequence set forth in amino acid positions 152 to 296 of SEQ ID NO: 9, or the amino acid sequence set forth in amino acid positions 153 to 297 of SEQ ID NO: 11.

10. A composition comprising: an expression vector including an expression insert and at least one genetic element operably linked to the insert, wherein the expression insert includes a region encoding a membrane transport sequence and a polynucleotide segment encoding a p20 polypeptide, wherein the p20 polypeptide comprises the amino acid sequence set forth in SEQ ID NO: 7, the amino acid sequence set forth in amino acid positions 152 to 296 of SEQ ID NO: 9, or the amino acid sequence set forth in amino acid positions 153 to 297 of SEQ ID NO: 11.

11. The composition of claim 10, wherein the genetic element is selected from a group consisting of: a promoter, an internal ribosome entry site, a Kozak sequence, a translation initiation codon, an enhancer, and a polyadenylation signal.

12. The composition of claim 10, wherein the polynucleotide segment comprises SEQ ID NO:4.

13. The composition of claim 10, wherein the polynucleotide segment hybridizes to SEQ ID NO:4 or the complement of SEQ ID NO:4 under high stringency hybridization conditions.

14. A method of manufacturing a membrane transport sequence-p20 (MTS-p20) fusion polypeptide, comprising:
   a) providing an expression vector including an expression insert and at least one genetic element operably linked to the insert, wherein the expression insert includes a region encoding a membrane transport sequence and a polynucleotide segment encoding a p20 polypeptide, wherein the p20 polypeptide comprises the amino acid sequence set forth in SEQ ID NO: 7, the amino acid sequence set forth in amino acid positions 152 to 296 of SEQ ID NO: 9, or the amino acid sequence set forth in amino acid positions 153 to 297 of SEQ ID NO: 11,
   b) expressing the MTS-p20 polypeptide in a cultured cell; and
   c) purifying the MTS-p20 polypeptide.

15. The method of claim 14, wherein the expression insert further includes a purification tag.

16. The method of claim 1, wherein the inflammation comprises a symptom of a disease selected from a group consisting of: adult respiratory distress syndrome, asthma, bronchitis, bronchopulmonary dysplasia, cystic fibrosis, extensive allergic alveolitis, idiopathic pulmonary fibrosis, interstitial lung disease, and respiratory viral infection.

* * * * *

SEQUENCE LISTING

<160> NUMBER OF SEQ ID NOS: 33

<210> SEQ ID NO 1
<211> LENGTH: 1910
<212> TYPE: DNA
<213> ORGANISM: Homo sapiens
<220> FEATURE:
<221> NAME/KEY: modified_base
<222> LOCATION: (1)..(1910)
<223> OTHER INFORMATION: "n" represents a, t, c or g

<400> SEQUENCE: 1

| | |
|---|---|
| gtccttcgcg tcccggcggc gcggcggagg ggccggcgtg acgcagcggt tgctacgggc | 60 |
| cgcccttata aataaccggg ctcaggagaa actttagcga gtcagagccg cgcacgggac | 120 |
| tgggaagggg acccacccga gggtccagcc accagccccc tcactaatag cggccacccc | 180 |
| ggcagcggcg gcagcagcag cagcgacgca gcggcgacag ctcagagcag ggaggccgcg | 240 |
| cacctgcggg ccggccggag cgggcagccc caggcccct ccccgggcac ccgcgttcat | 300 |
| gcaacgcctg gtggcctggg acccagcatg tctcccctg ccgccgccgc cgcctgcctt | 360 |
| taaatccatg gaagtggcca acttctacta cgaggcggac tgcttggctg ctgcgtacgg | 420 |
| cggcaaggcg gccccgcgg cgcccccgc ggccagaccc gggccgcgcc ccccgccgg | 480 |
| cgagctgggc agcatcggcg accacgagcg cgccatcgac ttcagcccgt acctggagcc | 540 |
| gctgggcgcg ccgcaggccc cggcgcccgc cacggccacg gacaccttcg aggcggctcc | 600 |
| gcccgcgccc gcccccgcgc ccgcctcctc cgggcagcac cacgacttcc tctccgacct | 660 |
| cttctccgac gactacgggg gcaagaactg caagaagccg gccgagtacg gctacgtgag | 720 |
| cctggggcgc ctggggctg ccaagggcgc gctgcacccc ggctgcttcg cgcccctgca | 780 |
| cccaccgccc ccgccgccgc cgccgcccgc cgagctcaag gcggagccgg gcttcgagcc | 840 |
| cgcggactgc aagcggaagg aggaggccgg ggcgccgggc ggcggcgcag gcatggcggc | 900 |
| gggcttcccg tacgcgctgc gcgcttacct cggctaccag gcggtgccga gcggcagcag | 960 |
| cgggagcctc tccacgtcct cctcgtccag cccgcccggc acgccgagcc ccgctgacgc | 1020 |
| caaggccccc ccgaccgcct gctacgcggg ggccgggccg gcgccctcgc aggtcaagag | 1080 |
| caaggccaag aagaccgtgg acaagcacag cgacgagtac aagatccggc gcgagcgcaa | 1140 |
| caacatcgcc gtgcgcaaga gccgcgacaa ggccaagatg cgcaacctgg agacgcagca | 1200 |
| caaggtcctg gagctcacgg ccgagaacga gcggctgcaa aagaaggtgg agcagctgtc | 1260 |
| gcgcgagctc agcaccctgc ggaacttgtt caagcagctg cccgagcccc tgctcgcctc | 1320 |
| ctccggccac tgctagcgcg gccccgcgg cgtcccctg gggccggccg gggctgagac | 1380 |
| tccggggagc gcccgcgccc gcgccctcgc ccccncccc nnnnccgcaa aactttggca | 1440 |
| ctggggcact tggcagcngg ggagcccgtc ggtaatttta atattttatt atatatatat | 1500 |
| atctatattt tgccaaccaa ccgtacatgc agatggctcc cgcccgtggt gtataaagaa | 1560 |
| gaaatgtcta tgtgtacaga tgaatgataa actctctgct ctccctctgc ccctctccag | 1620 |
| gcccggcggg cggggccggt ttcgaagttg atgcaatcgg tttaaacatg gctgaacgcg | 1680 |
| tgtgtacacg ggactgacgc aacccacgtg taactgtcag ccgggccctg agtaatcgct | 1740 |
| taaagatgtt ctagggcttg ttgctgttga tgttttgttt tgttttgttt tttggtcttt | 1800 |
| ttttgtatta taaaaaataa tctatttcta tgagaaaaga ggcgtctgta tattttggga | 1860 |
| atcttttccg tttcaagcaa ttaagaacac ttttaataaa ctttttttg | 1910 |

<210> SEQ ID NO 2
<211> LENGTH: 1038
<212> TYPE: DNA
<213> ORGANISM: Homo sapiens

<400> SEQUENCE: 2

| | |
|---|---|
| atgcaacgcc tggtggcctg ggacccagca tgtctccccc tgccgccgcc gccgcctgcc | 60 |

-continued

```
tttaaatcca tggaagtggc caacttctac tacgaggcgg actgcttggc tgctgcgtac    120
ggcggcaagg cggccccccgc ggcgccccccc gcggccagac ccgggccgcg cccccccgcc    180
ggcgagctgg gcagcatcgg cgaccacgag cgcgccatcg acttcagccc gtacctggag    240
ccgctgggcg cgccgcaggc cccggcgccc gccacggcca cggacaccttt cgaggcggct    300 ccgcccgcgc cgcccccgc gcccgcctcc tccgggcagc accacgactt cctctccgac    360
ctcttctccg acgactacgg gggcaagaac tgcaagaagc cggccgagta cggctacgtg    420
agcctggggc gcctggggcc tgccaagggc gcgctgcacc ccggctgctt cgcgcccctg    480
cacccaccgc ccccgccgcc gccgccgccc gccgagctca aggcggagcc gggcttcgag    540
cccgcggact gcaagcggaa ggaggaggcc ggggcgccgg gcggcggcgc aggcatggcg    600
gcgggcttcc cgtacgcgct gcgcgcttac ctcggctacc aggcggtgcc gagcggcagc    660
agcgggagcc tctccacgtc ctcctcgtcc agcccgcccg gcacgccgag ccccgctgac    720
gccaaggccc cccgaccgc ctgctacgcg ggggccgggc cggcgccctc gcaggtcaag    780
agcaaggcca agaagaccgt ggacaagcac agcgacgagt acaagatccg gcgcgagcgc    840
aacaacatcg ccgtgcgcaa gagccgcgac aaggccaaga tgcgcaacct ggagacgcag    900
cacaaggtcc tggagctcac ggccgagaac gagcggctgc agaagaaggt ggagcagctg    960
tcgcgcgagc tcagcaccct gcggaacttg ttcaagcagc tgcccgagcc cctgctcgcc   1020
tcctccggcc actgctag                                                  1038
```

```
<210> SEQ ID NO 3
<211> LENGTH: 969
<212> TYPE: DNA
<213> ORGANISM: Homo sapiens

<400> SEQUENCE: 3
atggaagtgg ccaacttcta ctacgaggcg gactgcttgg ctgctgcgta cggcggcaag     60 gcggccccccg cggcgccccc cgcggccaga cccgggccgc gccccccgc cggcgagctg    120 ggcagcatcg cgaccacga gcgcgccatc gacttcagcc cgtacctgga ccgctgggc    180 gcgccgcagg ccccggcgcc cgccacggcc acggacacct tcgaggcggc tccgcccgcg    240
cccgcccccg cgcccgcctc ctccgggcag caccacgact tcctctccga cctcttctcc    300
gacgactacg ggggcaagaa ctgcaagaag ccggccgagt acggctacgt gagcctgggg    360
cgcctggggg ctgccaaggg cgcgctgcac cccggctgct tcgcgcccct gcacccaccg    420
cccccgccgc cgccgccgcc cgccgagctc aaggcggagc cgggcttcga gcccgcggac    480
tgcaagcgga aggaggaggc cggggcgccg ggcggcggcg caggcatggc ggcgggcttc    540
ccgtacgcgc tgcgcgctta cctcggctac caggcggtgc cgagcggcag cagcgggagc    600
ctctccacgt cctcctcgtc cagcccgccc ggcacgccga ccccgctga cgccaaggcc    660 cccccgaccg cctgctacgc ggggggccggg ccggcgccct cgcaggtcaa gagcaaggcc    720
aagaagaccg tggacaagca cagcgacgag tacaagatcc ggcgcgagcg caacaacatc    780
gccgtgcgca agagccgcga caaggccaag atgcgcaacc tggagacgca gcacaaggtc    840
ctggagctca cggccgagaa cgagcggctg cagaagaagg tggagcagct gtcgcgcgag    900
ctcagcaccc tgcggaactt gttcaagcag ctgcccgagc cctgctcgc ctcctccggc    960 cactgctag                                                             969
```

```
<210> SEQ ID NO 4
```

```
<211> LENGTH: 444
<212> TYPE: DNA
<213> ORGANISM: Homo sapiens

<400> SEQUENCE: 4
atggcggcgg gcttcccgta cgcgctgcgc gcttacctcg ctaccaggc ggtgccgagc      60 ggcagcagcg ggagcctctc cacgtcctcc tcgtccagcc cgcccggcac gccgagcccc    120
gctgacgcca aggcccccccc gaccgcctgc tacgcggggg ccgggccggc gccctcgcag    180
gtcaagagca aggccaagaa gaccgtggac aagcacagcg acgagtacaa gatccggcgc    240
gagcgcaaca acatcgccgt gcgcaagagc cgcgacaagg ccaagatgcg caacctggag    300
acgcagcaca ggtcctgga gctcacggcc gagaacgagc ggctgcagaa gaaggtggag    360
cagctgtcgc gcgagctcag caccctgcgg aacttgttca gcagctgcc cgagcccctg    420 ctcgcctcct ccggccactg ctag                                           444
<210> SEQ ID NO 5
<211> LENGTH: 345
<212> TYPE: PRT
<213> ORGANISM: Homo sapiens

<400> SEQUENCE: 5

Met Gln Arg Leu Val Ala Trp Asp Pro Ala Cys Leu Pro Leu Pro Pro
  1               5                  10                  15

Pro Pro Pro Ala Phe Lys Ser Met Glu Val Ala Asn Phe Tyr Tyr Glu
                 20                  25                  30

Ala Asp Cys Leu Ala Ala Ala Tyr Gly Gly Lys Ala Ala Pro Ala Ala
             35                  40                  45

Pro Pro Ala Ala Arg Pro Gly Pro Arg Pro Pro Ala Gly Glu Leu Gly
         50                  55                  60

Ser Ile Gly Asp His Glu Arg Ala Ile Asp Phe Ser Pro Tyr Leu Glu
 65                  70                  75                  80

Pro Leu Gly Ala Pro Gln Ala Pro Ala Pro Ala Thr Ala Thr Asp Thr
                 85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
        115                 120                 125

Lys Asn Cys Lys Lys Pro Ala Glu Tyr Gly Tyr Val Ser Leu Gly Arg
    130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
                165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
        195                 200                 205

Ala Tyr Leu Gly Tyr Gln Ala Val Pro Ser Gly Ser Ser Gly Ser Leu
    210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Gly Pro Ala Pro
                245                 250                 255

Ser Gln Val Lys Ser Lys Ala Lys Lys Thr Val Asp Lys His Ser Asp
            260                 265                 270
```

-continued

Glu Tyr Lys Ile Arg Arg Glu Arg Asn Asn Ile Ala Val Arg Lys Ser
            275                 280                 285

Arg Asp Lys Ala Lys Met Arg Asn Leu Glu Thr Gln His Lys Val Leu
290                 295                 300

Glu Leu Thr Ala Glu Asn Glu Arg Leu Gln Lys Val Glu Gln Leu
305                 310                 315                 320

Ser Arg Glu Leu Ser Thr Leu Arg Asn Leu Phe Lys Gln Leu Pro Glu
            325                 330                 335

Pro Leu Leu Ala Ser Ser Gly His Cys
            340                 345

<210> SEQ ID NO 6
<211> LENGTH: 322
<212> TYPE: PRT
<213> ORGANISM: Homo sapiens

<400> SEQUENCE: 6

Met Glu Val Ala Asn Phe Tyr Tyr Glu Ala Asp Cys Leu Ala Ala Ala
 1               5                  10                  15

Tyr Gly Gly Lys Ala Ala Pro Ala Ala Pro Ala Ala Arg Pro Gly
            20                  25                  30

Pro Arg Pro Pro Ala Gly Glu Leu Gly Ser Ile Gly Asp His Glu Arg
            35                  40                  45

Ala Ile Asp Phe Ser Pro Tyr Leu Glu Pro Leu Gly Ala Pro Gln Ala
        50                  55                  60

Pro Ala Pro Ala Thr Ala Thr Asp Thr Phe Glu Ala Ala Pro Pro Ala
65                  70                  75                  80

Pro Ala Pro Ala Pro Ala Ser Ser Gly Gln His His Asp Phe Leu Ser
                85                  90                  95

Asp Leu Phe Ser Asp Asp Tyr Gly Gly Lys Asn Cys Lys Lys Pro Ala
                100                 105                 110

Glu Tyr Gly Tyr Val Ser Leu Gly Arg Leu Gly Ala Ala Lys Gly Ala
            115                 120                 125

Leu His Pro Gly Cys Phe Ala Pro Leu His Pro Pro Pro Pro Pro Pro
130                 135                 140

Pro Pro Pro Ala Glu Leu Lys Ala Glu Pro Gly Phe Glu Pro Ala Asp
145                 150                 155                 160

Cys Lys Arg Lys Glu Glu Ala Gly Ala Pro Gly Gly Gly Ala Gly Met
                165                 170                 175

Ala Ala Gly Phe Pro Tyr Ala Leu Arg Ala Tyr Leu Gly Tyr Gln Ala
            180                 185                 190

Val Pro Ser Gly Ser Ser Gly Ser Leu Ser Thr Ser Ser Ser Ser Ser
            195                 200                 205

Pro Pro Gly Thr Pro Ser Pro Ala Asp Ala Lys Ala Pro Pro Thr Ala
210                 215                 220

Cys Tyr Ala Gly Ala Gly Pro Ala Pro Ser Gln Val Lys Ser Lys Ala
225                 230                 235                 240

Lys Lys Thr Val Asp Lys His Ser Asp Glu Tyr Lys Ile Arg Arg Glu
                245                 250                 255

Arg Asn Asn Ile Ala Val Arg Lys Ser Arg Asp Lys Ala Lys Met Arg
            260                 265                 270

Asn Leu Glu Thr Gln His Lys Val Leu Glu Leu Thr Ala Glu Asn Glu
        275                 280                 285

Arg Leu Gln Lys Lys Val Glu Gln Leu Ser Arg Glu Leu Ser Thr Leu
    290                 295                 300

Arg Asn Leu Phe Lys Gln Leu Pro Glu Pro Leu Leu Ala Ser Ser Gly
305                 310                 315                 320

His Cys

<210> SEQ ID NO 7
<211> LENGTH: 147
<212> TYPE: PRT
<213> ORGANISM: Homo sapiens

<400> SEQUENCE: 7

Met Ala Ala Gly Phe Pro Tyr Ala Leu Arg Ala Tyr Leu Gly Tyr Gln
1               5                   10                  15

Ala Val Pro Ser Gly Ser Gly Ser Leu Ser Thr Ser Ser Ser
            20                  25                  30

Ser Pro Pro Gly Thr Pro Ser Pro Ala Asp Ala Lys Ala Pro Pro Thr
        35                  40                  45

Ala Cys Tyr Ala Gly Ala Gly Pro Ala Pro Ser Gln Val Lys Ser Lys
    50                  55                  60

Ala Lys Lys Thr Val Asp Lys His Ser Asp Glu Tyr Lys Ile Arg Arg
65                  70                  75                  80

Glu Arg Asn Asn Ile Ala Val Arg Lys Ser Arg Asp Lys Ala Lys Met
                85                  90                  95

Arg Asn Leu Glu Thr Gln His Lys Val Leu Glu Leu Thr Ala Glu Asn
            100                 105                 110

Glu Arg Leu Gln Lys Lys Val Glu Gln Leu Ser Arg Glu Leu Ser Thr
        115                 120                 125

Leu Arg Asn Leu Phe Lys Gln Leu Pro Glu Pro Leu Leu Ala Ser Ser
    130                 135                 140

Gly His Cys
145

<210> SEQ ID NO 8
<211> LENGTH: 1500
<212> TYPE: DNA
<213> ORGANISM: Mus sp.

<400> SEQUENCE: 8
gcccgttgcc aggcgccgcc ttataaacct cccgctcggc cgccgccgcg ccgagtccga      60
gccgcgcacg ggaccgggac gcagcggagc ccgcgggccc cgcgttcatg caccgcctgc     120
tggcctggga cgcagcatgc ctcccgccgc cgcccgccgc ctttagaccc atggaagtgg     180
ccaacttcta ctacgagccc gactgcctgg cctacggggc caaggcggcc cgcgccgcgc     240
cgcgcgcccc cgccgccgag ccggccattg gcgagcacga gcgcgccatc gacttcagcc     300
cctacctgga gccgctcgcg cccgccgcgg acttcgccgc gcccgcgccc gcgcaccacg     360
acttcctctc cgacctcttc gccgacgact acggcgccaa gccgagcaag aagcggccg      420 actacggtta cgtgagcctc ggccgcgcgg gcgccaaggc cgcgccgccc gcctgcttcc     480
cgccgccgcc tcccgcggcg ctcaaggcgg agccgggctt cgaacccgcg gactgcaagc     540
gcgcggacga cgcgcccgcc atggcggccg gtttcccgtt cgccctgcgc gcctacctgg     600
gctaccaggc gacgccgagc ggcagcagcg gcagcctgtc cacgtcgtcg tcgtccagcc     660
cgcccggcac gccgagcccc gccgacgcca aggccgcgcc cgccgcctgc ttcgcgggc     720 cgccggccgc gcccgccaag gccaaggcca agaagacggt ggacaagctg agcgacgagt     780
acaagatgcg gcgcgagcgc aacaacatcg cggtgcgcaa gagccgcgac aaggccaaga     840

```
tgcgcaacct ggagacgcag cacaaggtgc tggagctgac ggcggagaac gagcggctgc    900
agaagaaggt ggagcagctg tcgcgagagc tcagcaccct gcggaacttg ttcaagcagc    960
tgcccgagcc gctgctggcc tcggcgggcc actgctagcg cggcgcggtg cgtgggggg     1020 cgccgcggcc accgtgcgcc ctgccccgcg cgctccggcc ccgcgcgcgc gcccggacca    1080
ccgtgcgtgc cctgcgcgca cctgcacctg caccgagggg acaccgcggg cacaccgcgg    1140
gcacgcgcgg cgcacgcacc tgcacagcgc accgggtttc gggacttgat gcaatccgga    1200
tcaaacgtgg ctgagcgcgt gtggacacgg gactacgcaa cacacgtgta actgtctagc    1260
cgggccctga gtaatcacct aaagatgtt cctgcgggt tgttgatgtt tttggttttg     1320 ttttgtttt tgttttgtt ttgttttttt ttttggtctt attattttt ttgtattata       1380 taaaaagtt ctatttctat gagaaaagag gcgtatgtat atttgagaac cttttccgtt     1440
tcgagcatta aagtgaagac attttaataa actttttgg gagaatgttt aaaagccaaa    1500
```
<210> SEQ ID NO 9
<211> LENGTH: 296
<212> TYPE: PRT
<213> ORGANISM: Mus sp.

<400> SEQUENCE: 9

```
Met His Arg Leu Leu Ala Trp Asp Ala Ala Cys Leu Pro Pro Pro
  1               5                  10                  15

Ala Ala Phe Arg Pro Met Glu Val Ala Asn Phe Tyr Tyr Glu Pro Asp
             20                  25                  30

Cys Leu Ala Tyr Gly Ala Lys Ala Ala Arg Ala Ala Pro Arg Ala Pro
         35                  40                  45

Ala Ala Glu Pro Ala Ile Gly Glu His Glu Arg Ala Ile Asp Phe Ser
     50                  55                  60

Pro Tyr Leu Glu Pro Leu Ala Pro Ala Ala Asp Phe Ala Ala Pro Ala
 65                  70                  75                  80

Pro Ala His His Asp Phe Leu Ser Asp Leu Phe Ala Asp Asp Tyr Gly
                 85                  90                  95

Ala Lys Pro Ser Lys Lys Pro Ala Asp Tyr Gly Tyr Val Ser Leu Gly
            100                 105                 110

Arg Ala Gly Ala Lys Ala Ala Pro Pro Ala Cys Phe Pro Pro Pro Pro
        115                 120                 125

Pro Ala Leu Lys Ala Glu Pro Gly Phe Glu Pro Ala Asp Cys Lys
    130                 135                 140

Arg Ala Asp Asp Ala Pro Ala Met Ala Ala Gly Phe Pro Phe Ala Leu
145                 150                 155                 160

Arg Ala Tyr Leu Gly Tyr Gln Ala Thr Pro Ser Gly Ser Ser Gly Ser
                165                 170                 175

Leu Ser Thr Ser Ser Ser Ser Ser Pro Pro Gly Thr Pro Ser Pro Ala
            180                 185                 190

Asp Ala Lys Ala Ala Pro Ala Ala Cys Phe Ala Gly Pro Pro Ala Ala
        195                 200                 205

Pro Ala Lys Ala Lys Ala Lys Lys Thr Val Asp Lys Leu Ser Asp Glu
    210                 215                 220

Tyr Lys Met Arg Arg Glu Arg Asn Asn Ile Ala Val Arg Lys Ser Arg
225                 230                 235                 240

Asp Lys Ala Lys Met Arg Asn Leu Glu Thr Gln His Lys Val Leu Glu
                245                 250                 255

Leu Thr Ala Glu Asn Glu Arg Leu Gln Lys Lys Val Glu Gln Leu Ser
            260                 265                 270
```

Arg Glu Leu Ser Thr Leu Arg Asn Leu Phe Lys Gln Leu Pro Glu Pro
    275                 280                 285

Leu Leu Ala Ser Ala Gly His Cys
    290                 295

<210> SEQ ID NO 10
<211> LENGTH: 1739
<212> TYPE: DNA
<213> ORGANISM: Rattus sp.

<400> SEQUENCE: 10

| | | | | | |
|---|---|---|---|---|---|
| aggggccccg | gcgtgacgca | gcccgttgcc | aggcgccgcc | ttataaacct | ccgctcggcc | 60 |
| gccgccgagc | cgagtccgag | ccgcgcacgg | gaccgggacg | cagcggagcc | cgcgggcccc | 120 |
| gcgttcatgc | accgcctgct | ggcctgggac | gcagcatgcc | tcccgccgcc | gcccgccgcc | 180 |
| tttagaccca | tggaagtggc | caacttctac | tacgagcccg | actgcctggc | ctacggggcc | 240 |
| aaggcggccc | gcgccgcgcc | gcgcgccccc | gccgccgagc | cggccatcgg | cgagcacgag | 300 |
| cgcgccatcg | acttcagccc | ctacctggag | ccgctcgcgc | ccgccgccgc | ggacttcgcc | 360 |
| gcgcccgcgc | ccgcgcacca | cgacttcctt | tccgacctct | tcgccgacga | ctacggcgcc | 420 |
| aagccgagca | agaagccgtc | cgactacggt | tacgtgagcc | tcggccgcgc | gggcgccaag | 480 |
| gccgcaccgc | ccgcctgctt | cccgccgccg | cctcccgccg | cactcaaggc | cgagccgggc | 540 |
| tcgaacccg | cggactgcaa | gcgcgcggac | gacgcgcccg | ccatggcggc | cggcttcccg | 600 |
| ttcgccctgc | gcgcctacct | gggctaccag | gcgacgccga | gcggcagcag | cggcagcctg | 660 |
| tccacgtcgt | cgtcgtccag | cccgcccggg | acgccgagcc | ccgccgacgc | caaggccgcg | 720 |
| cccgccgcct | gcttcgcggg | gccgccggcc | gcgcccgcca | aggccaaggc | caagaaggcg | 780 |
| gtggacaagc | tgagcgacga | gtacaagatg | cggcgcgagc | gcaacaacat | cgcggtgcgc | 840 |
| aagagccgcg | acaaggccaa | gatgcgcaac | ctggagacgc | agcacaaggt | gctggagctg | 900 |
| acggcggaga | cgagcggct | gcagaagaag | gtggagcagc | tgtcgcgaga | gctcagcacg | 960 |
| ctgcggaact | tgttcaagca | gctgcccgag | ccgctgctgg | cctcggcggg | tcactgctag | 1020 |
| cccggcgggg | gtggcgtggg | ggcgccgcgg | ccaccctggg | caccgtgcgc | cctgccccgc | 1080 |
| gcgctccgtc | cccgcgcgcg | cccgggcacc | gtgcgtgcac | cgcgcgcacc | tgcacctgca | 1140 |
| ccgaggggac | accgtgggca | ccgcgcgcac | gcacctgcac | cgcgcaccgg | gtttcgggac | 1200 |
| ttgatgcaat | ccggatcaaa | cgtggctgag | cgcgtgtgga | cacgggactg | acgcaacaca | 1260 |
| cgtgtaactg | tcagccgggc | cctgagtaat | cacttaaaga | tgttcctgcg | gggttgttgc | 1320 |
| tgttgatgtt | tttcttttg | tttttgttt | tttgttttt | tttggtctt | attatttttt | 1380 |
| tgtattatat | aaaaaagttc | tatttctatg | agaaagagg | cgtatgtata | ttttgagaac | 1440 |
| cttttccgtt | tcgagcatta | aagtgaagac | attttaataa | acttttttgg | agaatgttta | 1500 |
| aaaaccttt | gggggcagta | gttggctttt | gaaaaaaat | tttttttctt | ccctcctgac | 1560 |
| tttggattta | tgcgagattt | tgtttttgt | gtttctggtg | tgtagggggc | tgcgggttat | 1620 |
| ttttggttg | tgtgtggtgg | tgggtggggg | tgtcgcatct | gggttttct | cctcccctgg | 1680 |
| cagatgggat | gccagcccct | cccccagga | gaggggcag | agtgccgggt | caggaattc | 1739 |

<210> SEQ ID NO 11
<211> LENGTH: 297
<212> TYPE: PRT
<213> ORGANISM: Rattus sp.

<400> SEQUENCE: 11

```
Met His Arg Leu Leu Ala Trp Asp Ala Ala Cys Leu Pro Pro Pro
 1               5                  10                  15

Ala Ala Phe Arg Pro Met Glu Val Ala Asn Phe Tyr Tyr Glu Pro Asp
             20                  25                  30

Cys Leu Ala Tyr Gly Ala Lys Ala Gly Arg Ala Ala Pro Arg Ala Pro
         35                  40                  45

Ala Ala Glu Pro Ala Ile Gly Glu His Glu Arg Ala Ile Asp Phe Ser
     50                  55                  60

Pro Tyr Leu Glu Pro Leu Ala Pro Ala Ala Asp Phe Ala Ala Pro
 65              70                  75                  80

Ala Pro Ala His His Asp Phe Leu Ser Asp Leu Phe Ala Asp Tyr
                 85                  90                  95

Gly Ala Lys Pro Ser Lys Lys Pro Ser Asp Tyr Gly Tyr Val Ser Leu
             100                 105                 110

Gly Arg Ala Gly Ala Lys Ala Ala Pro Pro Ala Cys Phe Pro Pro Pro
         115                 120                 125

Pro Pro Ala Ala Leu Lys Ala Glu Pro Gly Phe Glu Pro Ala Asp Cys
     130                 135                 140

Lys Arg Ala Asp Asp Ala Pro Ala Met Ala Ala Gly Phe Pro Phe Ala
145                 150                 155                 160

Leu Arg Ala Tyr Leu Gly Tyr Gln Ala Thr Pro Ser Gly Ser Ser Gly
             165                 170                 175

Ser Leu Ser Thr Ser Ser Ser Ser Pro Pro Gly Thr Pro Ser Pro
             180                 185                 190

Ala Asp Ala Lys Ala Ala Pro Ala Ala Cys Phe Ala Gly Pro Pro Ala
         195                 200                 205

Ala Pro Ala Lys Ala Lys Ala Lys Lys Ala Val Asp Lys Leu Ser Asp
     210                 215                 220

Glu Tyr Lys Met Arg Arg Glu Arg Asn Asn Ile Ala Val Arg Lys Ser
225                 230                 235                 240

Arg Asp Lys Ala Lys Met Arg Asn Leu Glu Thr Gln His Lys Val Leu
                 245                 250                 255

Glu Leu Thr Ala Glu Asn Glu Arg Leu Gln Lys Lys Val Glu Gln Leu
             260                 265                 270

Ser Arg Glu Leu Ser Thr Leu Arg Asn Leu Phe Lys Gln Leu Pro Glu
         275                 280                 285

Pro Leu Leu Ala Ser Ala Gly His Cys
     290                 295

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Ala Ala Val Leu Leu Pro Val Leu Leu Ala Ala Pro
 1               5                  10

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 13

Cys Phe Ile Thr Lys Ala Leu Gly Ile Ser Tyr Gly Arg Lys Lys Arg
 1               5                  10                  15

Arg Gln Arg Arg Arg Pro Pro Gln Gly Ser Gln Thr His
             20                  25

<210> SEQ ID NO 14
<211> LENGTH: 16
<212> TYPE: PRT
<213> ORGANISM: Homo sapiens

<400> SEQUENCE: 14

Met Gln Arg Leu Val Ala Trp Asp Pro Ala Cys Leu Pro Leu Pro Pro
 1               5                  10                  15

<210> SEQ ID NO 15
<211> LENGTH: 17
<212> TYPE: PRT
<213> ORGANISM: Homo sapiens

<400> SEQUENCE: 15

Lys Lys Thr Val Asp Lys His Ser Asp Glu Tyr Lys Ile Arg Arg Glu
 1               5                  10                  15

Arg

<210> SEQ ID NO 16
<211> LENGTH: 17
<212> TYPE: PRT
<213> ORGANISM: Homo sapiens

<400> SEQUENCE: 16

Arg Arg Glu Arg Asn Asn Ile Ala Val Arg Lys Ala Arg Asp Lys Ala
 1               5                  10                  15

Lys

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
atgcaccgcc tgctggcct                                              19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
ctagcagtga cccgccga                                               18

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:
```

-continued

Oligonucleotide

<400> SEQUENCE: 19
agcacgctgc ggaacttgtt caagcagctg                          30

210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
　　　　Oligonucleotide

<400> SEQUENCE: 20
cagctgcttg aacaagttcc gcagcgtgct                          30

<210> SEQ ID NO 21
<211> LENGTH: 105
<212> TYPE: DNA
<213> ORGANISM: Artificial Sequence
<220> FEATURE:
<223> OTHER INFORMATION: Description of Artificial Sequence:
　　　　Oligonucleotide

<400> SEQUENCE: 21
gatctgcagc tggtaccatg ggctaccatg gaacgcctgg tggcctggga cccagcatgc      60 tcccctgcc gccgccgccg cctgccttta atccggaga agtgg                      105

<210> SEQ ID NO 22
<211> LENGTH: 102
<212> TYPE: DNA
<213> ORGANISM: Artificial Sequence
<220> FEATURE:
<223> OTHER INFORMATION: Description of Artificial Sequence:
　　　　Oligonucleotide

<400> SEQUENCE: 22
ccacttctcc ggatttaaag gcaggcggcg gcggcggcag ggggagacat gctgggtccc      60
aggccaccag gcgttccatg gtagcccatg gtaccagctg ca                       102

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence:
　　　　Oligonucleotide

<400> SEQUENCE: 23
ccggatcccc atggcgggct tcccgtacgc gctgcgc                              37

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence:
　　　　Oligonucleotide

<400> SEQUENCE: 24
ccggatcccg cagtggccgg aggaggcgag caggggctc                            39

<210> SEQ ID NO 25
<211> LENGTH: 44
<212> TYPE: DNA

<213> ORGANISM: Artificial Sequence
<220> FEATURE:
<223> OTHER INFORMATION: Description of Artificial Sequence:
      Oligonucleotide

<400> SEQUENCE: 25
gtgcagatcc gagctcgaga tctgcagctg gtaccatgga attc                    44

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
gtgcagatcc gagctcgaga tctgcagctg gtaccatgga attc                    44

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
gaattccatg ca                                                       12

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
tagagtcgac                                                          10

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
agatctgcag ctggtaccat ggaattcgaa gctt                               34

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
agatctgcag ctggtaccat ggaattccat gca                                33

<210> SEQ ID NO 31
<211> LENGTH: 13
<212> TYPE: DNA
<213> ORGANISM: Artificial Sequence

```
-continued

<220> FEATURE:
<223> OTHER INFORMATION: Description of Artificial Sequence:
      Oligonucleotide

<400> SEQUENCE: 31
atggaagtgg cca                                                              13

<210> SEQ ID NO 32
<211> LENGTH: 14
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 32
tagagtcgaa gctt                                                             14

<210> SEQ ID NO 33
<211> LENGTH: 106
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33
gatctgcagc tggtaccatg gaattccatg caacgcctgg tggcctggga cccagcatgt           60
ctccccctgc cgccgccgcc gcctgccttt aaatccatgg aagtgg                         106
```